(12) United States Patent
Tada et al.

(10) Patent No.: US 8,076,080 B2
(45) Date of Patent: Dec. 13, 2011

(54) NUCLEIC ACID AMPLIFICATION PRIMERS FOR DETECTING CYTOKERATINS AND EXAMINATION METHOD WITH THE USE OF THE PRIMERS

(75) Inventors: Sachiyo Tada, Kobe (JP); Yasumasa Akai, Kobe (JP); Yasuyuki Imura, Kobe (JP); Shigeki Abe, Kobe (JP); Harumi Minekawa, Otawara (JP)

(73) Assignee: Sysmex Corporation, Hyogo (JP)

( * ) Notice: Subject to any disclaimer, the term of this patent is extended or adjusted under 35 U.S.C. 154(b) by 124 days.

(21) Appl. No.: 10/514,776

(22) PCT Filed: May 20, 2003

(86) PCT No.: PCT/JP03/06256
§ 371 (c)(1),
(2), (4) Date: Aug. 8, 2005

(87) PCT Pub. No.: WO03/097878
PCT Pub. Date: Nov. 27, 2003

(65) Prior Publication Data
US 2006/0094008 A1    May 4, 2006

(30) Foreign Application Priority Data

May 21, 2002 (JP) ................ 2002-145689
Jun. 17, 2002 (JP) ................ 2002-175271
Jul. 9, 2002 (JP) ................ 2002-199759

(51) Int. Cl.
*C12Q 1/68* (2006.01)
*C12P 19/34* (2006.01)
*C07H 21/04* (2006.01)

(52) U.S. Cl. ............. 435/6.12; 435/91.2; 536/22.1; 536/24.3

(58) Field of Classification Search ........... 435/6, 91.2, 435/6.12; 536/22.1, 24.3
See application file for complete search history.

(56) References Cited

U.S. PATENT DOCUMENTS

| | | | |
|---|---|---|---|
| 4,800,159 A * | 1/1989 | Mullis et al. | 435/91.2 |
| 6,057,105 A | 5/2000 | Hoon et al. | |
| 6,203,992 B1 | 3/2001 | Granados et al. | |
| 6,410,278 B1 | 6/2002 | Tetsu et al. | |
| 6,468,546 B1 * | 10/2002 | Mitcham et al. | 424/277.1 |
| 2004/0038253 A1 | 2/2004 | Nagamine | |
| 2006/0094008 A1 * | 5/2006 | Tada et al. | 435/6 |

FOREIGN PATENT DOCUMENTS

| | | |
|---|---|---|
| DE | 197 16 346 C1 | 11/1998 |
| WO | WO 96/17080 | 6/1996 |
| WO | WO 00/28082 A1 | 5/2000 |
| WO | WO 01/29264 A | 4/2001 |
| WO | WO 01/39784 A1 | 6/2001 |
| WO | WO 01/94629 A2 | 12/2001 |
| WO | WO 01/98539 A2 | 12/2001 |
| WO | WO 02-00929 A1 | 1/2002 |
| WO | WO 02/24902 A1 | 3/2002 |
| WO | WO 03/060116 A1 | 7/2003 |

OTHER PUBLICATIONS

Kahn et al. (2000) Breast Cancer Research and Treatment 60: 143-151.*
MGC program team (Dec. 24, 2002) Proc. Natl. Acad. Sci. vol. 99, No. 26 pp. 16899-16903.*
Notomi et al. (2000) Nucleic Acids Res. vol. 28, No. 12 e63 pp. i-vii.*
Lowe et al. Nucleic acid research, 1990, vol. 18(7), p. 1757-1761.*
Neumaier M. et al., Diagnosis of Micrometastases by the Amplification of Tissue-specific Genes, Gene, 1995, vol. 159, pp. 43 to 47.
Whittock N. V. et al.., Geneomic Organization and Amplification of the Human Keratin 15 and Keratin 19 Genes, 2000, vol. 267, pp. 462 to 465.
Funaki N. O. et al., Cytokeratin 20 mRNA in Peripheral Venous Blood of Colorectal Carcinoma Patienets, British J. of Cancer, 1998, vol. 77, pp. 1327 to 1332.
Harriet J. Kahn, et al., "RT-PCR Amplification of CK19 mRNA in the Blood of Breast Cancer Patients: Correlation with Established Prognostic Parameters", Breast Cancer Research and Treatment, 60, pp. 143-151, 2000.
T. Weber, et al., "Expression of Cytokeratin 20 in Thyroid Carcinomas and Peripheral Blood Detected by reverse Transcription Polymerase Chain Reaction", 82(1), pp. 157-160, 2000.

* cited by examiner

*Primary Examiner* — Kenneth R. Horlick
*Assistant Examiner* — Joyce Tung
(74) *Attorney, Agent, or Firm* — Sughrue Mion, PLLC

(57) ABSTRACT

It is intended to provide novel primers to be used in gene amplification reactions for detecting human cytokeratins (Human CK). A primer containing an oligonucleotide comprising a base sequence which is selected from among the the 270- to 1375-th regions of the base sequence represented by SEQ ID NO:1 and the regions of complementary strands thereof and represented by, for example, any of SEQ ID NOS:2 to 341 is constructed. Further, a primer containing an oligonucleotide comprising a base sequence which is selected from among the 270- to 930-th regions of the base sequence represented by SEQ ID NO:342 and the regions of complementary strands thereof and represented by, for example, any of SEQ ID NOS:343 to 434 is constructed. Furthermore, a primer containing an oligonucleotide comprising a base sequence which is selected from among the 340 to 490-th regions or the 495- to 1050-th regions of the base sequence represented by SEQ ID NO:435 and the regions of complementary strands thereof and represented by, for example, any of SEQ ID NOS:436 to 474 is constructed.

6 Claims, 18 Drawing Sheets

NUCLEIC ACID AMPLIFICATION PRIMERS FOR DETECTING CYTOKERATINS AND EXAMINATION METHOD WITH THE USE OF THE PRIMERS

TECHNICAL FIELD

The present invention relates to nucleic acid amplifying primers for detection of human cytokeratins.

BACKGROUND ART

Cytokeratins (hereinafter, referred to as "CK") are proteins forming fibrous backbone of a cell and form a family of at least 20 genes. As such cytokeratins, human CK18, human CK19, human CK20 and the like are known. CKs are expressed in epithelial cells.

For example, previous reports described that human CK18 is expressed not only in normal tissues such as mammary gland, lung, large intestine, stomach but also in cancerous tissues, while human CK18 is not expressed in lymph nodes which are not epithelial tissues. As to human CK19, previous reports described that it is expressed in lung cancer, stomach cancer, breast cancer, pancreatic cancer, prostate cancer and the like, and difference in expression level of human CK19 is observed between normal tissues and cancerous tissues. As to human CK20, previous reports described that it is expressed in colon cancer, stomach cancer, Merkel cell cancer, gynaecologic mucus cancer, transitional cell cancer, pancreatic cancer and bile duct cancer, and also in this case, difference in expression level of human CK20 is observed between normal tissues and cancerous tissues.

In consideration of the above facts, it is possible to know presence/absence of metastasis of cancer by examination of presence/absence of expression of human CK18, human CK19 and/or human CK20 in tissues such as lymph nodes. Also it is possible to know presence/absence of metastasis of cancer by searching for those exhibit difference in expression level between normal tissues and cancerous tissues.

A cancer cell leaving the primary lesion site will metastasize around the body through the blood stream and lymphatic system. In a surgery of cancer, accurate detection of metastasis and proper treatment based on the extent of metastasis are required so as to remove lesions as reliable as possible. For this reason, intraoperative diagnosis of cancer metastasis to lymph nodes has great significance. For example, in the case of breast cancer, the range to be removed is getting smaller for improving the QOL, and diagnosis for lymph node metastasis during the surgery can be significant guidelines for determining the minimum of lymph node dissection. In the case of esophageal cancer, detection of a site where lymph node metastasis occurs may give guidelines for selection and determination of operative procedures including ventrotomy, thoracotomy and collar incision. In the case of prostate cancer, presence of lymph node metastasis will give guidelines for decision to conduct hormonal therapy while stopping the prostatectomy. Also in the case of stomach cancer, it will give guidelines for selecting an operative procedure and therapeutic strategy after the surgery. Considering the burden on a patient, intraoperative diagnosis for cancer metastasis should be conducted rapidly.

One procedure for diagnosing cancer metastasis to lymph nodes is detecting CK proteins which are tumor markers. For example, this is achieved by freezing a resected lymph node and staining a section of the frozen tissue. However, this procedure is accompanied with a risk that micrometastasis is overlooked because only the information about the section is relied on.

Recent development in gene analysis technique has enabled effective cancer diagnoses through detection of expression of tumor marker genes. For example, PCR technique enables a target DNA fragment to be amplified to several hundreds times by repetition of dissociation of DNA strands to a single-stranded DNA, binding of primers sandwiching a specific region in the DNA strand, and synthesis of DNA by DNA polymerase (see JP-A 61-274697), and can be used as a high-sensitive analyzing technique for nucleic acids in various types of sample. For example, since the PCR technique can analyze nucleic acids in samples obtained from animal body fluids or tissues, it is useful for diagnosis of infection diseases, genetic diseases, cancers and the like.

For detection of RNA, RT-PCR technique can be used. the RT-PCR technique involves extracting RNA, for example, from tumor tissues; synthesizing cDNA by the help of reverse transcriptase (RT) using oligo(dT) or random hexamer as a primer; amplifying the cDNA using PCR technique for detection. The exemplary case of diagnosis of fibroblast tumor using the RT-PCR technique has been reported (Hokkaido Igaku Zasshi p. 135-141, Vol. 66(2), (1991)). The RT-PCR makes it possible to detect expression of mRNA of CK from ablated tissues, so that the problem that cancer metastasis is overlooked can be avoided to some extent. In the field of diagnosis of tumor or cancer, such nucleic acid amplifying methods have been put into practical use ("Kanai's manual of clinical laboratory medicine" the 31st ed., pp. 1314, KANEHARA & Co., LTD., published on Sep. 20, 1998).

However, the PCR technique necessitates an operation for denaturing a template DNA from double-strand DNA to single-strand, as well as requires repetitive amplifying reactions under plural temperature conditions. Furthermore, in general, it takes about two hours to obtain a detectable amplified product, so that it was not desirable as an intraoperative test that requires rapidity.

As a DNA amplifying method other than the PCR technique, LAMP method has been reported (refer to International Publication WO00/28082). The LAMP method is a gene amplifying method using a plurality of primers including a primer that forms a hairpin structure at a terminal of the amplified product as the strand displacement reaction proceeds. In an initial reaction, using two kinds of inner primers (FIP, RIP) and two kinds of outer primers (F3 primer, R3 primer) and a strand displacing DNA polymerase, a dumbbell-like structure having a single-strand loop at each end is synthesized from a template DNA. Starting from this structure, the amplification cycle carried out so that extension and synthesis of DNA proceed on the DNA itself as a temperate, from the 3' end of this structure. The amplified product comprises a repeated structure of plural units, and each unit comprises a set of complementary regions in the same strand that forms a region to be amplified sandwiched between the primers wherein two nucleic acids have inverted base sequences. The LAMP method does not require the operation for denaturing a template DNA from double strand to single strand by heating, and is characterized by continuous process of amplification under a constant temperature (refer to Bio Venture, Vol. 1, p. 109-115 (2001) and BIO INDUSTRY, Vol. 18, No. 2, p. 15-29 (2001)). When the template is RNA, it is possible to synthesize the starting structure in a similar manner by adding a reverse transcriptase to the composition of the reaction mixture, whereby amplification can be proceeded (RT-LAMP method). According to the LAMP method, a sufficient amount of amplified product for detection can be obtained in about 30 minutes. Therefore, the time required for detection is reduced, so that it can be applied for diagnosing cancer metastasis to lymph nodes for the purpose of rapid determination of the therapeutic strategy, for example. Furthermore, since a result can be acquired rapidly, application to the intraoperative diagnosis is also expected.

The basic concept of primers applied to the LAMP method can be found in International Publication No. WO00/28082 and International Publication NO. WO02/24902.

Primers and probes to be used in PCR for detection of human CK18 have been already reported (refer to Gene, 159(1), p. 43-47(1995)). Likewise, primers or probes to be used in PCR for detection of human CK19 have also been reported (refer to U.S. Pat. No. 6,203,992 and Breast Cancer Research and Treatment 60, p. 143-151(2000)) Also primers or probes to be used in PCR for detecting human CK20 have been reported (refer to British J. of Cancer, 77(8), p. 1327-1332(1998) and British J. of Cancer, 82(1), p157-160 (2000)).

However, nobody have reported primers to be applied to LAMP method intended for detection of human CKs, and there is a need to develop such primers. In addition, as for the primers to be applied to other nucleic acid amplifying means, there is a need to construct a new primer or a primer set that is useful for detection in addition to known primers.

(Document Of Conventional Art)
Patent document 1: International Publication No. WO00/28082
Patent document 2: International Publication No. WO02/24902
Patent document 3: U.S. Pat. No. 6,203,992
Non patent document 1: Bio Venture, Vol. 1, p. 109-115 (2001)
Non patent document 2: BIO INDUSTRY, Vol. 18, No. 2, p. 15-29 (2001)
Non patent document 3: Gene, 159(1), p. 43-47(1995)
Non patent document 4: Breast Cancer Research and Treatment 60, p. 143-151(2000)
Non patent document 5: British J. of Cancer, 77(8), p. 1327-1332(1998)
Non patent document 6: British J. of Cancer, 82(1), p157-160 (2000)

DISCLOSURE OF THE INVENTION

Problems to be Solved by the Invention

It is an object of the present invention to provide new primers for use in a nucleic acid amplifying reaction for detecting human CKs. More specifically, the present invention is directed to provide primers for nucleic acid amplification according to the LAMP method.

Means for Solving the Problems

The inventors have diligently researched for overcoming the above problems, and finally constructed primers for nucleic acid amplification which can be effectively applied to the LAMP method and used for detecting human CKs.

That is, the present invention includes:
1. A primer for nucleic acid amplification for detecting cytokeratin based on the LAMP method;
2. The primer for nucleic acid amplification according to item 1, wherein the cytokeratin is selected from the group consisting of cytokeratin 18, cytokeratin 19 and cytokeratin 20;
3. A primer for nucleic acid amplification for detecting human cytokeratin 18 comprising an oligonucleotide having a sequence selected from the following groups 1) to 5);
1) an oligonucleotide selected from a region of base position 270-1375 in a base sequence of SEQ ID NO: 1 and a complementary strand region thereof, containing at least 5 or more successive bases in SEQ ID NO.1 and/or in the complementary strand thereof,
2) an oligonucleotide having a base sequence represented by any one of SEQ ID NOs: 2 to 341,
3) a complementary strand of the oligonucleotide according to the above 1) or 2),
4) an oligonucleotide capable of hybridizing with the oligonucleotide according to any one of the above 1) to 3) under stringent conditions, and
5) an oligonucleotide comprising a base sequence obtainable from the oligonucleotides according to the above 1) to 4) wherein one to several bases are replaced, inserted, added or otherwise mutated, the oligonucleotide having a primer function;
4. A primer for nucleic acid amplification for detecting human cytokeratin 18, comprising an oligonucleotide selected from the base sequences of SEQ ID NOs: 66 to 88 or 179 to 341;
5. The primer for nucleic acid amplification according to the above 3. or 4., wherein nucleic acid amplification is conducted by the LAMP method;
6. A primer set for nucleic acid amplification for detecting human cytokeratin 18, wherein at least two kinds of primers are selected from primers for nucleic acid amplification, each primer comprising an oligonucleotide comprising a sequence selected from the following groups 1) to 4);
1) an oligonucleotide selected from a region of base position 270-1375 in a base sequence of SEQ ID NO: 1 and a complementary strand region thereof, containing at least 5 or more successive bases in SEQ ID NO.1 and/or in the complementary strand thereof,
2) an oligonucleotide having a base sequence represented by any one of SEQ ID NOs: 2 to 341,
3) a complementary strand of the oligonucleotide according to the above 1) or 2),
4) an oligonucleotide capable of hybridizing with the oligonucleotide according to any one of the above 1) to 3) under stringent conditions, and
5) an oligonucleotide comprising a base sequence obtainable from the oligonucleotides according to the above 1) to 4) wherein one to several bases are replaced, inserted, added or otherwise mutated, the oligonucleotide having a primer function;
7. The primer set for nucleic acid amplification for detecting human cytokeratin 18 according to the above 6., wherein the nucleic acid amplification is conducted by the LAMP method;
8. The primer set for nucleic acid amplification for detecting human cytokeratin 18 according to the above 7., wherein at least four kinds of primers are selected from the primers for nucleic acid amplification each comprising an oligonucleotide;
9. The primer set for nucleic acid amplification for detecting human cytokeratin 18 according to any one of the above 6. to 8., wherein at least two kinds of primers included in the primer set respectively recognize two regions of the base sequence of SEQ ID NO: 1 and/or a complementary strand thereof;
10. The primer set according to any one of the above 7. to 9., wherein the primers included in said primer set recognize at least 6 regions in the base sequence of SEQ ID NO:1 and/or the complementary strand thereof;

11. A primer set comprising a combination of primers, one of the primers being selected from (a) SEQ ID NOs: 234 to 286, the other selected from (b) SEQ ID NOs: 287 to 341, among the primers for nucleic acid amplification for detecting human cytokeratin 18, each comprising an oligonucleotide selected from the base sequences of SEQ ID NOs:234 to 341;

12. The primer set according to the above 11., further comprising a combination of primers, one of the primers being selected from (c) SEQ ID NOs: 66 to 88, the other selected from (d) SEQ ID NOs: 179 to 201, among the primers for nucleic acid amplification for detecting human cytokeratin 18 each comprising an oligonucleotide selected from the base sequences of SEQ ID NOs: 66 to 88 or SEQ ID NOs: 179 to 201;

13. The primer set according to the above 11. or 12., further comprising a combination of primers, one of the primers being selected from (e) SEQ ID NOs: 202 to 219, the other selected from (f) SEQ ID NOs: 220 to 233, among the primers for nucleic acid amplification for detecting human cytokeratin 18 each comprising an oligonucleotide selected from the base sequences of SEQ ID NOs: 202 to 233;

14. The primer set for nucleic acid amplification for detecting cytokeratin 18 comprising either one of the following groups 1) to 4);
1) a primer set including oligonucleotides having base sequences of SEQ ID NOs: 234, 287, 66 and 179 as primers,
2) a primer set including oligonucleotides having base sequences of SEQ ID NOs: 252, 297, 68 and 182 as primers,
3) a primer set including oligonucleotides having base sequences of SEQ ID NOs: 259, 307, 72 and 184 as primers,
4) a primer set including oligonucleotides having base sequences of SEQ ID NOs: 278, 331, 79 and 193 as primers;

15. The primer set for nucleic acid amplification for detecting human cytokeratin 18 comprising either one of the following groups 1) to 4);
1) a primer set including oligonucleotides having base sequences of SEQ ID NOs: 234, 287, 66, 179, 203 and 220 as primers,
2) a primer set including oligonucleotides having base sequences of SEQ ID NOs: 252, 297, 68, 182, 211 and 223 as primers,
3) a primer set including oligonucleotides having base sequences of SEQ ID NOs: 259, 307, 72, 184, 212 and 226 as primers,
4) a primer set including oligonucleotides having base sequences of SEQ ID NOs: 278, 331, 79, 193, 214 and 228 as primers;

16. The primer set for nucleic acid amplification for detecting human cytokeratin 18 comprising either one of the following groups 1) to 8);
1) a primer set including oligonucleotides having base sequences of SEQ ID NOs: 280, 334, 82 and 195 as primers,
2) a primer set including oligonucleotides having base sequences of SEQ ID NOs: 281, 335, 83 and 196 as primers,
3) a primer set including oligonucleotides having base sequences of SEQ ID NOs: 282, 336, 84 and 197 as primers,
4) a primer set including oligonucleotides having base sequences of SEQ ID NOs: 282, 337, 84 and 197 as primers,
5) a primer set including oligonucleotides having base sequences of SEQ ID NOs: 283, 338, 85 and 198 as primers,
6) a primer set including oligonucleotides having base sequences of SEQ ID NOs: 284, 339, 86 and 199 as primers,
7) a primer set including oligonucleotides having base sequences of SEQ ID NOs: 285, 340, 87 and 200 as primers,
8) a primer set including oligonucleotides having base sequences of SEQ ID NOs: 286, 341, 88 and 201 as primers;

17. The primer set for nucleic acid amplification for detecting human cytokeratin 18 comprising either one of the following groups 1) to 6);
1) a primer set including oligonucleotides having base sequences of SEQ ID NOs: 282, 336, 84, 197, 216 and 229 as primers,
2) a primer set including oligonucleotides having base sequences of SEQ ID NOs: 282, 337, 84, 197, 216 and 230 as primers,
3) a primer set including oligonucleotides having base sequences of SEQ ID NOs: 282, 337, 84, 197, 216 and 231 as primers,
4) a primer set including oligonucleotides having base sequences of SEQ ID NOs: 283, 338, 85, 198, 217 and 232 as primers,
5) a primer set including oligonucleotides having base sequences of SEQ ID NOs: 286, 341, 88, 201, 218 and 233 as primers,
6) a primer set including oligonucleotides having base sequences of SEQ ID NOs: 286, 341, 88, 201, 219 and 233 as primers;

18. A method for detecting nucleic acids of human cytokeratin 18 using a necessary primer selected from the primers according to the above 3. or 4., or a primer set selected from the primer sets according to any one of the above 5. to 17.;

19. A primer for nucleic acid amplification for detecting human cytokeratin 19 comprising an oligonucleotide having a sequence selected from the following groups 1) to 5);
1) an oligonucleotide selected from a region of base position 270-930 in a base sequence of SEQ ID NO: 342 and a complementary strand region thereof, containing at least 5 or more successive bases in SEQ ID NO.1 and/or in the complementary strand thereof,
2) an oligonucleotide having a base sequence represented by any one of SEQ ID NOs: 343 to 432,
3) a complementary strand of the oligonucleotide according to the above 1) or 2),
4) an oligonucleotide capable of hybridizing with the oligonucleotide according to any one of the above 1) to 3) under stringent conditions, and
5) an oligonucleotide comprising a base sequence obtainable from the oligonucleotides according to the above 1) to 4) wherein one to several bases are replaced, inserted, added or otherwise mutated, the oligonucleotide having a primer function;

20. A primer for nucleic acid amplification for detecting human cytokeratin 19, comprising an oligonucleotide selected from the base sequences of SEQ ID NOs: 357 to 361 or 378 to 434;

21. The primer for nucleic acid amplification for detecting human cytokeratin 19 according to the above 19. or 20., wherein the nucleic acid amplification is conducted by the LAMP method;

22. A primer set for nucleic acid amplification for detecting human cytokeratin 19, wherein at least two kinds of primers are selected from primers for nucleic acid amplification, each primer comprising an oligonucleotide comprising a sequence selected from the following groups 1) to 5);
1) an oligonucleotide selected from a region of base position 270-930 in a base sequence of SEQ ID NO: 342 and a complementary strand region thereof, containing at least 5 or more successive bases in SEQ ID NO.342 and/or in the complementary strand thereof,
2) an oligonucleotide having a base sequence represented by SEQ ID NOs: 343 to 434,
3) a complementary strand of the oligonucleotide according to the above 1) or 2), 4) an oligonucleotide capable of hybridizing with the oligonucleotide according to any one of the above 1) to 3) under stringent conditions, and 5) an oligonucleotide comprising a base sequence obtainable from the oligonucleotides according to the above 1) to 4) wherein one to several bases are replaced, inserted, added or otherwise mutated, the oligonucleotide having a primer function;

23. The primer set for detecting human cytokeratin 19 according to the above 22., wherein the nucleic acid amplification is conducted by the LAMP method;

24. The primer set for nucleic acid amplification for detecting human cytokeratin 19 according to the above 22. or 23., wherein at least four kinds of primers are selected from the primers for nucleic acid amplification each comprising an oligonucleotide;

25. The primer set for nucleic acid amplification for detecting human cytokeratin 19 according to any one of the above 22. to 24., wherein at least two kinds of primers included in the primer set respectively recognize two regions of the base sequence of SEQ ID NO: 342 and/or a complementary strand thereof;

26. The primer set for detecting human cytokeratin 19 according to any one of the above 22. to 25., wherein the primers included in said primer set recognize at least six regions in the base sequence represented by SEQ ID NO:342 and/or a complementary strand thereof;

27. A primer set comprising a combination of primers, one of the primers being selected from (a) SEQ ID NOs: 413 to 417, 419, 422 or 424 to 427, the other selected from (b) SEQ ID NOs: 418, 420, 421, 423 or 428 to 434, among the primers for nucleic acid amplification for detecting human cytokeratin 19, each comprising an oligonucleotide selected from the base sequences of SEQ ID NOs: 413 to 434;

28. The primer set according to the above 27., further comprising a combination of primers, one of the primers being selected from (c) SEQ ID NOs: 357 to 361, the other selected from (d) SEQ ID NOs: 378 to 384, among the primers for nucleic acid amplification for detecting human cytokeratin 19 each comprising an oligonucleotide selected from the base sequences of SEQ ID NOs: 357 to 361 or SEQ ID NOs: 378 to 384;

29. The primer set according to the above 27. or 28., further comprising a combination of primers, one of the primers being selected from (e) SEQ ID NOs: 385 to 398, the other selected from (f) SEQ ID NOs: 399 to 412, among the primers for nucleic acid amplification for detecting human cytokeratin 19 each comprising an oligonucleotide selected from the base sequences of SEQ ID NOs: 385 to 412;

30. A primer set comprising either one of the following combinations 1) to 4);
1) combination of primers selected respectively one from (a) SEQ ID NO: 413 to 417, (b) SEQ ID NO: 418, (c) SEQ ID NO: 357 and (d) SEQ ID NO: 378,
2) combination of primers selected respectively one from (a) SEQ ID NO: 419, (b) SEQ ID NO: 420 to 421, (c) SEQ ID NO: 358 and (d) SEQ ID NO: 379,
3) combination of primers selected respectively one from (a) SEQ ID NO: 422, (b) SEQ ID NO: 423, (c) SEQ ID NO: 359 and (d) SEQ ID NO: 380,
4) combination of primers selected respectively one from (a) SEQ ID NO: 424 to 427, (b) SEQ ID NO: 428 to 434, (c) SEQ ID NO: 360 to 361 and (d) SEQ ID NO: 381 to 384, among primers for nucleic acid amplification for detecting human cytokeratin 19 each comprising an oligonucleotide having a base sequence represented by each SEQ ID NO;

31. A primer set comprising either one of the following combinations 1) to 4);
1) combination of primers selected respectively one from (a) SEQ ID NO: 413 to 417, (b) SEQ ID NO: 418, (c) SEQ ID NO: 357, (d) SEQ ID NO: 378, (e) SEQ ID NO: 385 to 391 and (f) SEQ ID NO: 399 to 402,
2) combination of primers selected respectively one from (a) SEQ ID NO: 419, (b) SEQ ID NO: 420 to 421, (c) SEQ ID NO: 358, (d) SEQ ID NO: 379, (e) SEQ ID NO: 392 to 393 and (f) SEQ ID NO: 403 to 406,
3) combination of primers selected respectively one from (a) SEQ ID NO: 422, (b) SEQ ID NO: 423, (c) SEQ ID NO: 359, (d) SEQ ID NO: 380, (e) SEQ ID NO: 394 to 396 and (f) SEQ ID NO: 407 to 409,
4) combination of primers selected respectively one from (a) SEQ ID NO: 424 to 427, (b) SEQ ID NO: 428 to 434, (c) SEQ ID NO: 360 to 361, (d) SEQ ID NO: 381 to 384, (e) SEQ ID NO: 397 to 398 and (f) SEQ ID NO: 411 to 412;

32. A primer set for nucleic acid amplification for detecting human cytokeratin 19 comprising either one of the following groups 1) to 3); 1) a primer set including oligonucleotides having base sequences represented by SEQ ID NOs: 413, 418, 357 and 378 as primers,
2) a primer set including oligonucleotides having base sequences represented by SEQ ID NOs: 419, 421, 358 and 379 as primers.
3) a primer set including oligonucleotides having base sequences represented by SEQ ID NOs: 424, 431, 360 and 381 as primers;

33. A primer set for nucleic acid amplification for detecting human cytokeratin 19 comprising either one of the following groups 1) to 4); 1) a primer set including oligonucleotides having base sequences represented by SEQ ID NOs: 413, 418, 357, 378, 385 and 402 as primers,
2) a primer set including oligonucleotides having base sequences represented by SEQ ID NOs: 419, 421, 358, 379, 392 and 404 as primers,
3) a primer set including oligonucleotides having base sequences represented by SEQ ID NOs: 422, 423, 359, 380, 394 and 407 as primers,
4) a primer set including oligonucleotides having base sequences represented by SEQ ID NOs: 424, 431, 360, 381, 397 and 411 as primers;

34. A method for detecting nucleic acids using a necessary primer selected from the primers according to the above 19. or 20., or a primer set selected from the primer sets according to any one of the above 21. to 33.;

35. A primer for nucleic acid amplification for detecting human cytokeratin 20 comprising an oligonucleotide having a sequence selected from the following groups 1) to 5);
1) an oligonucleotide selected from a region of base position 340-490 or a region of base position 495-1050 in a base sequence of SEQ ID NO: 435 and regions of a complementary strand thereof, containing at least 5 or more successive bases in SEQ ID NO.435 and/or in the complementary strand thereof,
2) an oligonucleotide having a base sequence represented by any one of SEQ ID NOs: 436 to 460,
3) a complementary strand of the oligonucleotide according to the above 1) or 2),
4) an oligonucleotide capable of hybridizing with the oligonucleotide according to any one of the above 1) to 3) under stringent conditions, and
5) an oligonucleotide comprising abase sequence obtainable from the oligonucleotides according to the above 1) to 4)

wherein one to several bases are replaced, inserted, added or otherwise mutated, the oligonucleotide having a primer function;

36. A primer for nucleic acid amplification for detecting human cytokeratin 20, comprising an oligonucleotide selected from the base sequences of SEQ ID NOs: 443, 444 or 454 to 474;

37. The primer for nucleic acid amplification for detecting human cytokeratin 20 according to the above 35. or 36., wherein the nucleic acid amplification is conducted by the LAMP method;

38. A primer set for nucleic acid amplification for detecting human cytokeratin 20, wherein at least two kinds of primers are selected from primers for nucleic acid amplification, each primer comprising an oligonucleotide comprising a sequence selected from the following groups 1) to 5);

1) an oligonucleotide selected from a region of base position 340-1050 in a base sequence of SEQ ID NO: 435 and a complementary strand region thereof, containing at least 5 or more successive bases in SEQ ID NO. 435 and/or in the complementary strand thereof, 2) an oligonucleotide having a base sequence represented by any one of SEQ ID NOs: 436 to 460, 3) a complementary strand of the oligonucleotide according to the above 1) or 2), 4) an oligonucleotide capable of hybridizing with the oligonucleotide according to any one of the above 1) to 3) under stringent conditions, and 5) an oligonucleotide comprising a base sequence obtainable from the oligonucleotides according to the above 1) to 4) wherein one to several bases are replaced, inserted, added or otherwise mutated, the oligonucleotide having a primer function;

39. The primer set for nucleic acid amplification for detecting human cytokeratin 20 according to the above 38., wherein the nucleic acid amplification is conducted by the LAMP method;

40. The primer set for nucleic acid amplification for detecting human cytokeratin 20 according to the above 39., wherein at least four kinds of primers are selected from the primers for nucleic acid amplification each comprising an oligonucleotide;

41. The primer set for detecting human cytokeratin 20 according to any one of the above 38. to 40., wherein at least two kinds of primers included in the primer set respectively recognize two regions of the base sequence of SEQ ID NO: 435 and/or a complementary strand thereof;

42. The primer set for detecting human cytokeratin 20 according to any one of the above 38. to 41., wherein the primers included in said primer set recognize at least six regions in the base sequence represented by SEQ ID NO:435 and/or a complementary strand thereof;

43. A primer set comprising a combination of primers, one of the primers being selected from (a) SEQ ID NOs: 461 to 466, the other selected from (b) SEQ ID NOs: 468 to 473, among the primers for nucleic acid amplification for detecting human cytokeratin 20 each comprising an oligonucleotide selected from the base sequences of SEQ ID NOs: 461 to 466 or SEQ ID NOs: 468 to 473;

44. The primer set for detecting human cytokeratin 20 according to the above 43., further comprising oligonucleotides having base sequences represented by SEQ ID NO: 444 and SEQ ID NO: 455 as primers;

45. The primer set for detecting human cytokeratin 20 according to the above 43. or 44., further comprising an oligonucleotide having a base sequence represented by SEQ ID NO: 457 and/or 459 or 460 as a primer;

46. A primer set for detecting human cytokeratin 20 comprising oligonucleotides having base sequences represented by SEQ ID NOs: 443, 454, 467 and 474 as primers;

47. A primer set for detecting human cytokeratin 20, wherein an oligonucleotide having a base sequence represented by SEQ ID NO: 456 and/or 458 is used as a primer in addition to oligonucleotides having base sequences represented by SEQ ID NOs: 443, 454, 467 and 474;

48. A method for detecting nucleic acids using a necessary primer selected from the primers according to the above 35. or 36., or a primer set selected from the primer sets according to any one of the above 37. to 47.;

49. The method for detecting nucleic acids according to the above 18., 34. or 48., wherein the nucleic acid amplification is conducted by the LAMP method;

50. A reagent for use in the method for detecting nucleic acids according to the above 18., 34., 48. or 49.;

51. A reagent kit for use in the method for detecting nucleic acids according to the above 18., 34., 48. or 49.; and 52. A nucleic acid detecting system using the method for detecting nucleic acids according to the above 18., 34., 48. or 49.

BEST MODE FOR CARRYING OUT THE INVENTION

Primer Designing

Figure 1:
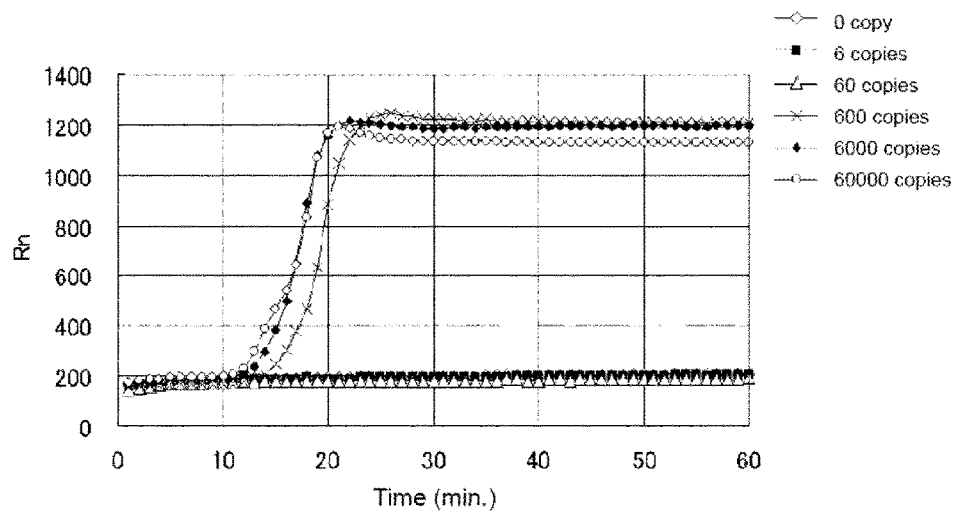
FIG. 1 is a view showing results of LAMP conducted by using Primer set I of human CK18 (Test example 1-1)
Figure 2:
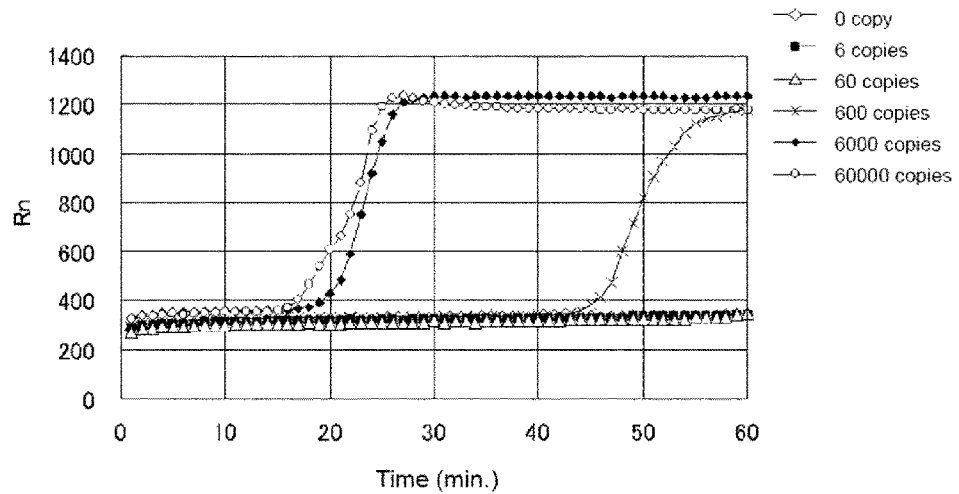
FIG. 2 is a view showing results of LAMP conducted by using Primer set II of human CK18 (Test example 1-1)
Figure 3:
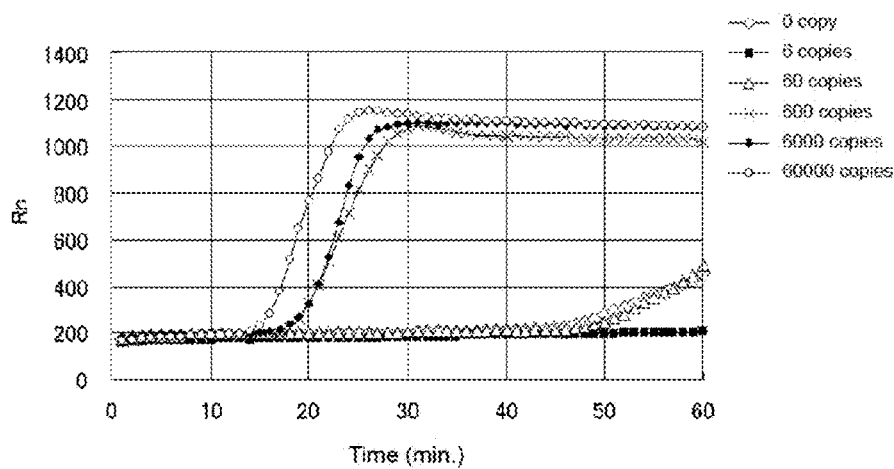
FIG. 3 is a view showing results of LAMP conducted by using Primer set III of human CK18 (Test example 1-1)
Figure 4:
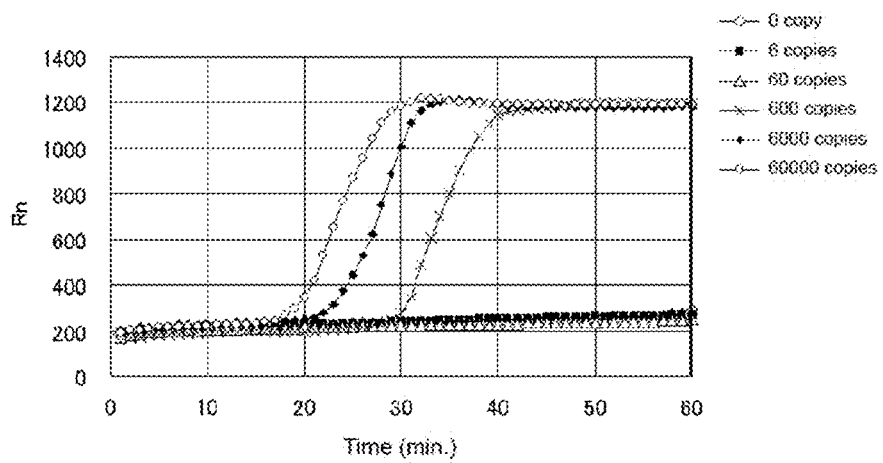
FIG. 4 is a view showing results of LAMP conducted by using Primer set IV of human CK18 (Test example 1-1)

The present invention provides a primer for nucleic acid amplification applicable to methods of amplifying nucleic acids of human CKs, preferably to the LAMP method. For example, the primer can be designed by selecting an appropriate oligonucleotide comprising at least 5 or more successive bases in known CK base sequences represented by, for example, SEQ ID NOs: 1, 342, 435 and/or complementary sequences thereof.

The basic concept of primers used in the LAMP method is as described in Patent document 1. Concretely, defining three regions F3c, F2c, F1c in this order from 3' end and three regions R3, R2, R1 in this order from 5' end of a target DNA to be amplified, and at least four primers are designed by selecting oligonucleotide chains comprising base sequences that are substantially identical with and/or substantially complementary with those of at least the above six regions.

The wording "substantially identical base sequence" is defined as follows. When a complementary strand that has been synthesized from a template having a certain base sequence hybridizes with a target base sequence and gives a starting point of synthesis of a complementary strand, the base sequence is referred to be substantially identical with the target base sequence. For example, the wording "base sequence substantially identically with F2" comprehends not only the base sequence that is perfectly identical with F2 but also the base sequences serving as templates that hybridize with F2 and give a base sequence serving as a starting point for synthesis of a complementary strand.

The term "identical" or "complementary" used herein for characterizing a base sequence constituting an oligonucleotide according to the present invention does not necessarily mean "perfectly identical" or "perfectly complementary". In other words, when referring to "identical to a certain sequence", sequences which are complementary to those capable of hybridizing with the certain sequence are also included. On the other hand, the term "complementary" means a sequence that is capable of hybridizing under stringent conditions and providing 3' end serving as a starting point of synthesis of a complementary strand.

Primers of the present invention have such a chain length that allows base-pair biding with a complementary strand while keeping a necessary specificity under a given environment in a variety of nucleic acid synthesis reaction as will be described below. Concretely, they have a length of 5 to 200 bases, more preferably 10 to 50 bases. Since the chain length of a primer that can be recognized by a known polymerase catalyzing sequence-dependent nucleic acid synthesis reaction is at least around 5 bases, the length of the hybridizing part should be longer than that. Additionally, from the view point of keeping specificity of a particular base sequence, the base sequence preferably has a length of not less than 10 bases. Too long base sequences are difficult to be prepared by chemical synthesis, so that the aforementioned chain lengths are exemplified as a preferred range.

The term "template" used herein means a nucleic acid which serves as a template for synthesis of a complementary strand. A complementary strand whose base sequence is complementary to a template is also interpreted as a strand capable of hybridizing with a template, however the relation between template and complementary strand is relative. In other words, a complementary strand can become a template.

In the present invention, primers selected from a base sequence of a target DNA each constitute either of FIP (forward inner primer), F3 primer (forward outer primer), RIP (reverse inner primer) and R3 primer (reverse outer primer).

FIP is designed to have a base sequence of F2 region which is substantially complementary with F2c region of a target DNA at its 3' end, and a base sequence which is substantially identical to F1c region of the target DNA at its 5' end. In this case, a sequence that does not depend on the target DNA may exist between the sequences of F2 and F1c. The sequence that does not depend on the target DNA may have a length of 0 to 50 bases, preferably 0 to 40 bases.

F3 primer is designed to have a base sequence substantially identical with F3 region which is substantially complementary with F3c region of a target DNA.

RIP is designed to have a base sequence of R2 region which is substantially complementary with R2c region of a target DNA at its 3' end, and a base sequence which is substantially identical to R1c region of the target DNA at its 5' end. Likewise FIP, a sequence that does not depend on the target DNA may exist between the sequences of R2 and R1c in RIP.

R3 primer is designed to have a base sequence substantially identical with R3 region which is substantially complementary with R3c region of a target DNA.

In the LAMP method, by additionally using at least one kind of loop primer, it is possible to reduce the time for amplification (refer to International Publication No. WO02/24902). The term "loop primer" refers to a primer having a complementary sequence in a single-strand part of the 5' end loop of the dumbbell structure, more concretely, between R1 region and R2 region or between F1 region and F2 region, for example. Use of a loop primer makes it possible to increase the starting points of DNA synthesis. This loop primer is designed so as to allow hybridization in a loop region where FIP or RIP that is generated in the course of DNA synthesis will not hybridize.

(Designing of Primer for Detecting Human CK18)

A primer for detecting human CK18 is designed by selecting an appropriate oligonucleotide comprising at least 5 or more successive bases from a known base sequence of 1412 bases represented by SEQ ID NO: 1 and/or a complementary sequence thereof. The base sequence represented by SEQ ID NO: 1 is based on Genbank accession No. 4557887.

A primer for detecting human CK18 is also designed by selecting a region in accordance with the aforementioned principle of primer.

Taking care of the base composition, GC content, secondary structure, Tm value and the like, the region of a primer for detecting human CK18 is selected so that the base sequence recognizing a DNA region has a length of at least 5 bases, preferably 10 to 30 bases, more preferably 17 to 25 bases. Tm value can be generally determined by Nearest Neighbor method. DNA region can be selected so that Tm value is 55 to 65° C., preferably 58 to 64° C., and GC content is 40 to 70%, preferably 50 to 65%.

With such a condition, the region of primer selected in the present invention is included in a region of base position 270-1375 of the base sequence represented by SEQ ID NO:1 and a region of complementary strand thereof, and preferably in a region of base position 280-580 and a region of complementary strand thereof.

A primer for detecting human cytokeratin CK18 is designed by selecting from the following groups 1) to 5); 1) an oligonucleotide included in a region of base position 270-1375 in a base sequence of SEQ ID NO: 1 and/or a complementary strand region thereof, containing at least 5 bases; 2) an oligonucleotide having a base sequence represented by any one of SEQ ID NOs: 2 to 41; 3) a complementary strand of the oligonucleotide according to the above 1) or 2); 4) an oligonucleotide capable of hybridizing with the oligonucleotide according to any one of the above 1) to 3) under stringent conditions, and 5) an oligonucleotide comprising abase sequence obtainable from the oligonucleotides according to the above 1) to 4) wherein one to several bases are replaced, inserted, added or otherwise mutated.

Oligonucleotides can be produced by a well-known method, for example by chemical synthesis. Alternatively, naturally occurring nucleic acid may be digested with a restriction enzyme or the like, followed by modification or coupling, thereby forming the base sequence as described above. Concretely, they can be synthesized using an oligonucleotide synthesizer (Expedite Model 8909 DNA synthesizer, manufactured by Applied Biosystems) or the like. Also oligonucleotides in which one to several bases are replaced, inserted, added or otherwise mutated can be synthesized by a well-known process. For example, synthesis of such oligonucleotide can be achieved by using site-directed mutagenesis, gene homologous recombination, primer extension or PCR technique singly or in appropriate combination, according to the method described in, for example, *Molecular Cloning: A Laboratory Manual* (2nd edition, 1989) edited by Sambrook, et al., Cold Spring Harbor Laboratory Press., Cold Spring Harbor N.Y.; *Labomanual Genetic Engineering* edited by Masaki Muramatsu, Maruzen, 1988; and *PCR technology—Principal and application of DNA amplification* edited by Ehrlichm H E., Stockton Press, 1989, or modified methods of the above using, for example Ulmer's technique (Science (1983) 219:666).

As a stringent hybridization condition, generally known conditions can be selected. One exemplary condition includes: overnight hybridization at 42° C. in a solution containing 50% formamide, 5×SSC (150 mM NaCl, 15 mM trisodium citrate), 50 mM sodium phosphate, pH 7.6, 5× Denhart's solution, 10% dextran sulfate, and 20 µg/ml of DNA; primary washing in 2×SSC·0.1% SDS at room temperature; and secondary washing in 0.1×SSC·0.1% SDS at 65° C.

In this case, since the nucleic acid template to be amplified is mRNA of human CK18, primers to be used should be designed so as not to amplify genomic DNA contained in the test sample. Concretely, at least one of the primers included in a primer set of the present invention preferably includes a region spanning a plurality of exons in human CK18 gene. Such measure makes it possible to selectively amplify sequences from mRNA of human CK18 while excluding amplification of sequences from genomic DNA.

(Designing of Primer for Detecting Human CK19)

Also a primer for detecting human CK19 is designed in a similar manner as a primer for detecting human CK18. A primer for detecting human CK19 is designed by selecting an appropriate oligonucleotide comprising at least 5 or more successive bases from a known base sequence of 1360 bases represented by SEQ ID NO: 342 and/or a complementary sequence thereof. The base sequence represented by SEQ ID NO: 342 is based on Genbank accession No. 4504916.

Also a primer for detecting human CK19 is also designed by selecting a region in accordance with the aforementioned principle of primer.

The region of primer for detecting human CK19 is included in a region of base position 270-930 of the base sequence represented by SEQ ID NO: 342 and/or a region of complementary strand thereof, and preferably in a region of base position 270-560, 370-585, 625-854 or 655-930 and/or a region of complementary strand thereof.

A primer for detecting human CK19 is designed by selecting from the following groups 1) to 5); 1) an oligonucleotide included in a region of base position 270-930 in a base sequence of SEQ ID NO: 342 and a complementary strand region thereof, preferably included in a region of base position 270-560, 370-585, 625-854 or 655-930 and/or a region of complementary strand thereof, containing at least 5 bases; 2) an oligonucleotide having a base sequence represented by any one of SEQ ID NOs: 343 to 382; 3) a complementary strand of the oligonucleotide according to the above 1) or 2); 4) an oligonucleotide capable of hybridizing with the oligonucleotide according to any one of the above 1) to 3) under stringent conditions, and 5) an oligonucleotide comprising a base sequence obtainable from the oligonucleotides according to the above 1) to 4) wherein one to several bases are replaced, inserted, added or otherwise mutated.

(Designing of Primer for Detecting Human CK20)

Also a primer for detecting human CK20 is designed in a similar manner as a primer for detecting human CK18 or CK19. A primer for detecting human CK20 is designed by selecting an appropriate oligonucleotide comprising at least 5 or more successive bases from a known base sequence of 1275 bases represented by SEQ ID NO: 435 and/or a complementary sequence thereof. The base sequence represented by SEQ ID NO: 435 is based on Genbank accession No. 402644.

Also a primer for detecting human CK20 is also designed by selecting a region in accordance with the aforementioned principle of primer.

The region of primer for detecting human CK20 is included in a region of base position 340-1050 of the base sequence represented by SEQ ID NO:435 and a region of complementary strand thereof, preferably in a region of base position 340-490 or 495-1050 and a region of complementary strand thereof, and more preferably in a region of base position 340-490, 495-570 or 790-1050 and a region of complementary strand thereof.

A primer for detecting human CK20 is designed by selecting from the following groups 1) to 5); 1) an oligonucleotide included in a region of base position 340-1050 in a base sequence of SEQ ID NO: 435 and/or a complementary strand region thereof, preferably included in a region of base position 340-490 or 495-1050 and/or a region of complementary strand thereof, and more preferably included in a region of base position 340-490, 495-570 or 790-1050 and/or a region of complementary strand thereof, containing at least 5 bases; 2) an oligonucleotide having a base sequence represented by any one of SEQ ID NOs: 436 to 474; 3) a complementary strand of the oligonucleotide according to the above 1) or 2); 4) an oligonucleotide capable of hybridizing with the oligonucleotide according to any one of the above 1) to 3) under stringent conditions, and 5) an oligonucleotide comprising a base sequence obtainable from the oligonucleotides according to the above 1) to 4) wherein one to several bases are replaced, inserted, added or otherwise mutated.

(Primer Set)

In conducting amplification of nucleic acid using a primer of the present invention, combination of two or more kinds of primers are used as a primer set. In the LAMP method, combination of at lest four kinds of primers (FIP, F3 primer, RIP, R3 primer) is used as a primer set. Additionally, one or more kind of loop primer may be combined in the primer set.

(RT-LAMP Method)

RT-LAMP method is a kind of LAMP method which uses RNA as a template. Basic concept of the LAMP method is as described in International Publication No. WO00/28082. In the RT-LAMP method, a starting point structure of LAMP method is synthesized while cDNA is synthesized from a template RNA in the same solution. More specifically, after the following step 1), the steps of 2) to 5) are repeated for extension of DNA, whereby amplification of target DNA is achieved.

1) FIP binds to a template RNA strand, and a complementary DNA strand to the template RNA strand extends. For this reaction, reverse transcriptase such as reverse transcriptase from AMV is used.
2) A complementary DNA to the template RNA strand extends while the DNA strand from FIP synthesized in the step 1) is peeled off the template RNA by F3 primer. Extension of DNA strand after that time proceeds by virtue of DNA polymerase.
3) RIP binds to the DNA strand peeled off in the step 2), and a DNA strand extends.
4) A complementary DNA strand to the DNA from FIP extends, while R3 primer peels off the DNA strand from RIP extended in the step 3), whereby a starting point structure of LAMP method is synthesized.
5) Since both ends of the DNA strand peeled off in the step 4) have sequences which are complementary with each other in the same DNA strand, these sequences hybridize with each other, providing loop structures on both ends.

Enzymes having both the reverse transcriptase activity and DNA polymerase activity such as BcaDNA polymerase are also known. By using such an enzyme, the above reaction can be conducted with one enzyme.

(Detection Method)

A DNA strand synthesized in the LAMP method has a sequence which is complementary to the own sequence, so that most part of the DNA strand forms base-pair binding. Using this characteristic, it is possible to detect an amplified product. By conducting nucleic acid amplification using primers of the present invention in the presence of fluorochromes such as ethidium bromide, SYBER GREEN I and Pico Green, which are double strand intercalators, increase in fluorescence intensity is observed as the product increases. By monitoring this, it is possible to simultaneously trace amplification of DNA and increase in fluorescence in a closed system (See "Kanai's manual of clinical laboratory medicine" the 31st ed., pp. 1318; JP-A 2001-242169, hereinafter simply referred to as "real-time method").

Furthermore, in the LAMP method, insoluble magnesium pyrophosphate is generated as a by-product during the amplification reaction, resulting in white turbidness. Therefore, by detecting the turbidity by checking the turbidness of the reaction solution by eyes or by measuring absorbance or scattered light intensity of the reaction solution, or by examining the residue on a color filter after filtration of the reaction solution through the filter, it is possible to determine presence/absence of the amplified product (See International Publication No. WO01/83817).

(Reagents, Reagent Kit Etc.)

A variety of reagents required for detecting nucleic acids using primers of the present invention can be packed into a kit form in advance. Concretely, a variety of oligonucleotides required as primers for synthesis of complementary strand or primers for replacement of the present invention; an enzyme having reverse transcriptase activity; dNTPs serving as substrates for synthesis of complementary strand; a DNA polymerase for conducting strand displacing synthesis of complementary strand; a buffer for providing a desired condition for the enzymatic reaction; agents for removing substances that inhibit the amplification reaction such as RNase inhibitor as necessary; and further reagents required for detecting a reaction product as necessary are provided in the form of a kit.

The present invention covers a primer and a primer set for nucleic acid amplification; a nucleic acid detecting method using these primers; a detection reagent used in the nucleic acid detecting method; a nucleic acid detecting kit; and an entire nucleic acid detecting system.

EXAMPLES

In the following, the present invention will be described in more detail by way of examples, however it is to be noted that the present invention will not be limited to these examples.

Example 1-1

Selection of Region from Human CK18 Base Sequence

The base sequence of human CK18 represented by SEQ ID NO: 1 was searched for positions of appropriate regions for the LAMP method using a probe designing software. As a result of selecting regions according to the criteria that Tm 58.5-63.5° C. for F1c and R1c, Tm 61.5-62.5° C. for F2 and R2, Tm 58.5-62.5° C. for F3 and R3, the regions as shown below are selected. The selected regions are included in a region of base position 340-1050 of the base sequence represented by SEQ ID NO: 1 and a complementary strand region thereof.

F1c: Complementary strand region for base position on base sequence represented by SEQ ID NO: 1

| | | |
|---|---|---|
| 442-420 | tgaagtaatggctccagtctctg | (SEQ ID NO: 2) |
| 439-418 | agtaatggctccagtctctgac | (SEQ ID NO: 3) |
| 443-421 | ttgaagtaatggctccagtctct | (SEQ ID NO: 4) |
| 419-403 | acctggggtcccttctt | (SEQ ID NO: 5) |
| 414-396 | gggtcccttcttctccaag | (SEQ ID NO: 6) |
| 413-394 | ggtcccttcttctccaagtg | (SEQ ID NO: 7) |
| 412-393 | gtcccttcttctccaagtgc | (SEQ ID NO: 8) |
| 411-392 | tcccttcttctccaagtgct | (SEQ ID NO: 9) |
| 410-392 | cccttcttctccaagtgctc | (SEQ ID NO: 10) |
| 409-390 | ccttcttctccaagtgctcc | (SEQ ID NO: 11) |
| 584-568 | acagactggcgcatggc | (SEQ ID NO: 12) |
| 620-602 | tcaatgaccttgcggagcc | (SEQ ID NO: 13) |
| 621-602 | atcaatgaccttgcggagcc | (SEQ ID NO: 14) |
| 622-603 | catcaatgaccttgcggagc | (SEQ ID NO: 15) |
| 623-603 | tcatcaatgaccttgcggagc | (SEQ ID NO: 16) |
| 666-648 | agcctcgatctctgtctcc | (SEQ ID NO: 17) |
| 743-726 | gagctggcaatctgggct | (SEQ ID NO: 18) |
| 742-725 | agctggcaatctgggctt | (SEQ ID NO: 19) |
| 741-724 | gctggcaatctgggcttg | (SEQ ID NO: 20) |
| 740-720 | ctggcaatctgggcttgtagg | (SEQ ID NO: 21) |
| 739-720 | tggcaatctgggcttgtagg | (SEQ ID NO: 22) |
| 738-719 | ggcaatctgggcttgtaggc | (SEQ ID NO: 23) |
| 756-740 | cacggtcaacccagagc | (SEQ ID NO: 24) |
| 795-777 | gatcttggcgaggtcctga | (SEQ ID NO: 25) |
| 809-789 | cggatgtctgccatgatcttg | (SEQ ID NO: 26) |
| 829-810 | ccagctcgtcatattgggcc | (SEQ ID NO: 27) |
| 913-894 | cagcagactgtgtggtgacc | (SEQ ID NO: 28) |
| 941-924 | gtgagcgtcgtctcagca | (SEQ ID NO: 29) |
| 1008-987 | gctggccttcagatttctcatg | (SEQ ID NO: 30) |
| 355-335 | ccaggctcctcactctgtcca | (SEQ ID NO: 31) |
| 430-410 | tccagtctctgacctggggtc | (SEQ ID NO: 32) |
| 588-569 | ctccacagactggcgcatgg | (SEQ ID NO: 33) |
| 769-748 | gggcatctacctccacggtcaa | (SEQ ID NO: 34) |
| 897-877 | gaccactgtggtgctctcctc | (SEQ ID NO: 35) |
| 925-904 | cagctccaacctcagcagactg | (SEQ ID NO: 36) |
| 1263-1242 | ggtttgcatggagttgctgctg | (SEQ ID NO: 37) |

F2: Region of base position on base sequence represented by SEQ ID NO: 1

| | | |
|---|---|---|
| 376-392 | gagagcaaaatccggga | (SEQ ID NO: 38) |
| 377-393 | agagcaaaatccgggag | (SEQ ID NO: 39) |
| 378-394 | gagcaaaatccgggagc | (SEQ ID NO: 40) |
| 384-400 | aatccgggagcacttgg | (SEQ ID NO: 41) |
| 369-385 | gaggctggagagcaaaa | (SEQ ID NO: 42) |
| 523-540 | cgtcttgctgctgatgac | (SEQ ID NO: 43) |
| 524-542 | gtcttgctgctgatgactt | (SEQ ID NO: 44) |
| 543-565 | tagagtcaagtatgagacagagc | (SEQ ID NO: 45) |
| 544-565 | agagtcaagtatgagacagagc | (SEQ ID NO: 46) |
| 546-566 | agtcaagtatgagacagagct | (SEQ ID NO: 47) |
| 588-604 | gaacgacatccatgggc | (SEQ ID NO: 48) |
| 660-676 | cgaggctctcaaggagg | (SEQ ID NO: 49) |
| 661-677 | gaggctctcaaggagga | (SEQ ID NO: 50) |
| 662-678 | aggctctcaaggaggag | (SEQ ID NO: 51) |
| 687-706 | catgaagaagaaccacgaag | (SEQ ID NO: 52) |
| 719-736 | gcctacaagcccagattg | (SEQ ID NO: 53) |
| 747-763 | gttgaccgtggaggtag | (SEQ ID NO: 54) |
| 768-784 | ccccaaatctcaggacc | (SEQ ID NO: 55) |
| 839-855 | accgagaggagctagac | (SEQ ID NO: 56) |
| 878-894 | aggagagcaccacagtg | (SEQ ID NO: 57) |
| 943-960 | gagctgagacgtacagtc | (SEQ ID NO: 58) |
| 295-314 | gagaccatgcaaagcctgaa | (SEQ ID NO: 59) |
| 369-388 | gaggctggagagcaaaatcc | (SEQ ID NO: 60) |
| 523-542 | cgtcttgctgctgatgactt | (SEQ ID NO: 61) |
| 708-729 | ggaagtaaaaggcctacaagcc | (SEQ ID NO: 62) |
| 837-857 | gaaccgagaggagctagacaa | (SEQ ID NO: 63) |
| 864-884 | gtctcagcagattgaggagag | (SEQ ID NO: 64) |
| 1202-1221 | tggaagatggcgaggactttt | (SEQ ID NO: 65) |

F3: Region of base position on base sequence represented by SEQ ID NO: 1

| | | |
|---|---|---|
| 322-338 | ctggcctcttacctgga | (SEQ ID NO: 66) |
| 293-309 | aggagaccatgcaaagc | (SEQ ID NO: 67) |

| | | |
|---|---|---|
| 470-489 | tcttcgcaaatactgtggac | (SEQ ID NO: 68) |
| 466-486 | cagatcttcgcaaatactgtg | (SEQ ID NO: 69) |
| 473-491 | tcgcaaatactgtggacaa | (SEQ ID NO: 70) |
| 476-495 | caaatactgtggacaatgcc | (SEQ ID NO: 71) |
| 523-540 | cgtcttgctgctgatgac | (SEQ ID NO: 72) |
| 546-566 | agtcaagtatgagacagagct | (SEQ ID NO: 73) |
| 624-643 | caccaatatcacacgactgc | (SEQ ID NO: 74) |
| 687-706 | catgaagaagaaccacgaag | (SEQ ID NO: 75) |
| 695-712 | agaaccacgaagaggaag | (SEQ ID NO: 76) |
| 747-763 | gttgaccgtggaggtag | (SEQ ID NO: 77) |
| 812-829 | cccaatatgacgagctgg | (SEQ ID NO: 78) |
| 845-864 | aggagctagacaagtactgg | (SEQ ID NO: 79) |
| 855-873 | caagtactggtctcagcag | (SEQ ID NO: 80) |
| 907-923 | tctgctgaggttggagc | (SEQ ID NO: 81) |
| 275-294 | gaggcatccagaacgagaag | (SEQ ID NO: 82) |
| 349-366 | agcctggagaccgagaac | (SEQ ID NO: 83) |
| 490-507 | aatgcccgcatcgttctg | (SEQ ID NO: 84) |
| 672-690 | ggaggagctgctcttcatg | (SEQ ID NO: 85) |
| 807-824 | ccgggcccaatatgacga | (SEQ ID NO: 86) |
| 840-859 | ccgagaggagctagacaagt | (SEQ ID NO: 87) |
| 1176-1193 | tgagatcgccacctaccg | (SEQ ID NO: 88) |

R1c: Region of base position on base sequence represented by SEQ ID NO: 1

| | | |
|---|---|---|
| 444-463 | gatcatcgaggacctgaggg | (SEQ ID NO: 89) |
| 420-442 | cagagactggagccattacttca | (SEQ ID NO: 90) |
| 424-447 | gactggagccattacttcaagatc | (SEQ ID NO: 91) |
| 425-448 | actggagccattacttcaagatca | (SEQ ID NO: 92) |
| 426-450 | ctggagccattacttcaagatcatc | (SEQ ID NO: 93) |
| 427-451 | tggagccattacttcaagatcatcg | (SEQ ID NO: 94) |
| 428-451 | ggagccattacttcaagatcatcg | (SEQ ID NO: 95) |
| 429-453 | gagccattacttcaagatcatcgag | (SEQ ID NO: 96) |
| 430-454 | agccattacttcaagatcatcgagg | (SEQ ID NO: 97) |
| 431-454 | gccattacttcaagatcatcgagg | (SEQ ID NO: 98) |
| 432-456 | ccattacttcaagatcatcgaggac | (SEQ ID NO: 99) |
| 433-457 | cattacttcaagatcatcgaggacc | (SEQ ID NO: 100) |
| 587-605 | agaacgacatccatgggct | (SEQ ID NO: 101) |
| 588-606 | gaacgacatccatgggctc | (SEQ ID NO: 102) |
| 589-607 | aacgacatccatgggctcc | (SEQ ID NO: 103) |
| 590-607 | acgacatccatgggctcc | (SEQ ID NO: 104) |
| 598-614 | catgggctccgcaaggt | (SEQ ID NO: 105) |
| 632-649 | tcacacgactgcagctgg | (SEQ ID NO: 106) |
| 624-645 | caccaatatcacacgactgcag | (SEQ ID NO: 107) |
| 630-649 | tatcacacgactgcagctgg | (SEQ ID NO: 108) |
| 631-649 | atcacacgactgcagctgg | (SEQ ID NO: 109) |
| 685-708 | ttcatgaagaagaaccacgaagag | (SEQ ID NO: 110) |
| 739-756 | agctctgggttgaccgtg | (SEQ ID NO: 111) |
| 740-756 | gctctgggttgaccgtg | (SEQ ID NO: 112) |
| 741-757 | ctctgggttgaccgtgg | (SEQ ID NO: 113) |
| 742-758 | tctgggttgaccgtgga | (SEQ ID NO: 114) |
| 743-759 | ctgggttgaccgtggag | (SEQ ID NO: 115) |
| 744-760 | tgggttgaccgtggagg | (SEQ ID NO: 116) |

-continued

| | | |
|---|---|---|
| 746-764 | ggttgaccgtggaggtaga | (SEQ ID NO: 117) |
| 747-767 | gttgaccgtggaggtagatgc | (SEQ ID NO: 118) |
| 748-767 | ttgaccgtggaggtagatgc | (SEQ ID NO: 119) |
| 749-767 | tgaccgtggaggtagatgc | (SEQ ID NO: 120) |
| 750-768 | gaccgtggaggtagatgcc | (SEQ ID NO: 121) |
| 751-768 | accgtggaggtagatgcc | (SEQ ID NO: 122) |
| 766-783 | gcccccaaatctcaggac | (SEQ ID NO: 123) |
| 812-831 | cccaatatgacgagctggct | (SEQ ID NO: 124) |
| 855-877 | caagtactggtctcagcagattg | (SEQ ID NO: 125) |
| 924-941 | tgctgagacgacgctcac | (SEQ ID NO: 126) |
| 947-966 | tgagacgtacagtccagtcc | (SEQ ID NO: 127) |
| 1016-1032 | acagcctgagggaggtg | (SEQ ID NO: 128) |
| 360-379 | cgagaaccggaggctggaga | (SEQ ID NO: 129) |
| 443-464 | agatcatcgaggacctgagggc | (SEQ ID NO: 130) |
| 592-611 | gacatccatgggctccgcaa | (SEQ ID NO: 131) |
| 778-799 | caggacctcgccaagatcatgg | (SEQ ID NO: 132) |
| 900-921 | cacacagtctgctgaggttgga | (SEQ ID NO: 133) |
| 928-948 | gagacgacgctcacagagctg | (SEQ ID NO: 134) |
| 1277-1296 | ccacccgccggatagtggat | (SEQ ID NO: 135) |

R2: Complementary strand region for base position on base sequence represented by SEQ ID NO: 1

| | | |
|---|---|---|
| 540-523 | gtcatcagcagcaagacg | (SEQ ID NO: 136) |
| 541-523 | agtcatcagcagcaagacg | (SEQ ID NO: 137) |
| 494-475 | gcattgtccacagtatttgc | (SEQ ID NO: 138) |
| 493-474 | cattgtccacagtatttgcg | (SEQ ID NO: 139) |
| 492-473 | attgtccacagtatttgcga | (SEQ ID NO: 140) |
| 491-473 | ttgtccacagtatttgcga | (SEQ ID NO: 141) |
| 490-472 | tgtccacagtatttgcgaa | (SEQ ID NO: 142) |
| 489-470 | gtccacagtatttgcgaaga | (SEQ ID NO: 143) |
| 488-468 | tccacagtatttgcgaagatc | (SEQ ID NO: 144) |
| 487-467 | ccacagtatttgcgaagatct | (SEQ ID NO: 145) |
| 486-466 | cacagtatttgcgaagatctg | (SEQ ID NO: 146) |
| 678-662 | ctcctccttgagagcct | (SEQ ID NO: 147) |
| 677-661 | tcctccttgagagcctc | (SEQ ID NO: 148) |
| 676-660 | cctccttgagagcctcg | (SEQ ID NO: 149) |
| 675-659 | ctccttgagagcctcga | (SEQ ID NO: 150) |
| 673-657 | ccttgagagcctcgatc | (SEQ ID NO: 151) |
| 672-655 | cttgagagcctcgatctc | (SEQ ID NO: 152) |
| 667-651 | gagcctcgatctctgtc | (SEQ ID NO: 153) |

-continued

| | | |
|---|---|---|
| 666-649 | agcctcgatctctgtctc | (SEQ ID NO: 154) |
| 665-649 | gcctcgatctctgtctc | (SEQ ID NO: 155) |
| 713-696 | acttcctcttcgtggttc | (SEQ ID NO: 156) |
| 721-702 | ggcctttacttcctcttcg | (SEQ ID NO: 157) |
| 714-696 | tacttcctcttcgtggttc | (SEQ ID NO: 158) |
| 762-746 | tacctccacggtcaacc | (SEQ ID NO: 159) |
| 809-792 | cggatgtctgccatgatc | (SEQ ID NO: 160) |
| 808-790 | ggatgtctgccatgatctt | (SEQ ID NO: 161) |
| 829-812 | ccagctcgtcatattggg | (SEQ ID NO: 162) |
| 877-858 | caatctgctgagaccagtac | (SEQ ID NO: 163) |
| 874-856 | tctgctgagaccagtactt | (SEQ ID NO: 164) |
| 922-906 | ctccaacctcagcagac | (SEQ ID NO: 165) |
| 985-969 | agtccaggtcgatctcc | (SEQ ID NO: 166) |
| 1006-987 | tggccttcagatttctcatg | (SEQ ID NO: 167) |
| 1011-994 | caagctggccttcagatt | (SEQ ID NO: 168) |
| 1086-1070 | aaggtgcagcaggatcc | (SEQ ID NO: 169) |
| 437-417 | taatggctccagtctctgacc | (SEQ ID NO: 170) |
| 515-496 | tcaatctgcagaacgatgcg | (SEQ ID NO: 171) |
| 669-649 | gagagcctcgatctctgtctc | (SEQ ID NO: 172) |
| 669-650 | gagagcctcgatctctgtct | (SEQ ID NO: 173) |

-continued

| 857-837 | ttgtctagctcctctcggttc | (SEQ ID NO: 174) |
| 857-838 | ttgtctagctcctctcggtt | (SEQ ID NO: 175) |
| 981-962 | caggtcgatctccaaggact | (SEQ ID NO: 176) |
| 1008-989 | gctggccttcagatttctca | (SEQ ID NO: 177) |
| 1350-1331 | gctggcttaatgcctcagaa | (SEQ ID NO: 178) |

R3: Complementary strand region for base position on base sequence represented by SEQ ID NO: 1

| 566-546 | agctctgtctcatacttgact | (SEQ ID NO: 179) |
| 541-523 | agtcatcagcagcaagacg | (SEQ ID NO: 180) |
| 540-523 | 9gtcatcagcagcaagacg | (SEQ ID NO: 181) |
| 721-702 | ggccttttacttcctcttcg | (SEQ ID NO: 182) |
| 713-696 | acttcctcttcgtggttc | (SEQ ID NO: 183) |
| 740-724 | ctggcaatctgggcttg | (SEQ ID NO: 184) |
| 786-769 | gaggtcctgagatttggg | (SEQ ID NO: 185) |
| 854-837 | tctagctcctctcggttc | (SEQ ID NO: 186) |
| 877-858 | caatctgctgagaccagtac | (SEQ ID NO: 187) |
| 922-906 | ctccaacctcagcagac | (SEQ ID NO: 188) |
| 910-894 | cagactgtgtggtgacc | (SEQ ID NO: 189) |
| 893-877 | actgtggtgctctcctc | (SEQ ID NO: 190) |
| 960-943 | gactgtacgtctcagctc | (SEQ ID NO: 191) |
| 1021-1005 | ggctgttctccaagctg | (SEQ ID NO: 192) |
| 1056-1039 | catctgtagggcgtagcg | (SEQ ID NO: 193) |
| 1141-1125 | catactcctgggcctgg | (SEQ ID NO: 194) |
| 476-458 | gcgaagatctgagccctca | (SEQ ID NO: 195) |
| 538-521 | catcagcagcaagacggg | (SEQ ID NO: 196) |
| 688-670 | tgaagagcagctcctcctt | (SEQ ID NO: 197) |
| 885-866 | gctctcctcaatctgctgag | (SEQ ID NO: 198) |
| 1008-989 | gctggccttcagatttctca | (SEQ ID NO: 199) |
| 1030-1012 | cctccctcaggctgttctc | (SEQ ID NO: 200) |
| 1370-1352 | ccaaagggtaccctgcttc | (SEQ ID NO: 201) |

Loop F: Complementary strand region for base position on base sequence represented by SEQ ID NO: 1

| 419-403 | acctggggtcccttctt | (SEQ ID NO: 202) |
| 414-396 | gggtcccttcttctccaag | (SEQ ID NO: 203) |
| 413-394 | ggtcccttcttctccaagtg | (SEQ ID NO: 204) |

| 399-380 | caagtgctcccggattttgc | (SEQ ID NO: 205) |
| 398-380 | aagtgctcccggattttgc | (SEQ ID NO: 206) |
| 397-379 | agtgctcccggattttgct | (SEQ ID NO: 207) |
| 396-378 | gtgctcccggattttgctc | (SEQ ID NO: 208) |
| 395-377 | tgctcccggattttgctct | (SEQ ID NO: 209) |
| 394-376 | gctcccggattttgctctc | (SEQ ID NO: 210) |
| 567-544 | cagctctgtctcatacttgactct | (SEQ ID NO: 211) |
| 584-568 | acagactggcgcatggc | (SEQ ID NO: 212) |
| 709-688 | cctcttcgtggttcttcttcat | (SEQ ID NO: 213) |
| 916-898 | cctcagcagactgtgtggt | (SEQ ID NO: 214) |
| 913-894 | cagcagactgtgtggtgacc | (SEQ ID NO: 215) |
| 567-544 | cagctctgtctcatacttgactct | (SEQ ID NO: 216) |
| 743-726 | gagctggcaatctgggct | (SEQ ID NO: 217) |
| 1243-1224 | tgtccaaggcatcaccaaga | (SEQ ID NO: 218) |
| 1242-1222 | gtccaaggcatcaccaagatt | (SEQ ID NO: 219) |

Loop R: Region of base position on base sequence represented by SEQ ID NO: 1

| 474-495 | cgcaaatactgtggacaatgcc | (SEQ ID NO: 220) |
| 466-489 | cagatcttcgcaaatactgtggac | (SEQ ID NO: 221) |
| 444-463 | gatcatcgaggacctgaggg | (SEQ ID NO: 222) |
| 626-646 | ccaatatcacacgactgcagc | (SEQ ID NO: 223) |
| 617-640 | ttgatgacaccaatatcacacgac | (SEQ ID NO: 224) |
| 632-649 | tcacacgactgcagctgg | (SEQ ID NO: 225) |
| 659-676 | tcgaggctctcaaggagg | (SEQ ID NO: 226) |
| 767-784 | cccccaaatctcaggacc | (SEQ ID NO: 227) |
| 970-986 | gagatcgacctggactc | (SEQ ID NO: 228) |
| 622-643 | gacaccaatatcacacgactgc | (SEQ ID NO: 229) |
| 621-643 | tgacaccaatatcacacgactgc | (SEQ ID NO: 230) |
| 623-644 | acaccaatatcacacgactgca | (SEQ ID NO: 231) |
| 810-829 | ggcccaatatgacgagctgg | (SEQ ID NO: 232) |
| 1296-1315 | tggcaaagtggtgtctgaga | (SEQ ID NO: 233) |

Example 1-2

Designing of Primer for Detecting CK18

From the sequences of the regions selected in Example 1-1, the following primers for nucleic acid amplification to be applied to the LAMP method were obtained.
FIP: Primer having base sequence in which base sequences of regions F1c and F2 are coupled

| 09FA971-376 | tgaagtaatggctccagtctctggagagcaaaatccggga | (SEQ ID NO: 234) |
| 09FA971-377 | tgaagtaatggctccagtctctgagagcaaaatccggag | (SEQ ID NO: 235) |

-continued

| | | |
|---|---|---|
| 09FA971-378 | tgaagtaatggctccagtctctggagcaaaatccgggagc | (SEQ ID NO: 236) |
| 09FA971-384 | tgaagtaatggctccagtctctgaatccgggagcacttgg | (SEQ ID NO: 237) |
| 09FA974-376 | agtaatggctccagtctctgacgagagcaaaatccggga | (SEQ ID NO: 238) |
| 09FA974-377 | agtaatggctccagtctctgacgagagcaaaatccgggag | (SEQ ID NO: 239) |
| 09FA974-378 | agtaatggctccagtctctgacgagcaaaatccgggagc | (SEQ ID NO: 240) |
| 09FA974-384 | agtaatggctccagtctctgacaatccgggagcacttgg | (SEQ ID NO: 241) |
| 09FA970-376 | ttgaagtaatggctccagtctctgagagcaaaatccggga | (SEQ ID NO: 242) |
| 09FA970-377 | ttgaagtaatggctccagtctctagagcaaaatccgggag | (SEQ ID NO: 243) |
| 09FA970-378 | ttgaagtaatggctccagtctctgagcaaaatccgggagc | (SEQ ID NO: 244) |
| 09FA970-384 | ttgaagtaatggctccagtctctaatccgggagcacttgg | (SEQ ID NO: 245) |
| 09FA999-369 | gggtcccttcttctccaaggaggctggagagcaaaa | (SEQ ID NO: 246) |
| 09FA994-369 | acctggggtcccttcttgaggctggagagcaaaa | (SEQ ID NO: 247) |
| 09FA1000-369 | ggtcccttcttctccaagtggaggctggagagcaaaa | (SEQ ID NO: 248) |
| 09FA1002-369 | tcccttcttctccaagtgctgaggctggagagcaaaa | (SEQ ID NO: 249) |
| 09FA1004-369 | ccttcttctccaagtgctccgaggctggagagcaaaa | (SEQ ID NO: 250) |
| 12FA829-523 | acagactggcgcatggccgtcttgctgctgatgac | (SEQ ID NO: 251) |
| 12FA829-524 | acagactggcgcatggcgtcttgctgctgatgactt | (SEQ ID NO: 252) |
| 13FA793-543 | tcaatgaccttgcggagcctagagtcaagtatgagacagagc | (SEQ ID NO: 253) |
| 13FA793-544 | tcaatgaccttgcggagccagagtcaagtatgagacagagc | (SEQ ID NO: 254) |
| 13FA793-546 | tcaatgaccttgcggagccagtcaagtatgagacagagct | (SEQ ID NO: 255) |
| 13FA792-543 | atcaatgaccttgcggagcctagagtcaagtatgagacagagc | (SEQ ID NO: 256) |
| 13FA792-544 | atcaatgaccttgcggagccagagtcaagtatgagacagagc | (SEQ ID NO: 257) |
| 13FA792-546 | atcaatgaccttgcggagccagtcaagtatgagacagagct | (SEQ ID NO: 258) |
| 13FA791-543 | catcaatgaccttgcggagctagagtcaagtatgagacagagc | (SEQ ID NO: 259) |
| 13FA791-544 | catcaatgaccttgcggagcagagtcaagtatgagacagagc | (SEQ ID NO: 260) |
| 13FA791-546 | catcaatgaccttgcggagcagtcaagtatgagacagagct | (SEQ ID NO: 261) |
| 13FA790-543 | tcatcaatgaccttgcggagctagagtcaagtatgagacagagc | (SEQ ID NO: 262) |
| 13FA790-544 | tcatcaatgaccttgcggagcagagtcaagtatgagacagagc | (SEQ ID NO: 263) |
| 13FA790-546 | tcatcaatgaccttgcggagcagtcaagtatgagacagagct | (SEQ ID NO: 264) |
| 14FA747-588 | agcctcgatctctgtctccgaacgacatccatgggc | (SEQ ID NO: 265) |
| 18FA675-660 | ggcaatctgggcttgtaggccgaggctctcaaggagg | (SEQ ID NO: 266) |
| 18FA670-660 | gagctggcaatctgggctcgaggctctcaaggagg | (SEQ ID NO: 267) |
| 18FA670-662 | gagctggcaatctgggctaggctctcaaggaggag | (SEQ ID NO: 268) |
| 18FA674-660 | tggcaatctgggcttgtaggcgaggctctcaaggagg | (SEQ ID NO: 269) |
| 18FA674-662 | tggcaatctgggcttgtaggaggctctcaaggaggag | (SEQ ID NO: 270) |
| 18FA675-661 | ggcaatctgggcttgtaggcgaggctctcaaggagga | (SEQ ID NO: 271) |
| 18FA675-662 | ggcaatctgggcttgtaggcaggctctcaaggaggag | (SEQ ID NO: 272) |
| 19FA657-687 | cacggtcaacccagagccatgaagaagaaccacgaag | (SEQ ID NO: 273) |
| 21FA618-719 | gatcttggcgaggtcctgagcctacaagcccagattg | (SEQ ID NO: 274) |
| 21FA604-747 | cggatgtctgccatgatcttggttgaccgtggaggtag | (SEQ ID NO: 275) |
| 23FA584-768 | ccagctcgtcatattgggcccccaaatctcaggacc | (SEQ ID NO: 276) |

-continued

| | | |
|---|---|---|
| 27FA500-839 | cagcagactgtgtggtgaccaccgagaggagctagac | (SEQ ID NO: 277) |
| 29FA472-878 | gtgagcgtcgtctcagcaaggagagcaccacagtg | (SEQ ID NO: 278) |
| 32FA405-943 | gctggccttcagatttctcatggagctgagacgtacagtc | (SEQ ID NO: 279) |
| ek 335-295 | ccaggctcctcactctgtccagagaccatgcaaagcctgaa | (SEQ ID NO: 280) |
| ek 410-369 | tccagtctctgacctggggtcgaggctggagagcaaaa | (SEQ ID NO: 281) |
| ek 569-523 | ctccacagactggcgcatggcgtcttgctgctgatgac | (SEQ ID NO: 282) |
| ek 748-708 | gggcatctacctccacggtcaaggaagtaaaaggcctacaagcc | (SEQ ID NO: 283) |
| ek 877-837 | gaccactgtggtgctctcctcgaaccgagaggagctagacaa | (SEQ ID NO: 284) |
| ek 904-864 | cagctccaacctcagcagactggtctcagcagattgaggagag | (SEQ ID NO: 285) |
| ek 1242-1202 | ggtttgcatggagttgctgctgtggaagatggcgaggactttt | (SEQ ID NO: 286) |

RIP: Primer having base sequence in which base sequences of regions R1c and R2 are coupled

| | | |
|---|---|---|
| 09RA444-873 | gatcatcgaggacctgaggggtcatcagcagcaagacg | (SEQ ID NO: 287) |
| 09RA444-872 | gatcatcgaggacctgagggagtcatcagcagcaagacg | (SEQ ID NO: 288) |
| 09RA420-927 | cagagactggagccattacttcacacagtatttgcgaagatctg | (SEQ ID NO: 289) |
| 09RA420-925 | cagagactggagccattacttcatccacagtatttgcgaagatc | (SEQ ID NO: 290) |
| 09RA420-923 | cagagactggagccattacttcatgtccacagtatttgcgaa | (SEQ ID NO: 291) |
| 09RA420-921 | cagagactggagccattacttcaattgtccacagtatttgcga | (SEQ ID NO: 292) |
| 09RA420-919 | cagagactggagccattacttcagcattgtccacagtatttgc | (SEQ ID NO: 293) |
| 09RA424-927 | gactggagccattacttcaagatccacagtatttgcgaagatctg | (SEQ ID NO: 294) |
| 09RA424-923 | gactggagccattacttcaagatctgtccacagtatttgcgaa | (SEQ ID NO: 295) |
| 09RA424-921 | gactggagccattacttcaagatcattgtccacagtatttgcga | (SEQ ID NO: 296) |
| 12RA598-737 | catgggctccgcaaggtcctccttgagagcctcg | (SEQ ID NO: 297) |
| 12RA587-746 | agaacgacatccatgggctgagcctcgatctctgtc | (SEQ ID NO: 298) |
| 12RA588-737 | gaacgacatccatgggctccctccttgagagcctcg | (SEQ ID NO: 299) |
| 12RA588-746 | gaacgacatccatgggctcgagcctcgatctctgtc | (SEQ ID NO: 300) |
| 12RA588-748 | gaacgacatccatgggctcgcctcgatctctgtctc | (SEQ ID NO: 301) |
| 12RA590-737 | acgacatccatgggctccctccttgagagcctcg | (SEQ ID NO: 302) |
| 12RA590-746 | acgacatccatgggctccgagcctcgatctctgtc | (SEQ ID NO: 303) |
| 12RA590-748 | acgacatccatgggctccgcctcgatctctgtctc | (SEQ ID NO: 304) |
| 12RA598-740 | catgggctccgcaaggtccttgagagcctcgatc | (SEQ ID NO: 305) |
| 12RA598-746 | catgggctccgcaaggtgagcctcgatctctgtc | (SEQ ID NO: 306) |
| 13RA632-700 | tcacacgactgcagctggacttcctcttcgtggttc | (SEQ ID NO: 307) |
| 13RA632-692 | tcacacgactgcagctggggccttttacttcctcttcg | (SEQ ID NO: 308) |
| 13RA632-699 | tcacacgactgcagctggtacttcctcttcgtggttc | (SEQ ID NO: 309) |
| 13RA624-700 | caccaatatcacacgactgcagacttcctcttcgtggttc | (SEQ ID NO: 310) |
| 13RA624-699 | caccaatatcacacgactgcagtacttcctcttcgtggttc | (SEQ ID NO: 311) |
| 13RA624-692 | caccaatatcacacgactgcagggccttttacttcctcttcg | (SEQ ID NO: 312) |
| 13RA631-700 | atcacacgactgcagctggacttcctcttcgtggttc | (SEQ ID NO: 313) |
| 13RA631-699 | atcacacgactgcagctggtacttcctcttcgtggttc | (SEQ ID NO: 314) |
| 13RA631-692 | atcacacgactgcagctggggccttttacttcctcttcg | (SEQ ID NO: 315) |

```
13RA630-700    tatcacacgactgcagctggacttcctcttcgtggttc    (SEQ ID NO: 316)

13RA630-699    tatcacacgactgcagctggtacttcctcttcgtggttc   (SEQ ID NO: 317)

13RA630-692    tatcacacgactgcagctggggccttttacttcctcttcg  (SEQ ID NO: 318)

14RA685-651    ttcatgaagaagaaccacgaagagtacctccacggtcaacc (SEQ ID NO: 319)

18RA743-604    ctgggttgaccgtggagcggatgtctgccatgatc       (SEQ ID NO: 320)

18RA743-605    ctgggttgaccgtggagggatgtctgccatgatctt      (SEQ ID NO: 321)

18RA747-604    gttgaccgtggaggtagatgccggatgtctgccatgatc   (SEQ ID NO: 322)

18RA749-604    tgaccgtggaggtagatgccggatgtctgccatgatc     (SEQ ID NO: 323)

18RA751-604    accgtggaggtagatgcccggatgtctgccatgatc      (SEQ ID NO: 324)

18RA749-605    tgaccgtggaggtagatgcggatgtctgccatgatctt    (SEQ ID NO: 325)

18RA751-605    accgtggaggtagatgccggatgtctgccatgatctt     (SEQ ID NO: 326)

19RA766-584    gcccccaaatctcaggacccagctcgtcatattggg      (SEQ ID NO: 327)

21RA812-536    cccaatatgacgagctggctcaatctgctgagaccagtac  (SEQ ID NO: 328)

23RA855-491    caagtactggtctcagcagattgctccaacctcagcagac  (SEQ ID NO: 329)

27RA924-428    tgctgagacgacgctcacagtccaggtcgatctcc       (SEQ ID NO: 330)

29RA947-402    tgagacgtacagtccagtcccaagctggccttcagatt    (SEQ ID NO: 331)

29RA947-407    tgagacgtacagtccagtcctggccttcagatttctcatg  (SEQ ID NO: 332)

32RA1016-327   acagcctgagggaggtgaaggtgcagcaggatcc        (SEQ ID NO: 333)

ek 360-417     cgagaaccggaggctggagataatggctccagtctctgacc (SEQ ID NO: 334)

ek 443-496     agatcatcgaggacctgagggctcaatctgcagaacgatgcg (SEQ ID NO: 335)

ek 592-649     gacatccatgggctccgcaagagagcctcgatctctgtctc (SEQ ID NO: 336)

ek 592-650     gacatccatgggctccgcaagagagcctcgatctctgtct  (SEQ ID NO: 337)

ek 778-837     caggacctcgccaagatcatgggaaccgagaggagctagacaa (SEQ ID NO: 338)

ek 900-962     cacacagtctgctgaggttggacaggtcgatctccaaggact (SEQ ID NO: 339)

ek 928-989     gagacgacgctcacagagctggctggccttcagatttctca (SEQ ID NO: 340)

ek 1277-1331   ccacccgccggatagtggatgctggcttaatgcctcagaa  (SEQ ID NO: 341)
```

F3 primer: (primer comprising base sequence represented by respective SEQ ID NO)

F309-322 (SEQ ID NO: 66), F309-293 (SEQ ID NO: 67), F312-470 (SEQ ID NO: 68), F312-466 (SEQ ID NO: 69), F312-473 (SEQ ID NO: 70), F312-476 (SEQ ID NO: 71), F313-523 (SEQ ID NO: 72), F314-546 (SEQ ID NO: 73), F319-624 (SEQ ID NO: 74), F321-687 (SEQ ID NO: 75), F321-695 (SEQ ID NO: 76), F323-747 (SEQ ID NO: 77), F327-812 (SEQ ID NO: 78), F329-845 (SEQ ID NO: 79), F329-855 (SEQ ID NO: 80), F332-907 (SEQ ID NO: 81), F3 8 (SEQ ID NO: 82), F3 13 (SEQ ID NO: 83), F3 14 (SEQ ID NO: 84), F3 16 (SEQ ID NO: 85), F3 23 (SEQ ID NO: 86), F3 29 (SEQ ID NO: 87) F3 37 (SEQ ID NO: 88)

R3 primer: (primer comprising base sequence represented by respective SEQ ID NO)

R309-847 (SEQ ID NO: 179), R309-872 (SEQ ID NO: 180),
R309-873 (SEQ ID NO: 181), R312-692 (SEQ ID NO: 182),
R312-700 (SEQ ID NO: 183), R313-673(SEQ ID NO: 184),
R314-627 (SEQ ID NO: 185), R318-559(SEQ ID NO: 186),
R319-536 (SEQ ID NO: 187), R321-491(SEQ ID NO: 188),
R321-503 (SEQ ID NO: 189), R321-520(SEQ ID NO: 190),
R323-453 (SEQ ID NO: 191), R327-392(SEQ ID NO: 192),
R329-357 (SEQ ID NO: 193), R332-272(SEQ ID NO: 194),
B3 8 (SEQ ID NO: 195), B3 13 (SEQ ID NO: 196),
B3 14 (SEQ ID NO: 197), B3 19 (SEQ ID NO: 198),
B3 21 (SEQ ID NO: 199), B3 35 (SEQ ID NO: 200),
B3 37 (SEQ ID NO: 201)

Loop primer: (primer comprising base sequence represented by respective SEQ ID NO)

LF09-994 (SEQ ID NO: 202), LF09-999 (SEQ ID NO: 203),
LF09-1000 (SEQ ID NO: 204), LF09-1014(SEQ ID NO: 205),
LF09-1015 (SEQ ID NO: 206), LF09-1016(SEQ ID NO: 207),
LF09-1017 (SEQ ID NO: 208), LF09-1018(SEQ ID NO: 209),
LF09-1019 (SEQ ID NO: 210), LF12-846 (SEQ ID NO: 211),

LF13-829 (SEQ ID NO: 212), LF18-704 (SEQ ID NO: 213),
LF29-497 (SEQ ID NO: 214), LF29-500 (SEQ ID NO: 215),
LF 14 (SEQ ID NO: 216), LF 20 (SEQ ID NO: 217),
LF 371 (SEQ ID NO: 218), LF 372 (SEQ ID NO: 219)
LR09-474 (SEQ ID NO: 220), LR09-466 (SEQ ID NO: 221),
LR09-444 (SEQ ID NO: 222), LR12-626 (SEQ ID NO: 223),
LR12-617 (SEQ ID NO: 224), LR12-632 (SEQ ID NO: 225),
LR13-659 (SEQ ID NO: 226), LR18-767 (SEQ ID NO: 227),
LR29-970 (SEQ ID NO: 228), LB 14 (SEQ ID NO: 229), LB 151 (SEQ ID NO: 230), LB 152 (SEQ ID NO: 231), LB 371 (SEQ ID NO: 232), LB 372 (SEQ ID NO: 233)

Example 2-1

Selection of Region from Human CK19 Base Sequence

The base sequence of human CK19 represented by SEQ ID NO: 342 was searched for positions of appropriate regions for the LAMP method using a probe designing software. As a result of selecting regions according to the criteria that Tm 58.5-63.5° C. for F1c and R1c, Tm 61.5-62.5° C. for F2 and R2, Tm 58.5-62.5° C. for F3 and R3, the regions as shown below are selected. The selected regions are included in a region of base position 270-930 of the base sequence represented by SEQ ID NO: 342 and a complementary strand region thereof.

F1c: Regions on complementary strand of base sequence represented by SEQ ID NO: 342

```
426-405
5'-tgtagtagtggctgtagtcgcg-3'      (SEQ ID NO: 343)

429-407
5'-tcgtgtagtagtggctgtagtcg-3'     (SEQ ID NO: 344)

479-458
5'-ggagttctcaatggtggcacca-3'      (SEQ ID NO: 345)

716-700
5'-ttggcccctcagcgtac-3'           (SEQ ID NO: 346)

752-735
5'-agcggaatccacctccac-3'          (SEQ ID NO: 347)

747-728
5'-aatccacctccacactgacc-3'        (SEQ ID NO: 348)

746-728
5'-atccacctccacactgacc-3'         (SEQ ID NO: 349)

745-728
5'-tccacctccacactgacc-3'          (SEQ ID NO: 350)
```

F2: Regions on base sequence represented by SEQ ID NO: 342

```
352-370
5'-agctagaggtgaagatccg-3'         (SEQ ID NO: 351)

364-380
5'-agatccgcgactggtac-3'           (SEQ ID NO: 352)

360-376
5'-gtgaagatccgcgactg-3'           (SEQ ID NO: 353)

417-437
5'-actactacacgaccatccagg-3'       (SEQ ID NO: 354)

658-674
5'-aagagctggcctacctg-3'           (SEQ ID NO: 355)

690-709
5'-gaggaaatcagtacgctgag-3'        (SEQ ID NO: 356)
```

F3: Regions on base sequence represented by SEQ ID NO: 342

```
275-293  5'-gctaaccatgcagaacctc-3'   (SEQ ID NO: 357)

375-392  5'-tggtaccagaagcagggg-3'    (SEQ ID NO: 358)

628-645  5'-acctggagatgcagatcg-3'    (SEQ ID NO: 359)

658-674  5'-aagagctggcctacctg-3'     (SEQ ID NO: 360)

661-677  5'-agctggcctacctgaag-3'     (SEQ ID NO: 361)
```

R1c: Regions on base sequence represented by SEQ ID NO: 342

```
533-516
5'-gtgccaccattgagaactcc-3'         (SEQ ID NO: 362)

485-505
5'-tgtcctgcagatcgacaacgc-3'        (SEQ ID NO: 363)

486-506
5'-gtcctgcagatcgacaacgcc-3'        (SEQ ID NO: 364)

727-744
5'-aggtcagtgtggaggtgg-3'           (SEQ ID NO: 365)

764-783
5'-tctcgccaagatcctgagtg-3'         (SEQ ID NO: 366)

766-785
5'-tcgccaagatcctgagtgac-3'         (SEQ ID NO: 367)

772-793
5'-agatcctgagtgacatgcgaag-3'       (SEQ ID NO: 368)
```

R2: Regions on complementary strand of base sequence represented by SEQ ID NO: 342

```
533-516  5'-ggttcggaagtcatctgc-3'    (SEQ ID NO: 369)

545-526  5'-cgtctcaaacttggttcgga-3'  (SEQ ID NO: 370)

547-528  5'-tccgtctcaaacttggttcg-3'  (SEQ ID NO: 371)

790-773  5'-gcatgtcactcaggatc-3'     (SEQ ID NO: 372)

841-824  5'-caggcttcagcatccttc-3'    (SEQ ID NO: 373)

848-832  5'-ggtgaaccaggcttcag-3'     (SEQ ID NO: 374)

847-831  5'-gtgaaccaggcttcagc-3'     (SEQ ID NO: 375)

845-828  5'-gaaccaggcttcagcatc-3'    (SEQ ID NO: 376)

843-827  5'-accaggcttcagcatcc-3'     (SEQ ID NO: 377)
```

R3: Regions on complementary strand of base sequence represented by SEQ ID NO: 342

```
556-540  5'-agagcctgttccgtctc-3'     (SEQ ID NO: 378)

567-584  5'-gtggaggccgacatcaac-3'    (SEQ ID NO: 379)
```

-continued

```
841-824  5'-caggcttcagcatccttc-3'       (SEQ ID NO: 380)
916-900  5'-tcggacctgctcatctg-3'        (SEQ ID NO: 381)
925-908  5'-tcagtaacctcggacctg-3'       (SEQ ID NO: 382)
923-907  5'-agtaacctcggacctgc-3'        (SEQ ID NO: 383)
921-905  5'-taacctcggacctgctc-3'        (SEQ ID NO: 384)
```

Loof F: Regions on complementary strand of base sequence represented by SEQ ID NO: 342

```
395-381  5'-aggccctgcttctg-3'           (SEQ ID NO: 385)
393-379  5'-gccctgcttctggt-3'           (SEQ ID NO: 386)
392-376  5'-ccctgcttctggtacc-3'         (SEQ ID NO: 387)
392-375  5'-ccctgcttctggtacca-3'        (SEQ ID NO: 388)
393-376  5'-gccctgcttctggtacc-3'        (SEQ ID NO: 389)
395-380  5'-aggccctgcttctgg-3'          (SEQ ID NO: 390)
394-379  5'-ggccctgcttctggt-3'          (SEQ ID NO: 391)
457-440  5'-agaatcttgtcccgcagg-3'       (SEQ ID NO: 392)
456-440  5'-gaatcttgtcccgcagg-3'        (SEQ ID NO: 393)
699-680  5'-tgatttcctcctcatggttc-3'     (SEQ ID NO: 394)
698-679  5'-gatttcctcctcatggttct-3'     (SEQ ID NO: 395)
694-676  5'-tcctcctcatggttcttct-3'      (SEQ ID NO: 396)
734-318  5'-actgacctggcctccca-3'        (SEQ ID NO: 397)
724-710  5'-cctcccacttggccc-3'          (SEQ ID NO: 398)
```

Loop R: Regions on complementary strand of base sequence represented by SEQ ID NO: 342

```
493-510  5'-agatcgacaacgcccgtc-3'       (SEQ ID NO: 399)
495-512  5'-atcgacaacgcccgtctg-3'       (SEQ ID NO: 400)
495-509  5'-atcgacaacgcccgt-3'          (SEQ ID NO: 401)
496-509  5'-tcgacaacgcccgt-3'           (SEQ ID NO: 402)
506-520  5'-ccgtctggctgcaga-3'          (SEQ ID NO: 403)
507-520  5'-cgtctggctgcagatga-3'        (SEQ ID NO: 404)
508-525  5'-gtctggctgcagatgact-3'       (SEQ ID NO: 405)
509-526  5'-tctggctgcagatgactt-3'       (SEQ ID NO: 406)
752-767  5'-tccgggcaccgatctc-3'         (SEQ ID NO: 407)
756-771  5'-ggcaccgatctcgcca-3'         (SEQ ID NO: 408)
755-769  5'-gggcaccgatctcgc-3'          (SEQ ID NO: 409)
757-771  5'-gcaccgatctcgcca-3'          (SEQ ID NO: 410)
805-822  5'-tcatggccgagcagaacc-3'       (SEQ ID NO: 411)
806-821  5'-catggccgagcagaac-3'         (SEQ ID NO: 412)
```

Example 2-2

Designing of Primer for Detecting CK19

From the sequences of the regions selected in Example 2-1, the following primers for nucleic acid amplification to be applied to the LAMP method were obtained.

Each primer is shown in a primer set to be used in the RT-LAMP method of the present invention, and classified into four Groups A to D depending on the region. Each primer belonging to Group A is selected from a region of base position 270-560 in the base sequence represented by SEQ ID NO: 342 and a region of complementary strand thereof; likewise each primer belonging to Group B is selected from a region of base position 370-585 and a region of complementary strand thereof; likewise each primer belonging to Group C is selected from a region of base position 625-854 and a region of complementary strand thereof; and likewise each primer belonging to Group D is selected from a region of base position 655-930 and a region of complementary strand thereof.

(Group A)

```
FIP: Base Sequences of Regions F1c and F2 Coupled
FA-401  5'-tgtagtagtggctgtagtcgcgagctagaggtgaagatccg-3'    (SEQ ID NO: 413)

(Base sequences of SEQ ID NO: 343 and SEQ ID NO: 351 are coupled)
FA-403  5'-tgtagtagtggctgtagtcgcgagatccgcgactggtac-3'     (SEQ ID NO: 414)

(Base sequences of SEQ ID NO: 343 and SEQ ID NO: 352 are coupled)
FA-404  5'-tcgtgtagtagtggctgtagtcgagctagaggtgaagatccg-3'  (SEQ ID NO: 415)

(Base sequences of SEQ ID NO: 344 and SEQ ID NO: 351 are coupled)
FA-405  5'-tcgtgtagtagtggctgtagtcggtgaagatccgcgactg-3'    (SEQ ID NO: 416)

(Base sequences of SEQ ID NO: 344 and SEQ ID NO: 353 are coupled)
FA-406  5'-tcgtgtagtagtggctgtagtcgagatccgcgactggtac-3'    (SEQ ID NO: 417)

(Base sequences of SEQ ID NO: 344 and SEQ ID NO: 352 are coupled)
RIP: Base Sequences of Regions R1c and R2 Coupled RA-401  5'-gtgccaccattgagaactccggttcggaagtcatctgc-3'      (SEQ ID NO: 418)
(Base sequences of SEQ ID NO: 362 and SEQ ID NO: 369 are coupled)

F3 primer: (identical sequence with base sequence of F3 region)
F3-401  5'-gctaaccatgcagaacctc-3'                         (SEQ ID NO: 357)

R3 primer: (identical sequence with base sequence of R3 region)
R3-401  5'-agagcctgttccgtctc-3'                           (SEQ ID NO: 378)
```

-continued

Loop primer: (identical sequence with base sequence of loop F region or loop R)

```
LPF-401  5'-aggcccctgcttctg-3'                          (SEQ ID NO: 385)

LPF-402  5'-gccctgcttctggt-3'                           (SEQ ID NO: 386)

LPF-403  5'-ccctgcttctggtacc-3'                         (SEQ ID NO: 387)

LPF-404  5'-ccctgcttctggtacca-3'                        (SEQ ID NO: 388)

LPF-405  5'-gccctgcttctggtacc-3'                        (SEQ ID NO: 389)

LPF-406  5'-aggcccctgcttctgg-3'                         (SEQ ID NO: 390)

LPF-407  5'-ggccctgcttctggt-3'                          (SEQ ID NO: 391)

LPR-401  5'-agatcgacaacgcccgtc-3'                       (SEQ ID NO: 399)

LPR-402  5'-atcgacaacgcccgtctg-3'                       (SEQ ID NO: 400)

LPR-403  5'-atcgacaacgcccgt-3'                          (SEQ ID NO: 401)

LPR-404  5'-tcgacaacgcccgt-3'                           (SEQ ID NO: 402)
```

(Group B)

FIP: Base Sequences of Regions F1c and F2 Coupled
```
FA1-EK   5'-ggagttctcaatggtggcaccaactactacacgaccatccagg-3'  (SEQ ID NO: 419)
```

(Base sequences of SEQ ID NO: 345 and SEQ ID NO: 354 are coupled)
RIP: Base Sequences of Regions R1c and R2 Coupled
```
RA2-EK   5'-tgtcctgcagatcgacaacgccgtctcaaacttggttcgga-3'    (SEQ ID NO: 420)
```

(Base sequences of SEQ ID NO: 363 and SEQ ID NO: 370 are coupled)
```
RA6-EK   5'-gtcctgcagatcgacaacgcctccgtctcaaacttggttcg-3'    (SEQ ID NO: 421)
```

(Base sequences of SEQ ID NO: 364 and SEQ ID NO: 371 are coupled)
F3 primer: (identical sequence with base sequence of F3 region)
```
F3-EK    5'-tggtaccagaagcagggg-3'                      (SEQ ID NO: 358)
```

R3 primer: (identical sequence with base sequence of R3 region)
```
R3-EK    5'-gtggaggccgacatcaac-3'                      (SEQ ID NO: 379)
```

Loop primer: (identical sequence with base sequence of loop F region or loop R)
```
LPF1-EK  5'-agaatcttgtcccgcagg-3'                      (SEQ ID NO: 392)

LPF2-EK  5'-gaatcttgtcccgcagg-3'                       (SEQ ID NO: 393)

LPR1-EK  5'-ccgtctggctgcaga-3'                         (SEQ ID NO: 403)

LPR2-EK  5'-cgtctggctgcagatga-3'                       (SEQ ID NO: 404)

LPR3-EK  5'-gtctggctgcagatgact-3'                      (SEQ ID NO: 405)

LPR4-EK  5'-tctggctgcagatgactt-3'                      (SEQ ID NO: 406)
```

(Group C)

FIP: Base Sequences of Regions F1c and F2 Coupled
```
FA-1101  5'-ttggcccctcagcgtacaagagctggcctacctg-3'      (SEQ ID NO: 422)
```

(Base sequences of SEQ ID NO: 346 and SEQ ID NO: 355 are coupled)
RIP: Base Sequences of Regions R1c and R2 Coupled
```
RA-1101  5'-aggtcagtgtggaggtggcgcatgtcactcaggatc-3'    (SEQ ID NO: 423)
```

(Base sequences of SEQ ID NO: 365 and SEQ ID NO: 372 are coupled)
F3 primer: (identical sequence with base sequence of F3 region)
```
F3-1101  5'-acctggagatgcagatcg-3'                      (SEQ ID NO: 359)
```

R3 primer: (identical sequence with base sequence of R3 region)
```
R3-1101  5'-caggcttcagcatccttc-3'                     (SEQ ID NO: 380)
```

Loop primer: (identical sequence with base sequence of loop F region or loop R)
```
LPF-1100 5'-tgatttcctcctcatggttc-3'                   (SEQ ID NO: 394)
```

-continued

```
LPF-1102 5'-gatttcctcctcatggttct-3'              (SEQ ID NO: 395)

LPF-1103 5'-tcctcctcatggttcttct-3'              (SEQ ID NO: 396)

LPR-1101 5'-tccgggcaccgatctc-3'                 (SEQ ID NO: 407)

LPR-1102 5'-ggcaccgatctcgcca-3'                 (SEQ ID NO: 408)

LPR-1103 5'-gggcaccgatctcgc-3'                  (SEQ ID NO: 409)

LPR-1104 5'-gcaccgatctcgcca-3'                  (SEQ ID NO: 410)
```

(Group D)

```
FIP: Base Sequences of Regions F1c and F2 Coupled
FA-601 5'-agcggaatccacctccacgaggaaatcagtacgctgag-3'    (SEQ ID NO: 424)

(Base sequences of SEQ ID NO: 347 and SEQ ID NO: 356 are coupled)
FA-602 5'-aatccacctccacactgaccgaggaaatcagtacgctgag-3'  (SEQ ID NO: 425)

(Base sequences of SEQ ID NO: 348 and SEQ ID NO: 356 are coupled)
FA-603 5'-atccacctccacactgaccgaggaaatcagtacgctgag-3'   (SEQ ID NO: 426)

Base sequences of SEQ ID NO: 349 and SEQ ID NO: 359 are coupled)
FA-604 5'-tccacctccacactgaccgaggaaatcagtacgctgag-3'    (SEQ ID NO: 427)

(Base sequences of SEQ ID NO: 350 and SEQ ID NO: 356 are coupled)
RIP: Base Sequences of Regions R1c and R2 Coupled
RA-601 5'-tctcgccaagatcctgagtgcaggcttcagcatccttc-3'    (SEQ ID NO: 428)

(Base sequences of SEQ ID NO: 366 and SEQ ID NO: 373 are coupled)
RA-602 5'-tctcgccaagatcctgagtgggtgaaccaggcttcag-3'     (SEQ ID NO: 429)

(Base sequences of SEQ ID NO: 366 and SEQ ID NO: 374 are coupled)
RA-603 5'-tctcgccaagatcctgagtggtgaaccaggcttcagc-3'     (SEQ ID NO: 430)

(Base sequences of SEQ ID NO: 366 and SEQ ID NO: 375 are coupled)
RA-604 5'-tctcgccaagatcctgagtggaaccaggcttcagcatc-3'    (SEQ ID NO: 431)

(Base sequences of SEQ ID NO: 366 and SEQ ID NO: 376 are coupled)
RA-605 5'-tctcgccaagatcctgagtgaccaggcttcagcatcc-3'     (SEQ ID NO: 432)

(Base sequences of SEQ ID NO: 366 and SEQ ID NO: 377 are coupled)
RA-606 5'-tcgccaagatcctgagtgaccaggcttcagcatccttc-3'    (SEQ ID NO: 433)

(Base sequences of SEQ ID NO: 367 and SEQ ID NO: 373 are coupled)
RA-607 5'-agatcctgagtgacatgcgaagcaggcttcagcatccttc-3'  (SEQ ID NO: 434)

(Base sequences of SEQ ID NO: 368 and SEQ ID NO: 373 are coupled)
F3 primer: (identical sequence with base sequence of F3 region)
F3-601 5'-aaagagctggcctacctg-3'                (SEQ ID NO: 360)

F3-602 5'-agctggcctacctgaag-3'                 (SEQ ID NO: 361)

R3 primer: (identical sequence with base sequence of R3 region)
R3-601 5'-tcggacctgctcatctg-3'                 (SEQ ID NO: 381)

R3-602 5'-tcagtaacctcggacctg-3'                (SEQ ID NO: 382)

R3-603 5'-agtaacctcggacctgc-3'                 (SEQ ID NO: 383)

R3-604 5'-taacctcggacctgctc-3'                 (SEQ ID NO: 384)

Loop primer: (identical sequence with base sequence of loop F region or
loop R)
LPF-     5'-actgacctggcctccca-3'               (SEQ ID NO: 397)
601

LPF-     5'-cctcccacttggccc-3'                 (SEQ ID NO: 398)
602

LPR-     5'-tcatggccgagcagaacc-3'              (SEQ ID NO: 411)
601

LPR-     5'-catggccgagcagaac-3'                (SEQ ID NO: 412)
602
```

Example 3-1

Selection of Region from Human CK20 Base Sequence

The base sequence of human CK20 represented by SEQ ID NO: 435 was searched for positions of appropriate regions for the LAMP method using a probe designing software. As a result of selecting regions according to the criteria that Tm 58.5-63.5° C. for F1c and R1c, Tm 61.5-62.5° C. for F2 and R2, Tm 58.5-62.5° C. for F3 and R3, the regions as shown below are selected. The selected regions are included in a region of base position 340-1050 of the base sequence represented by SEQ ID NO: 435 and a complementary strand region thereof.

F1c: Regions on complementary strand of base sequence represented by SEQ ID NO: 435

```
920-900
5'-ttcatgctgagatgggactgg-3'       (SEQ ID NO: 436)

915-895
5'-gctgagatgggactggagttc-3'       (SEQ ID NO: 437)

436-416
5'-caatttgcaggacacaccgag-3'       (SEQ ID NO: 438)
```

F2: Regions on base sequence represented by SEQ ID NO: 435

```
847-865  5'-gaggttcaactaacggagc-3'   (SEQ ID NO: 439)

850-869  5'-gttcaactaacggagctgag-3'  (SEQ ID NO: 440)

855-872  5'-actaacggagctgagacg-3'    (SEQ ID NO: 441)

370-388  5'-attgaagagctgcgaagtc-3'   (SEQ ID NO: 442)
```

F3: Regions on base sequence represented by SEQ ID NO: 435

```
345-367
5'-cgactacagtgcatattacagac-3'      (SEQ ID NO: 443)

805-822
5'-cagcaacaggtcacagtg-3'           (SEQ ID NO: 444)
```

R1c: Regions on base sequence represented by SEQ ID NO: 435

```
940-958
5'-ctagaggagaccaaggccc-3'          (SEQ ID NO: 445)

939-958
5'-tctagaggagaccaaggccc-3'         (SEQ ID NO: 446)

947-966
5'-agaccaaggcccgttacagc-3'         (SEQ ID NO: 447)

452-472
5'-ctgctgaggacttcagactga-3'        (SEQ ID NO: 448)
```

R2: Regions on complementary strand of base sequence represented by SEQ ID NO: 435

```
1004-987 5'-agagagctcaacagcgac-3'    (SEQ ID NO: 449)

1007-990 5'-tccagagagctcaacagc-3'    (SEQ ID NO: 450)

994-978  5'-acagcgactggaggttg-3'     (SEQ ID NO: 451)

1000-984 5'-agctcaacagcgactgg-3'     (SEQ ID NO: 452)

523-505  5'-cttggagatcagcttccac-3'   (SEQ ID NO: 453)
```

R3: Regions on complementary strand of base sequence represented by SEQ ID NO: 435

```
556-535
5'-gtagggttaggtcatcaaagac-3'       (SEQ ID NO: 454)

1044-1027
5'-gcgttccatgttactccg-3'           (SEQ ID NO: 455)
```

Loof F: Regions on complementary strand of base sequence represented by SEQ ID NO: 435

```
409-389
5'-gcagttgagcatccttaatct-3'        (SEQ ID NO: 456)

891-875
5'-ctcaaggctctgggagg-3'            (SEQ ID NO: 457)
```

Loop R: Regions on base sequence represented by SEQ ID NO: 435

```
480-499  5'-gactgagagaggaatacgtc-3'  (SEQ ID NO: 458)

968-985  5'-gccagttagccaacctcc-3'    (SEQ ID NO: 459)

970-985  5'-cagttagccaacctcc-3'      (SEQ ID NO: 460)
```

Example 3-2

Designing of Primer for Detecting CK20

From the sequences of the regions selected in Example 3-1, the following primers for nucleic acid amplification to be applied to the LAMP method were obtained.

FIP: Base Sequences of Regions F1c and F2 Coupled

```
KFA-5   5'-ttcatgctgagatgggactgggaggttcaactaacggagc-3'      (SEQ ID NO: 461)

(Base sequences of SEQ ID NO: 436 and SEQ ID NO: 439 are coupled)
KFA-5a  5'-ttcatgctgagatgggactgggttcaactaacggagctgag-3'     (SEQ ID NO: 462)

(Base sequences of SEQ ID NO: 436 and SEQ ID NO: 440 are coupled)
KFA-5b  5'-ttcatgctgagatgggactggactaacggagctgagacg-3'       (SEQ ID NO: 463)

(Base sequences of SEQ ID NO: 436 and SEQ ID NO: 441 are coupled)
KFA-5d  5'-gctgagatgggactggagttcgaggttcaactaacggagc-3'      (SEQ ID NO: 464)

(Base sequences of SEQ ID NO: 437 and SEQ ID NO: 439 are coupled)
KFA-5e   5'-gctgagatgggactggagttcgttcaactaacggagctgag-3'    (SEQ ID NO: 465)
```

-continued (Base sequences of SEQ ID NO: 437 and SEQ ID NO: 440 are coupled)
KFA-5f 5'-gctgagatgggactggagttcactaacggagctgagacg-3'    (SEQ ID NO: 466)

(Base sequences of SEQ ID NO: 437 and SEQ ID NO: 441 are coupled)
AFA    5'-caatttgcaggacacaccgagattgaagagctgcgaagtc-3'    (SEQ ID NO: 467)

(Base sequences of SEQ ID NO: 438 and SEQ ID NO: 442 are coupled)
RIP: Base Sequences of Regions R1c and R2 Coupled RIP: Base Sequences of Regions R1c and R2 Coupled KRA-5  5'-ctagaggagaccaaggcccagagagctcaacagcgac-3'    (SEQ ID NO: 468)

(Base sequences of SEQ ID NO: 445 and SEQ ID NO: 449 are coupled)
KRA-5a 5'-tctagaggagaccaaggccctccagagagctcaacagc-3'   (SEQ ID NO: 469)

(Base sequences of SEQ ID NO: 446 and SEQ ID NO: 450 are coupled)
KRA-5c 5'-tctagaggagaccaaggcccacagcgactggaggttg-3'    (SEQ ID NO: 470)

(Base sequences of SEQ ID NO: 446 and SEQ ID NO: 451 are coupled)
KRA-5d 5'-agaccaaggcccgttacagcagagagctcaacagcgac-3'   (SEQ ID NO: 471)

(Base sequences of SEQ ID NO: 447 and SEQ ID NO: 449 are coupled)
KRA-5e 5'-agaccaaggcccgttacagctccagagagctcaacagc-3'   (SEQ ID NO: 472)

(Base sequences of SEQ ID NO: 447 and SEQ ID NO: 450 are coupled)
KRA-5f 5'-agac caaggcccgttacagcagctcaacagcgactgg-3'   (SEQ ID NO: 473)

(Base sequences of SEQ ID NO: 447 and SEQ ID NO: 452 are coupled)
ARAf   5'-ctgctgaggacttcagactgacttggagatcagcttccac-3'  (SEQ ID NO: 474)

(Base sequences of SEQ ID NO: 448 and SEQ ID NO: 453 are coupled)

F3 primer: (identical sequence with base sequence of F3 region)

AF3
5'-cgactacagtgcatattacagac-3'    (SEQ ID NO: 443)

KF3-5
5'-cagcaacaggtcacagtg-3'    (SEQ ID NO: 444)

R3 primer: (identical sequence with base sequence of R3 region)

AR3
5'-gtagggttaggtcatcaaagac-3'    (SEQ ID NO: 454)

KR3-5
5'-gcgttccatgttactccg-3'    (SEQ ID NO: 455)

Loop primer: (identical sequence with base sequence of loop F region or loop R)

LPF2
5'-gcagttgagcatccttaatct-3'    (SEQ ID NO: 456)

K-LPF2
5'-ctcaaggctctgggagg-3'    (SEQ ID NO: 457)

LPR6
5'-gactgagagaggaatacgtc-3'    (SEQ ID NO: 458)

K-LPR1
5'-gccagttagccaacctcc-3'    (SEQ ID NO: 459)

K-LPR2
5'-cagttagccaacctcc-3'    (SEQ ID NO: 460)

TEST EXAMPLES

Effects obtained when the RT-LAMP method is executed using different primers for detecting CK18, CK19 or CK20 obtained above were measured and determined according to the Test examples 1 to 3.

Test Example 1-1

Observation of Amplification

This test was conducted in order to examine the time required from starting of the reaction until amplification could be observed in each case the measurement was conducted by RT-LAMP method using the following combination of various primers for detecting human CK18.

1) Method for Preparing Human CK18RNA Sample

By conducting RT-PCR using a primer designed based on a base sequence of human CK18, human CK18cDNA was isolated from total RNA derived from KATOIII (stomach cancer cell). From human CK18cDNA cloned into pBluescript (plasmid manufactured by STRATAGENE), a transcription product was synthesized using in vitro transcription system (Riboprobe in vitro transcription system (manufactured by Promega)). RNA concentration of the undiluted solution thus obtained was determined by measuring absorbance at 260 nm, and based on the result, the solution was diluted in 50 ng/μl yeast RNA (manufactured by Ambion) so that the copy numbers of RNA of human CK18 were 60000, 6000, 600, 60, 6 and 0 (control), which were used as template solutions.

2) Primer Set for Detecting Human CK18

A variety of primers were used in the combinations as shown in Table 1.

TABLE 1

| Primer set | I | II | III | IV |
|---|---|---|---|---|
| FIP | 234 | 252 | 259 | 278 |
| RIP | 287 | 297 | 307 | 332 |
| F3 primer | 66 | 68 | 72 | 79 |
| R3 primer | 179 | 182 | 184 | 193 |
| Loop primer (loop F) | 203 | 211 | 212 | 214 |
| Loop primer (loop R) | 220 | 223 | 226 | 228 |

(Each number represents SEQ ID number, and each primer means a primer comprising a sequence represented by each SEQ ID number.)

3) Composition of Reaction Solution

| | |
|---|---|
| dNTPs (manufactured by GIBCO) | 0.4 mM |
| MgSO$_4$ | 2 mM |
| Dithiothreitol | 5 mM |
| Betaine (manufactured by Sigma) | 640 mM |
| Thermopol buffer (manufactured by New England BioLabs) | |
| AMV reverse transcriptase (manufactured by Promega) | 1.25 U |
| Bst DNA polymerase (manufactured by New England BioLabs) | 16 U |
| Ethidium bromide | 0.125 mg/mL |
| Primer | |
| FIP 40 pmol, RIP 40 pmol, F3 primer 5 pmol, R3 primer 5 pmol, Loop primer (loop F, loop R) | each 20 pmol |

4) RT-LAMP Method

To 23 μl of reaction solution containing the above six kinds of primers, 2 μl of RNA sample of human CK18 was added, and heated at 65° C. for one hour.

5) Observation of Amplification

Since the amplified product has a double-strand structure, ethidium bromide intercalates into the double-strand structure to emit fluorescent. Increase in fluorescence intensity (Rn) was measured in real time by using PRISM 7700 manufactured by ABI.

6) Results

Results of the cases where Primer sets I to IV were respectively used are shown in FIGS. 1 to 4. These results show that the larger the amount of the template of human CK18, the shorter the time required until amplification can be observed in every set. In Primer sets I and III, amplification was observed in 20 minutes even in the case of 600 copies, while in Primer set II, amplification was observed after about 20 minutes in the case of 6000 copies. As for Primer set IV, amplification was observed after about 20 minutes in the case of 6000 copies, and after about 30 minutes even in the case of 600 copies.

Test Example 1-2

Effect of Loop Primer

Among Primer sets considered in Test example 1-1, Primer set I in which the time required for observation of amplification was shortest was selected, and a test was made in order to examine the sensitivity in presence/absence of a loop primer.

1) Method for Preparing Human CK18RNA Sample

Samples having copy numbers of 60000, 6000, 600 and 0 (control) were prepared in a similar manner as described in Test example 1-1.

2) Primer Set

Primer set I shown in Table 1, and a primer set excluding each loop primer from Primer set I were used.

3) Composition of Reaction Solution

A reaction solution similar to that of Test example 1-1 was used, and as to the set excluding loop primer, any loop primer was not added.

4) RT-LAMP Method

To 23 μl of reaction solution containing six or four kinds of primers, 2 μl of RNA sample of human CK18 was added, and heated at 65° C. for one hour.

5) Observation of Amplification

Measurement was conducted in real time in a similar manner with Test example 1-1.

6) Results

Figure 5:
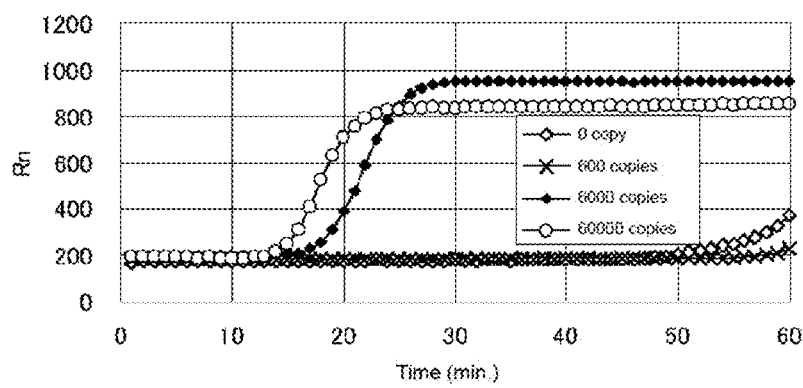
FIG. 5 is a view showing results of LAMP conducted by using Primer set I (with loop primers) of human CK18 (Test example 1-2)
Figure 6:
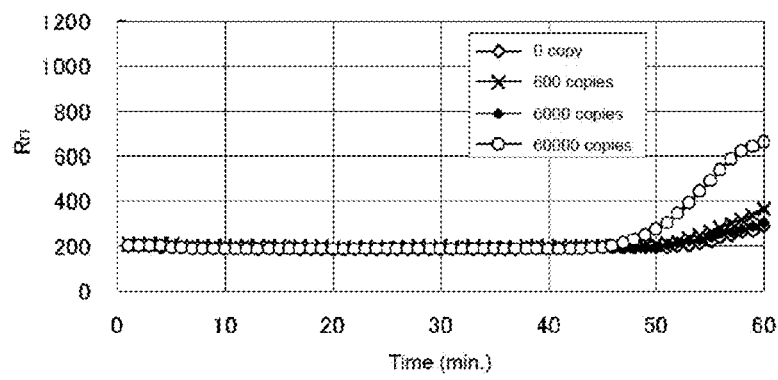
FIG. 6 is a view showing results of LAMP conducted by using Primer set I (without loop primers) of human CK18 (Test example 1-2)

Results of determination are shown in FIGS. 5 and 6. These results show that the time required until amplification can be observed was shorter in the case where a loop primer was not used. However, even in the case where a loop primer was used, amplification of human CK18 was observed after about 50 minutes even in the case of 60000 copies.

Example 1-3

Amplification Specificity to Human CK18

Amplification specificity to human CK18 when measurement was conducted using Primer set I was examined. It is known that cytokeratins (CK) have isoforms such as human CK19, 20 and the like besides human CK18. These isoforms comprises a base sequence having about 60% homology with human CK18. This test was conducted for determining whether human CK18 could be tested distinguishably from human CK19 or 20 when measurement was conducted by using the above primer sets.

1) Method for Preparing RNA Sample

An RNA sample of human CK18 having a copy number of 60000 was prepared in a similar manner as described in Test example 1-1. Also with regard to RNAs of human CK19 and human CK20, samples were prepared in a similar manner.

2) Primer Set

Primer set I shown in Table 1 was used.

3) Composition of Reaction Solution

A reaction solution similar to that of Test example 1-1 was used.

4) RT-LAMP Method

The similar condition as described in Test example 1 was used.

5) Observation of Amplification

Measurement was conducted in real time in a similar manner with Test example 1-1.

6) Results

Figure 7:
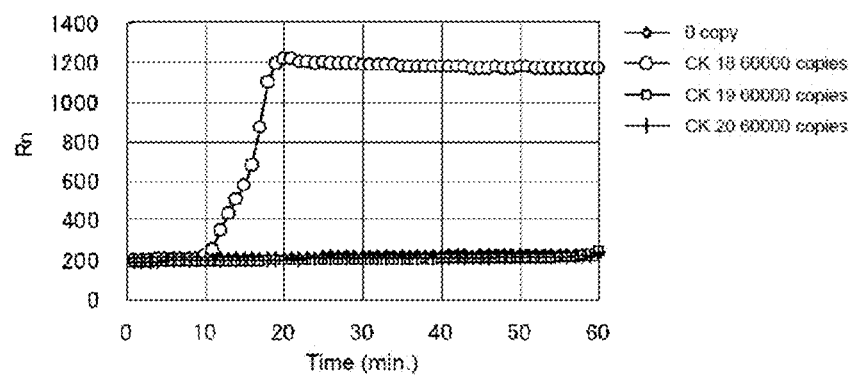
FIG. 7 shows amplification specificity when LAMP is conducted using Primer set I of human CK18 (Test example 1-3)
Figure 8:
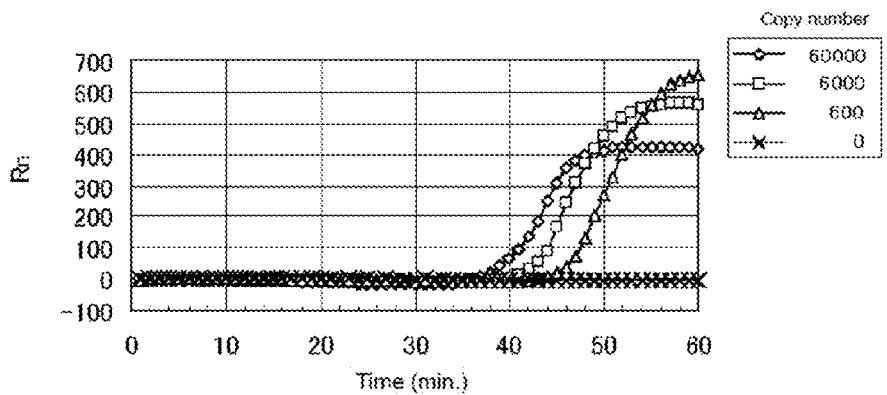
FIG. 8 is a view showing results of LAMP conducted by using Primer set A (without loop primers) of human CK19 (Test example 2-1)
Figure 9:
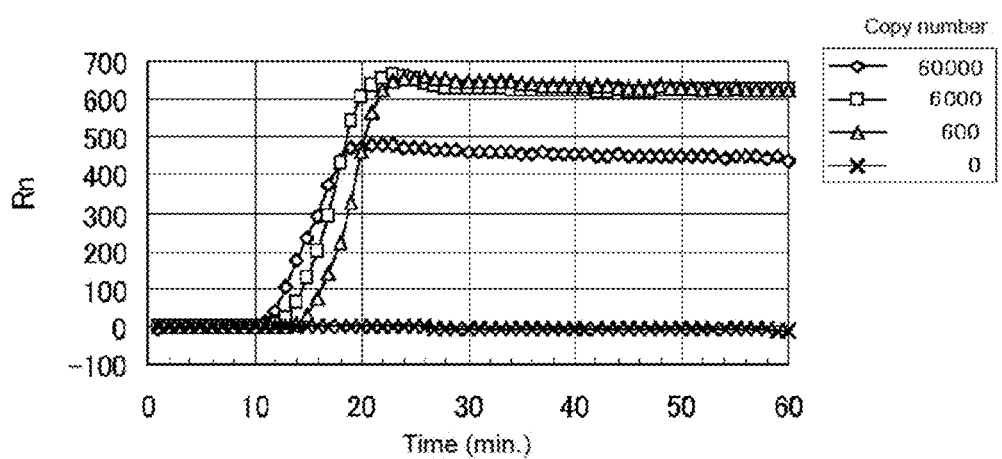
FIG. 9 is a view showing results of LAMP conducted by using Primer set A (without loop primers) of human CK19 (Test example 2-1)
Figure 10:
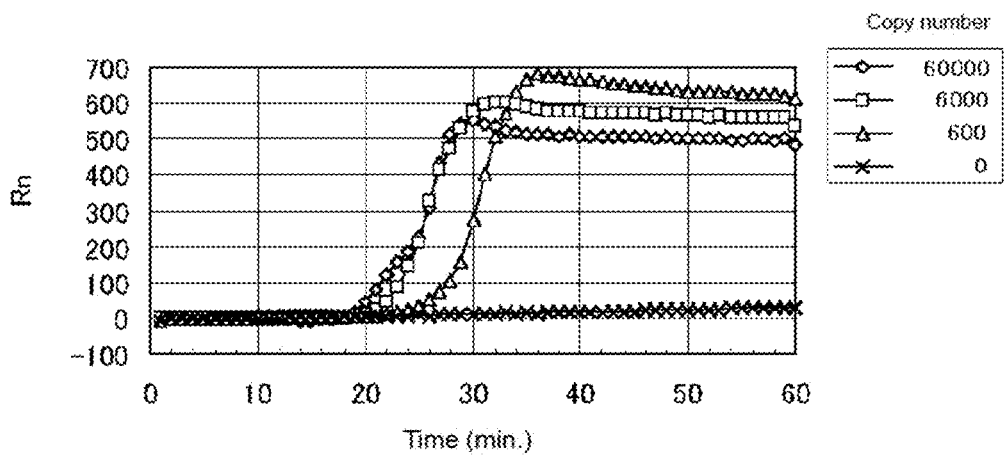
FIG. 10 is a view showing results of LAMP conducted by using Primer set A (with loop primers) of human CK19 (Test example 2-1)
Figure 11:
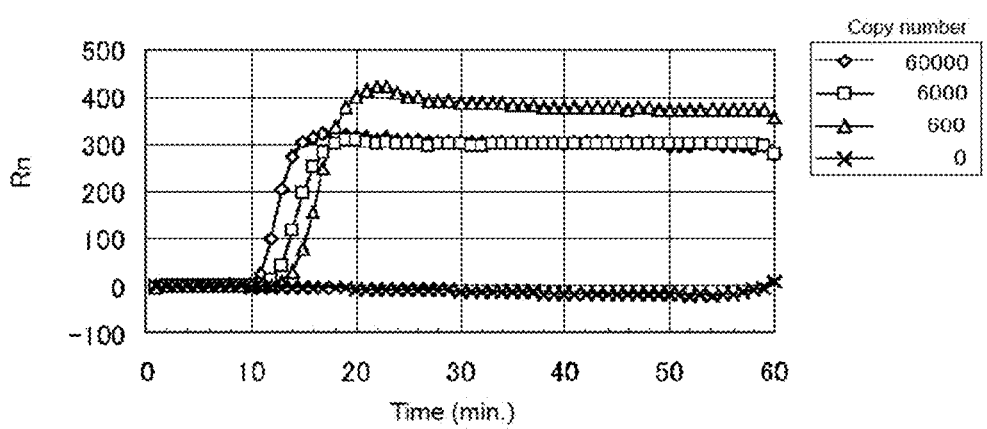
FIG. 11 is a view showing results of LAMP conducted by using Primer set A (with loop primers) of human CK19 (Test example 2-1)
Figure 12:
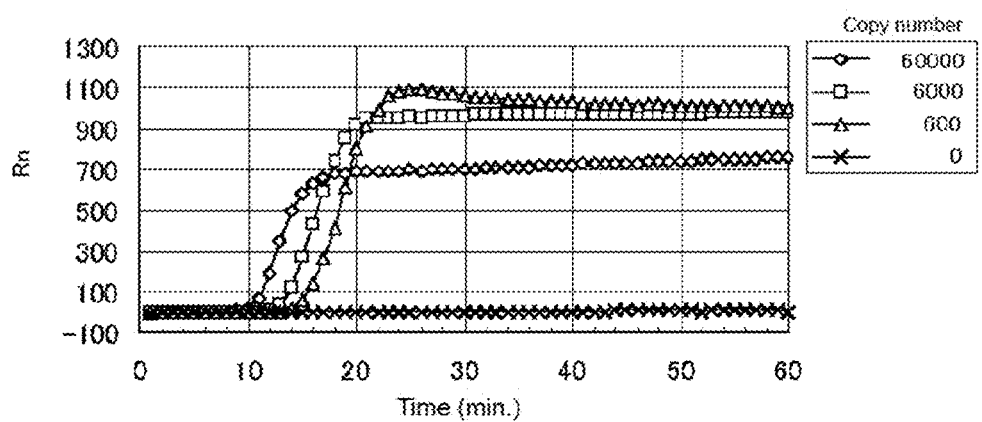
FIG. 12 is a view showing results of LAMP conducted by using Primer set A (with loop primers) of human CK19 (Test example 2-1)

Results are shown in FIG. 7. These results show that human CK18RNA, but absolutely not human CK19RNA and human CK20RNA are amplified when Primer set I was used, revealing specificity of Primer set I to human CK18RNA.

Test Example 2-1

Effect of Primer Sets (Group A) for Detecting Human CK19

This test was conducted in order to examine an amplification pattern when RNA of human CK19 was measured by the RT-LAMP method using a primer set selected from Group A shown in Example 2-2.

1) Primer Set (Group A)

Examination was carried out using a primer set consisting of FIP: FA-401 (SEQ ID NO: 413), RIP: RA-401 (SEQ ID NO: 418), F3: F3-401 (SEQ ID NO: 357), and R3: R3-401 (SEQ ID NO: 378), and a primer set in combination with various loop primers: LPF-401 (SEQ ID NO: 385) and LPR-401 (SEQ ID NO: 399), LPF-401 (SEQ ID NO: 385) and LPR-402 (SEQ ID NO: 400), LPF-401 (SEQ ID NO: 385) and LPR-403 (SEQ ID NO: 401), or LPF-401 (SEQ ID NO: 385) and LPR-404 (SEQ ID NO: 402).

2) Method for Preparing Human CK19RNA

By conducting RT-PCR using a primer designed based on a base sequence of human CK19, human CK19cDNA was isolated from total RNA derived from KATOIII (stomach cancer cell). From human CK19cDNA cloned into pBluescript (plasmid manufactured by STRATAGENE), a transcription product was synthesized using in vitro transcription system (Riboprobe in vitro transcription system (manufactured by Promega)). RNA concentration of the undiluted solution thus obtained was determined by measuring absorbance at 260 nm, and based on the result, the solution was diluted in 50 ng/µl yeast RNA (manufactured by Ambion) so that the copy number of RNA of human CK19 was 60000, 6000, 600, 60, 6 and 0 (control), which were used as template solutions.

3) Composition of Reaction Solution

A reaction solution similar to that of Test example 1-1 was used, and as to the set excluding loop primer, a loop primer was not added.

4) RT-LAMP Method

To 23 µl of reaction solution containing four kinds of primers not including loop primers or containing six kinds of primers including loop primers, 2 µl of RNA sample of human CK19 was added, and heated at 65° C. for one hour.

5) Observation of Amplification

Measurement was conducted in real time in a similar manner with Test example 1-1.

6) Results

Results obtained for the primer set not including loop primers and the primer set including various loop primers are shown in FIGS. 8 to 12. These results show that the time required until amplification can be observed was about 40 minutes after starting the test when loop primers are not used. On the other hand, as shown in FIGS. 9 to 12, in the case of the systems including loop primers, amplification could be observed at about between 10 minutes and 20 minutes.

Test Example 2-2

Effect of Primer Sets (Group C) for Detecting Human CK19

This test was conducted in order to examine an amplification pattern when RNA of human CK19 was measured by the RT-LAMP method using a primer set selected from Group A shown in Example 2-2.

1) Primer Set (Group C)

Examination was carried out using a primer set consisting of FIP: FA-1101 (SEQ ID NO: 422), RIP: RA-1101 (SEQ ID NO: 423), F3: F3-1101 (SEQ ID NO: 359) and R3: R3-1101 (SEQ ID NO: 380), and a primer set in combination with various loop primers: LPF-1101 (SEQ ID NO: 394) and LPR-1101 (SEQ ID NO: 407), LPF-1101 (SEQ ID NO: 394) and LPR-1102 (SEQ ID NO: 408), LPF-1101 (SEQ ID NO: 394) and LPR-1103 (SEQ ID NO: 409), LPF-1101 (SEQ ID NO: 394) and LPR-1104 (SEQ ID NO: 410), LPF-1102 (SEQ ID NO: 395) and LPR-1101 (SEQ ID NO: 407), or LPF-1103 (SEQ ID NO: 396) and LPR-1101 (SEQ ID NO: 407).

2) Preparation of Human CK19RNA Sample

Following the operation as shown in Test example 2-1, samples were prepared so that the copy numbers were 60000, 6000, 600, 60 and 0 (control), respectively.

3) Composition of Reaction Solution, 4) RT-LAMP Method and 5) Observation of Amplification were Conducted in a Similar Manner as Test Example 2-1.

6) Results

Figure 13:
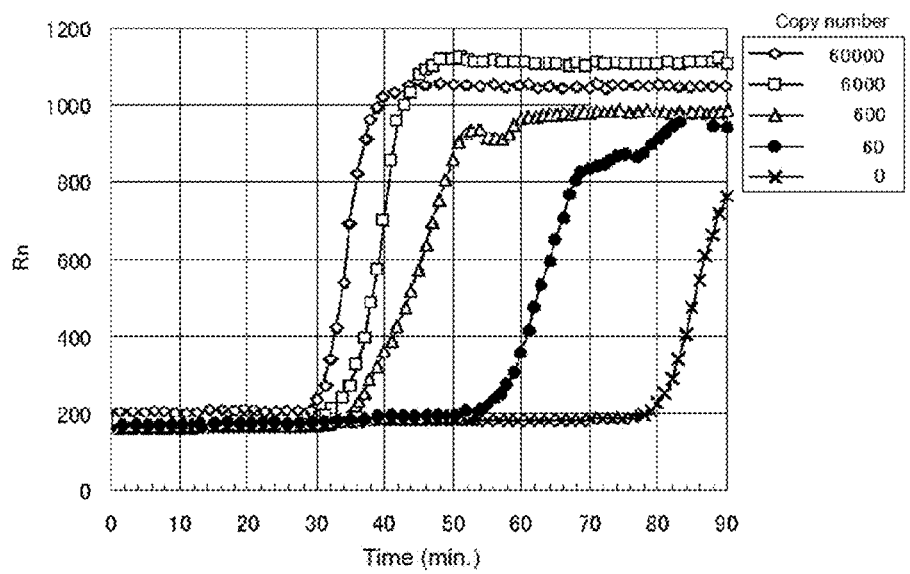
FIG. 13 is a view showing results of LAMP conducted by using Primer set C (without loop primers) of human CK19 (Test example 2-2)
Figure 14:
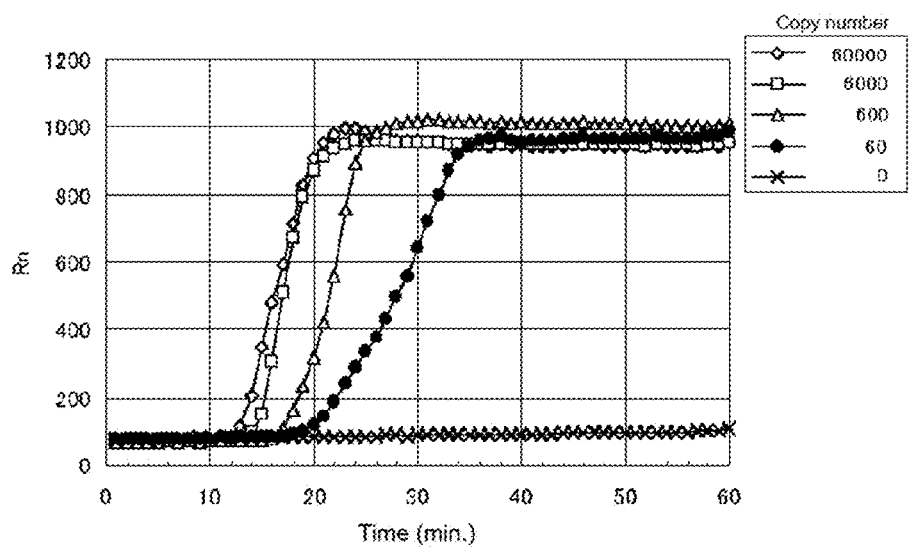
FIG. 14 is a view showing results of LAMP conducted by using Primer set C (with loop primers) of human CK19 (Test example 2-2)
Figure 15:
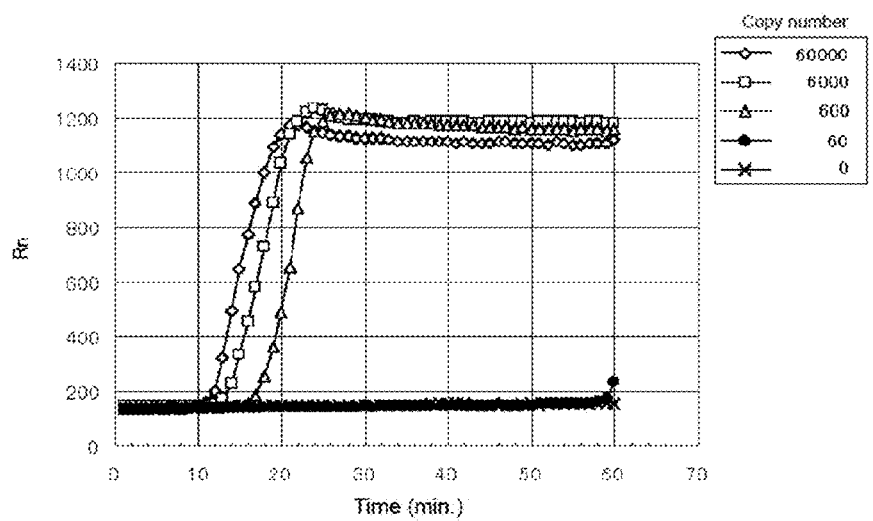
FIG. 15 is a view showing results of LAMP conducted by using Primer set C (with loop primers) of human CK19 (Test example 2-2)
Figure 16:
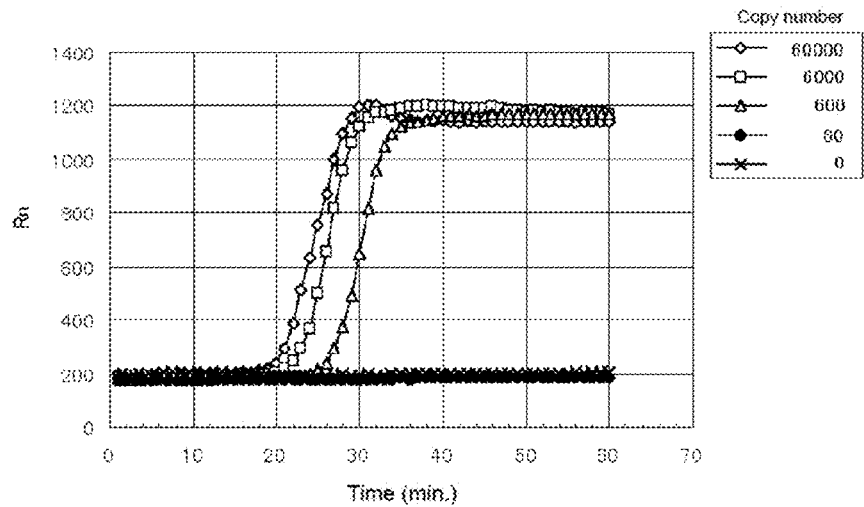
FIG. 16 is a view showing results of LAMP conducted by using Primer set C (with loop primers) of human CK19 (Test example 2-2)
Figure 17:
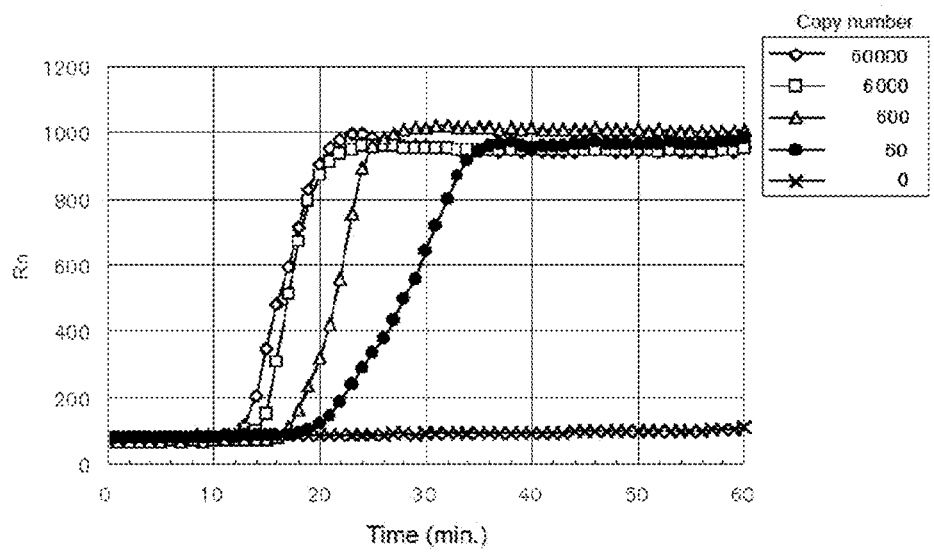
FIG. 17 is a view showing results of LAMP conducted by using Primer set C (with loop primers) of human CK19 (Test example 2-2)
Figure 18:
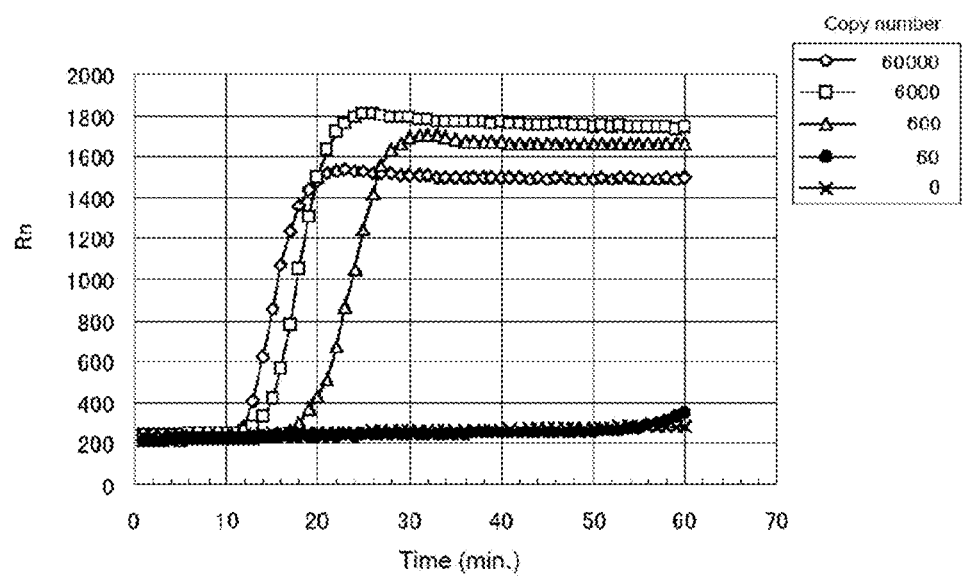
FIG. 18 is a view showing results of LAMP conducted by using Primer set C (with loop primers) of human CK19 (Test example 2-2)
Figure 19:
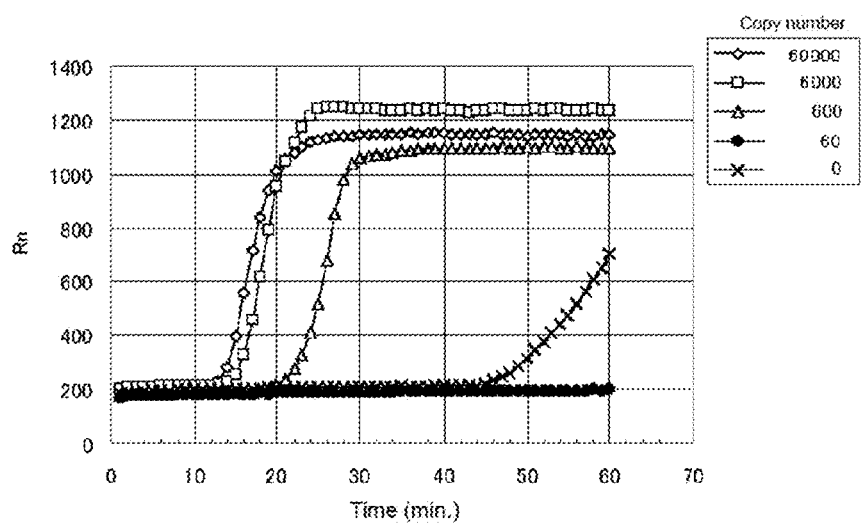
FIG. 19 is a view showing results of LAMP conducted by using Primer set C (with loop primers) of human CK19 (Test example 2-2)

Results obtained for the primer set not including loop primers and the primer set including various loop primers are shown in FIGS. 13 to 19. These results show that when loop primers are not used, the time required until amplification can be observed was about 30 minutes after starting the test (FIG. 13). On the other hand, in the systems using loop primers, amplification could be observed at about between 10 minutes and 20 minutes, when combined with LPF-1101 (SEQ ID NO: 394) and LPR-1101 (SEQ ID NO: 407) (FIG. 14), LPF-1101 (SEQ ID NO: 394) and LPR-1102 (SEQ ID NO: 408) (FIG. 15), LPF-1101 (SEQ ID NO: 394) and LPR-1104 (SEQ ID NO: 410) (FIG. 17), LPF-1102 (SEQ ID NO: 395) and LPR-1101 (SEQ ID NO: 407) (FIG. 18) or LPF-1103 (SEQ ID NO: 396) and LPR-1101 (SEQ ID NO: 407) (FIG. 19). When combined with LPF-1101 (SEQ ID NO: 394) and LPR-1103 (SEQ ID NO: 409) (FIG. 16), amplification could be observed at about 20 minutes Test Example 2-3

Effect of Primer Sets (Group D) for Detecting Human CK19

This test was conducted in order to examine an amplification pattern when RNA of human CK19 was measured by the RT-LAMP method using a primer set selected from Group D shown in Example 2-2.

1) Primer Set (Group D)

Examination was carried out using a primer set consisting of FIP: FA-601 (SEQ ID NO: 424), RIP: RA-604 (SEQ ID NO: 431), F3: F3-601 (SEQ ID NO: 360) and R3: R3-601 (SEQ ID NO: 381), and a primer set in combination with various loop primers: LPF-601 (SEQ ID NO: 397) and LPR-601 (SEQ ID NO: 411).

2) Preparation of Human CK19RNA Sample

Following the operation as shown in Test example 2-1, samples were prepared so that the copy numbers were 60000, 6000, 600, 60 and 0 (control), respectively.

3) Composition of Reaction Solution, 4) RT-LAMP Method and 5) Observation of Amplification were Conducted in a Similar Manner as Test Example 2-1.

6) Results

Figure 20:
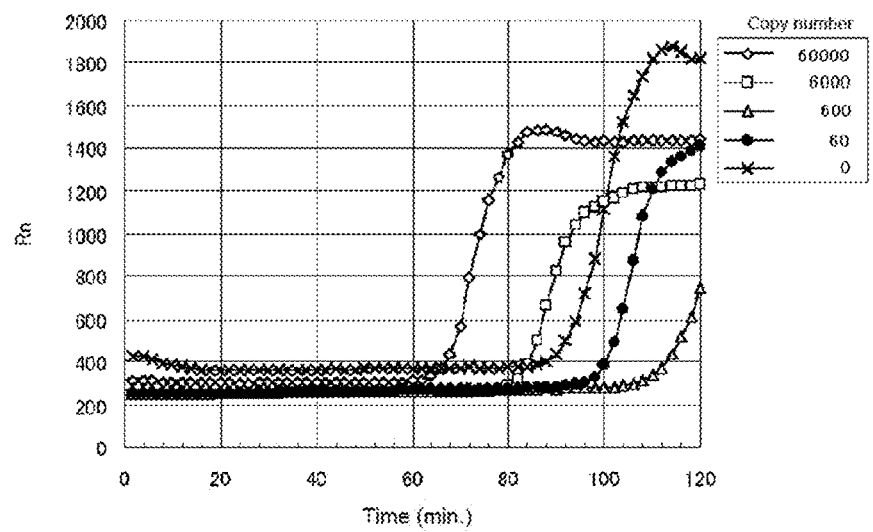
FIG. 20 is a view showing results of LAMP conducted by using Primer set D (without loop primers) of human CK19 (Test example 2-3)
Figure 21:
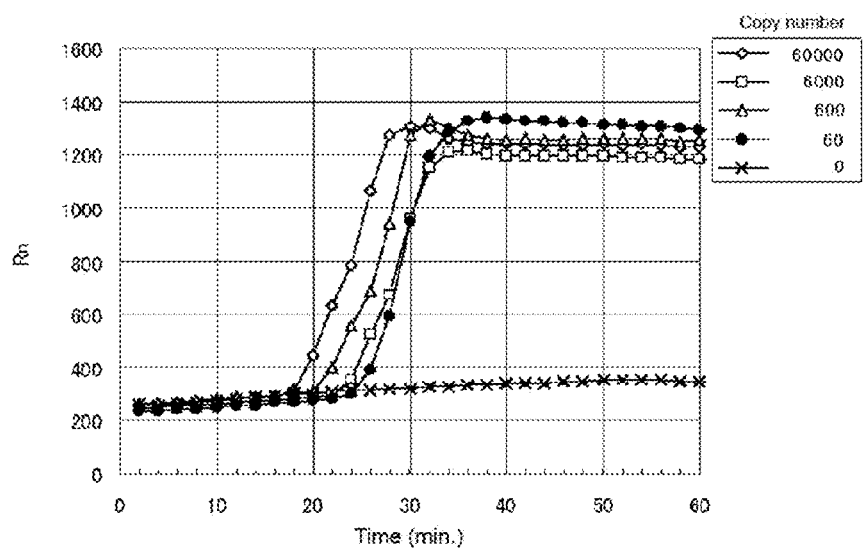
FIG. 21 is a view showing results of LAMP conducted by using Primer set D (with loop primers) of human CK19 (Test example 2-3)
Figure 22:
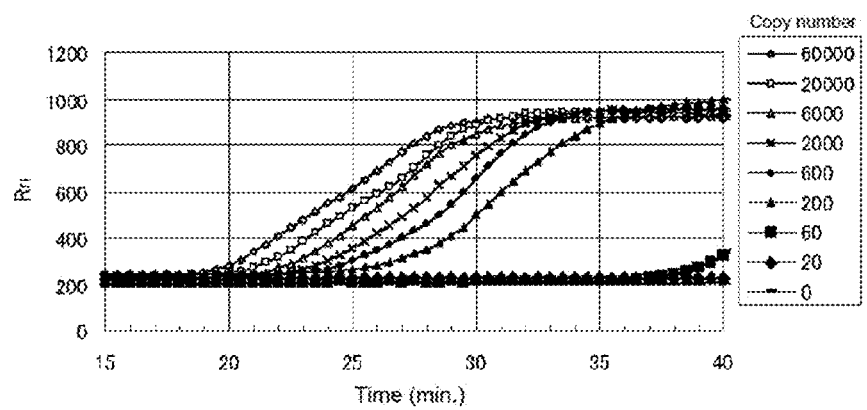
FIG. 22 is a view showing results of LAMP conducted by using Primer set A of human CK19 (Test example 2-4)
Figure 23:
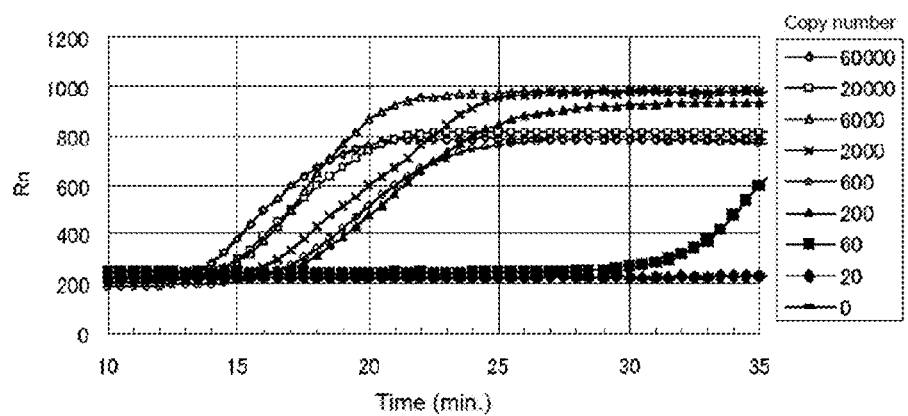
FIG. 23 is a view showing results of LAMP conducted by using Primer set B of human CK19 (Test example 2-4)
Figure 24:
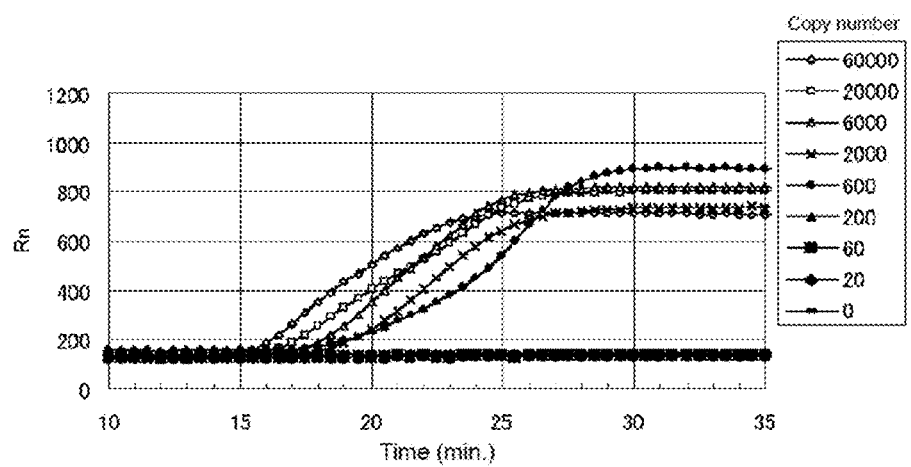
FIG. 24 is a view showing results of LAMP conducted by using Primer set C of human CK19 (Test example 2-4)

Results obtained for the primer set not including loop primers and the primer set including various loop primers are shown in FIG. 20 and FIG. 21, respectively. These results show that when loop primers are not used, the time required until amplification of nucleic acid can be observed was about 70 minutes. Additionally, even for the copy number of 0, non-specific amplification was observed, suggesting slightly low specificity. On the other hand, when loop primers were used, amplification could be observed at about 20 minutes, and non-specific amplification was not observed for the copy number of 0. Specificity was improved by the use of loop primers.

Test Example 2-4

Measurement Sensitivity

This test was conducted in order to examine the sensitivity of measurement for human CK19RNA when the measurement was conducted using each primer set selected from the Group A, C and D shown in Test examples 2-1 to 2-3, or a primer set selected from Group B.

A group: FIP: FA-401 (SEQ ID NO: 413), RIP: RA-401 (SEQ ID NO: 418), F3: F3-401 (SEQ ID NO: 357), R3: R3-401 (SEQ ID NO: 378),
Loop primer: LPF-401 (SEQ ID NO: 385), LPR-404 (SEQ ID NO: 402)

B group: FIP: FA1-EK (SEQ ID NO: 419), RIP: RA6-EK (SEQ ID NO: 421), F3: F3-EK (SEQ ID NO: 358), R3: R3-EK (SEQ ID NO: 379),
Loop primer: LPF1-EK (SEQ ID NO: 392), LPR2-EK (SEQ ID NO: 404)

C group: FIP: FA-1101 (SEQ ID NO: 422), RIP: RA-1101 (SEQ ID NO: 423), F3: F3-1101 (SEQ ID NO: 359), R3: R3-1101 (SEQ ID NO: 380),
Loop primer: LPF-1101 (SEQ ID NO: 394), LPR-1101 (SEQ ID NO: 407)

D group: FIP: FA-601 (SEQ ID NO: 424), RIP: RA-604 (SEQ ID NO: 431), F3: F3-601 (SEQ ID NO: 360), R3: R3-601 (SEQ ID NO: 381),
Loop primer: LPF-601 (SEQ ID NO: 397), LPR-601 (SEQ ID NO: 411)

2) Preparation of Human CK19RNA Sample

Following the operation as shown in Test example 2-1, samples were prepared so that the copy numbers were 60000, 20000, 6000, 2000, 600, 200, 60, 20 and 0 (control), respectively.

3) Composition of Reaction Solution, 4) RT-LAMP Method and 5) Observation of Amplification were Conducted in a Similar Manner as Test Example 2-1.

6) Results

Figure 25:
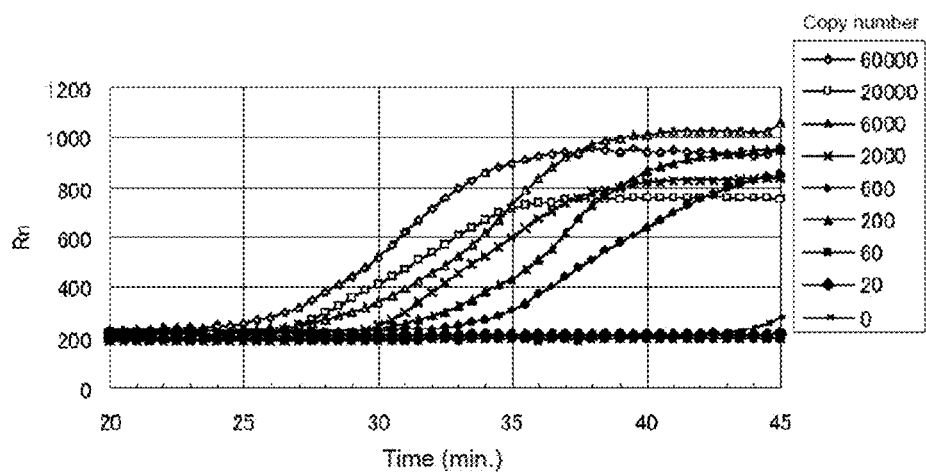
FIG. 25 is a view showing results of LAMP conducted by using Primer set D of human CK19 (Test example 2-4)
Figure 26:
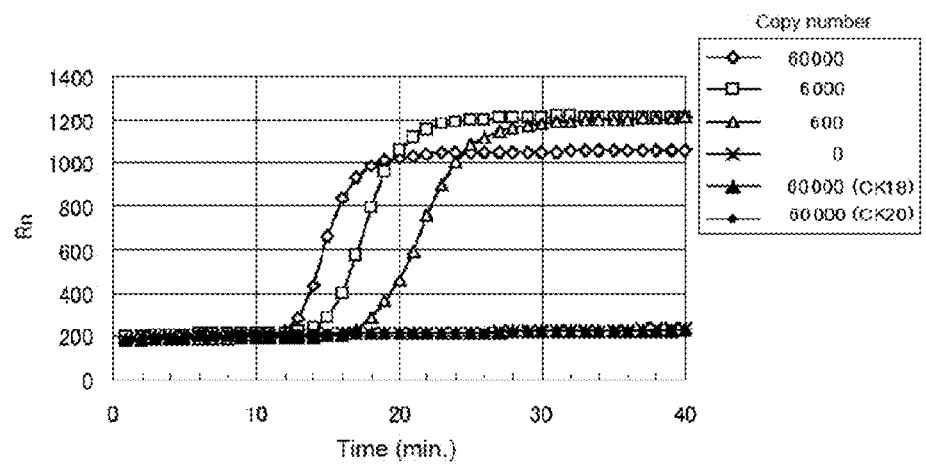
FIG. 26 shows amplification specificity when LAMP is conducted using Primer set A of human CK19 (Test example 2-5)
Figure 27:
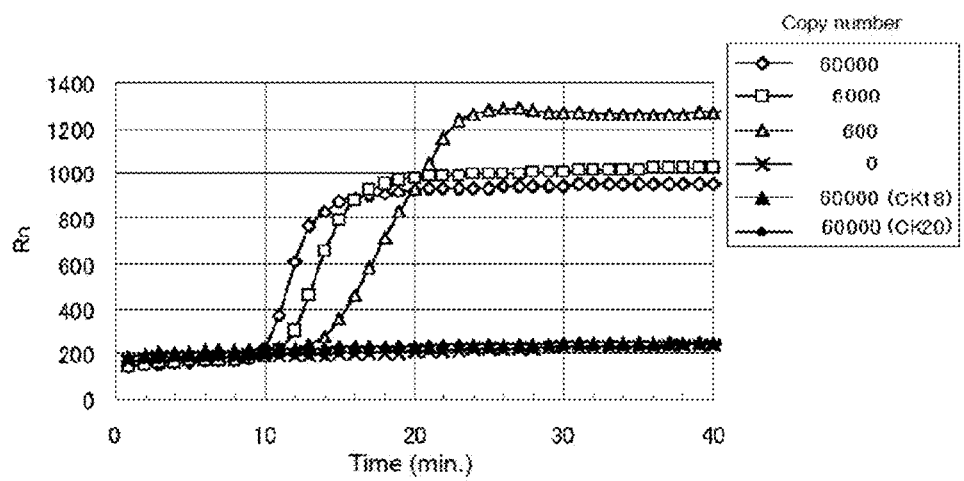
FIG. 27 shows amplification specificity when LAMP is conducted using Primer set B of human CK19 (Test example 2-5)
Figure 28:
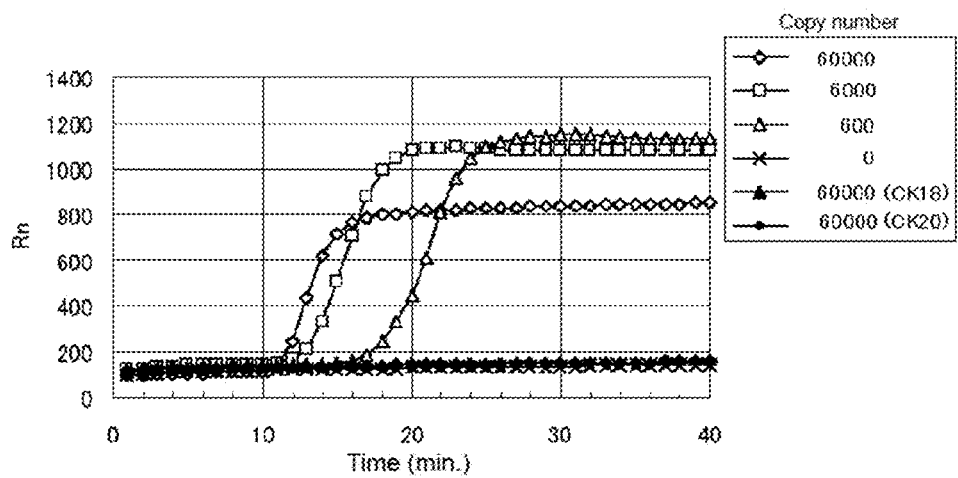
FIG. 28 shows amplification specificity when LAMP is conducted using Primer set C of human CK19 (Test example 2-5)
Figure 29:
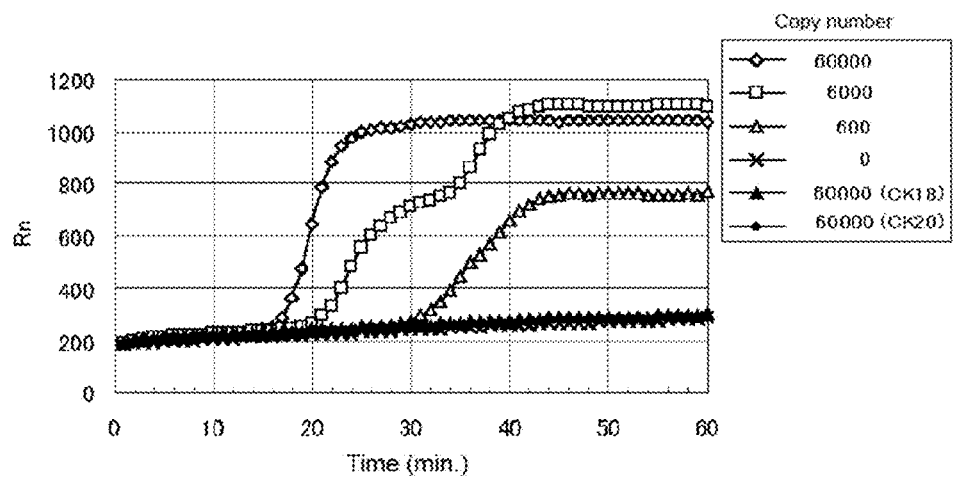
FIG. 29 shows amplification specificity when LAMP is conducted using Primer set D of human CK19 (Test example 2-5)

Results are shown in FIGS. 22 to 25. These results show that in every group of primer set, the larger the number of copies, the shorter the timer required until amplification of nucleic acid can be observed, and amplification was observed at about 15 to 25 minutes when the copy number was 60000. As for Group A, amplification was observed at 20 to 30 minutes when the copy number was 200 or more (FIG. 22); as for Group B, amplification was observed at 15 to 20 minutes when the copy number was 200 or more (FIG. 23), as for Group C, amplification was observed at 15 to 25 minutes when the copy number was 600 or more (FIG. 24); and as for Group D, amplification was observed at 25 to 35 minutes when the copy number was 200 or more (FIG. 25).

Test Example 2-5

Amplification Specificity to Human CK19RNA

Amplification specificity to human CK19RNA was examined when measurement was conducted using each primer set shown in Test example 2-4. It is known that cytokeratins (CK) have isoforms such as human CK18, 20 and the like besides human CK19. These isoforms comprises a base sequence having about 60% homology with human CK19. This test was conducted for determining whether human CK19 could be tested distinguishably from human CK18 or 20 when measurement was conducted by using the above primer sets.

1) Primer Set

Examination was made for the same primer sets as used in Test example 2-4.

2) Preparation of RNA Sample

Human CK19RNA samples were prepared so that the copy numbers were 60000, 6000, 600 and 0 (control) by conducting operation similar to that of Test example 2-1. As to RNAs of human CK18 and human CK20, samples were prepared in a similar manner so that the respective copy numbers were 60000.

3) Composition of Reaction Solution, 4) RT-LAMP Method and 5) Observation of Amplification were Conducted in a Similar Manner as Test Example 2-1.

6) Results

FIGS. 26 to 29 show results using each primer set shown in Test example 2-4. These results show that human CK19RNA, but absolutely not human CK18RNA and human CK20RNA are amplified when any group of primer set is used.

Test Example 2-6

Observation of Amplification with Respect to Human CK19RNA (Measurement of Turbidity)

1) Primer Set (Group C)

Examination was made for a primer set using FIP:FA-1101 (SEQ ID NO: 422), RIP:RA-1101 (SEQ ID NO: 423), F3:F3-1101 (SEQ ID NO: 359), R3:R3-1101 (SEQ ID NO: 380) and loop primers: LPF-1101 (SEQ ID NO: 394) and LPR-1101 (SEQ ID NO: 407) in combination.

2) Preparation of Human CK19RNA Sample

Samples were prepared so that the copy numbers were 100000, 10000, 1000 and 0 (control) by conducting operation similar to that of Test example 2-1.

3) Composition of Reaction Solution

| | |
|---|---|
| dNTPs (manufactured by GIBCO) | 0.4 mM |
| MgSO$_4$ | 2 mM |
| Dithiothreitol | 5 mM |
| Betaine) (manufactured by Sigma) | 640 mM |
| Thermopol buffer (manufactured by New England BioLabs) | |
| AMV reverse transcriptase (manufactured by Promega) | 1.25 U |
| Bst DNA polymerase (manufactured by New England BioLabs) | 16 U |
| Tergitol (manufactured by Sigma) | 1% |
| Primer | |
| FIP       40 pmol,   RIP      40 pmol, | |
| F3 primer   5 pmol,   R3 primer  5 pmol, | |
| Loop primer(loop F, loop R) | each 20 pmol |
| Tris HCl(pH 8) | 60 mM |

4) RT-LAMP Method was Conducted in the Manner as Described in Test Example 2-1. The Reaction was Allowed for 1.5 Hour in a 0.2 mL Tube at 65° C.

5) Observation of Amplification

Turbidity of the RT-LAMP reaction was determined over time from absorbance at a wavelength of 500 nm. As a measuring machine, LA-200 manufactured by Teramecs was used.

6) Results

Figure 30:
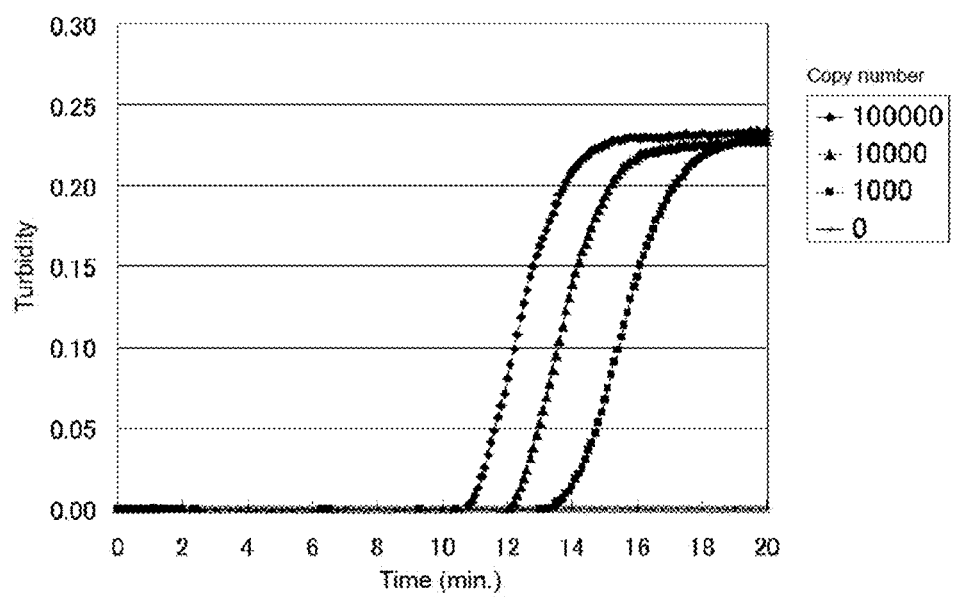
FIG. 30 is a view showing results of LAMP conducted by using Primer set C of human CK19 (Test example 2-6)

Results are shown in FIG. 30. Depending on the copy number of template, starting of amplification was observed between 11 and 13 minutes after starting the measurement.

Test Example 2-7

Observation of Amplification with Respect to Human CK19RNA (Measurement of Turbidity)

1) Primer Set (Group C)

Examination was made for a primer set using FIP:FA-1101 (SEQ ID NO: 422), RIP:RA-1101 (SEQ ID NO: 423), F3:F3-1101 (SEQ ID NO: 359), R3:R3-1101 (SEQ ID NO: 380) and loop primers: LPF-1101 (SEQ ID NO: 394) and LPR-1101 (SEQ ID NO: 407) in combination, and for the primer set added with RNase inhibiter.

2) Preparation of Human CK19RNA Sample

Samples were prepared so that the copy numbers were 100000, 10000, 1000 and 0 (control) by conducting operation similar to that of Test example 2-1.

3) Composition of Reaction Solution

A reaction solution having a similar composition as that of Test example 2-6 was used except that 25 U of RNase Inhibitor (manufactured by TOYOBO) was added.

4) RT-LAMP Method and 5) Observation of Amplification were Conducted in a Similar Manner as Test Example 2-6.

6) Results

Figure 31:
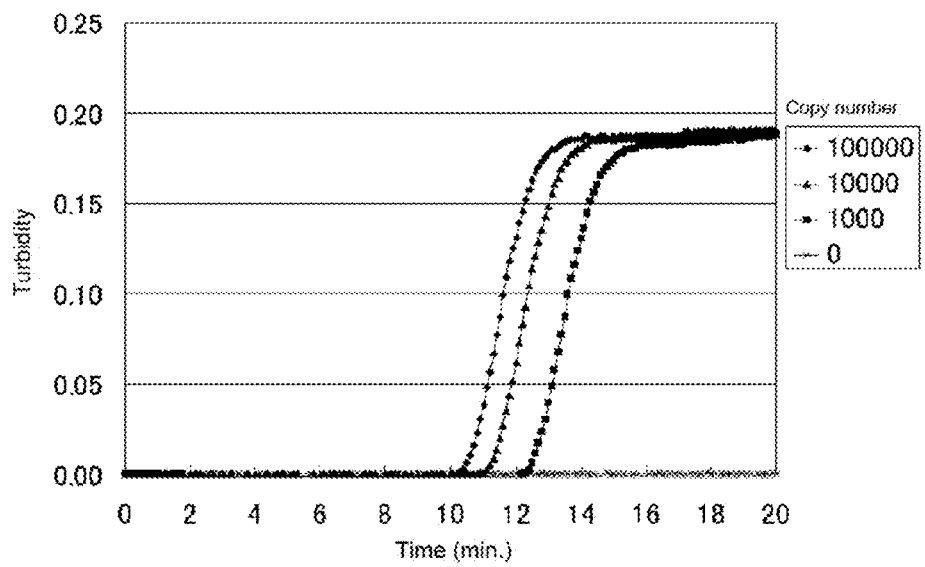
FIG. 31 is a view showing results of LAMP conducted by using Primer set C of human CK19 (Test example 2-7)

Results are shown in FIG. 31. Depending on the copy number of template, starting of amplification was observed between 10 and 12 minutes after starting the measurement. By adding RNase inhibitor, influence of substances that inhibit amplification reaction was reduced, so that the time required until amplification can be observed was reduce.

Test Example 3-1

This test was conducted in order to examine the time required until amplification could be observed from the starting of the reaction for each primer set, measured by the RT-LAMP method using the following combinations of primers from the various primers shown in Example 3-2.

1) Method for Preparing Human CK20 RNA Sample

By conducting RT-PCR using a primer designed based on a base sequence of human CK20, human CK20cDNA was isolated from total RNA derived from KATOIII (stomach cancer cell). From human CK20cDNA cloned into pBluescript (plasmid manufactured by STRATAGENE), a transcription product was synthesized using in vitro transcription system (Riboprobe in vitro transcription system (manufactured by Promega)). RNA concentration of the undiluted solution thus obtained was determined by measuring absorbance at 260 nm, and based on the result, the solution was diluted in 50 ng/µl yeast RNA (manufactured by Ambion) so that the copy number of RNA of human CK20 was 600000, which were used as template solutions.

2) Primer Set

A variety of primers were used in the combinations as shown in Table 2.

TABLE 2

| Primer set and time required until amplification can be observed | | | | |
|---|---|---|---|---|
| FIP | RIP | F3 primer | R3 primer | Time (min) |
| KFA-5 | KRA-5 | KF3-5 | KR3-5 | 25 |
| SEQ ID NO: 461 | SEQ ID NO: 468 | SEQ ID NO: 444 | SEQ ID NO: 455 | |
| KFA-5a | KRA-5 | KF3-5 | KR3-5 | 26 |
| SEQ ID NO: 462 | SEQ ID NO: 468 | SEQ ID NO: 444 | SEQ ID NO: 455 | |
| KFA-5b | KRA-5 | KF3-5 | KR3-5 | 23 |
| SEQ ID NO: 463 | SEQ ID NO: 468 | SEQ ID NO: 444 | SEQ ID NO: 455 | |
| KFA-5d | KRA-5 | KF3-5 | KR3-5 | 26 |
| SEQ ID NO: 464 | SEQ ID NO: 468 | SEQ ID NO: 444 | SEQ ID NO: 455 | |
| KFA-5e | KRA-5 | KF3-5 | KR3-5 | 25 |
| SEQ ID NO: 465 | SEQ ID NO: 468 | SEQ ID NO: 444 | SEQ ID NO: 455 | |
| KFA-5f | KRA-5 | KF3-5 | KR3-5 | 24 |
| SEQ ID NO: 466 | SEQ ID NO: 468 | SEQ ID NO: 444 | SEQ ID NO: 455 | |
| KFA-5 | KRA-5a | KF3-5 | KR3-5 | 30 |
| SEQ ID NO: 461 | SEQ ID NO: 469 | SEQ ID NO: 444 | SEQ ID NO: 455 | |
| KFA-5 | KRA-5c | KF3-5 | KR3-5 | 35 |
| SEQ ID NO: 461 | SEQ ID NO: 470 | SEQ ID NO: 444 | SEQ ID NO: 455 | |
| KFA-5 | KRA-5d | KF3-5 | KR3-5 | 30 |
| SEQ ID NO: 461 | SEQ ID NO: 471 | SEQ ID NO: 444 | SEQ ID NO: 455 | |
| KFA-5 | KRA-5e | KF3-5 | KR3-5 | 36 |
| SEQ ID NO: 461 | SEQ ID NO: 472 | SEQ ID NO: 444 | SEQ ID NO: 455 | |
| KFA-5 | KRA-5f | KF3-5 | KR3-5 | 40 |
| SEQ ID NO: 461 | SEQ ID NO: 473 | SEQ ID NO: 444 | SEQ ID NO: 455 | |

3) Composition of Reaction Solution

A similar composition with that of Test example 1-1 was used, and loop primers were not added.

4) RT-LAMP Method

To 23 µl of reaction solution containing the above four of primers, 2 µl of RNA sample of human CK20 was added, and heated at 65° C. for one hour.

5) Observation of Amplification

Measurement was conducted in real time in a similar manner with Test example 1-1.

6) Results

The time required until amplification could be observed when reaction was conducted using each primer set is shown in Table 2. These results show that the maximum time is 40 minutes and amplification was confirmed in 30 minutes in most of the primer sets.

Test Example 3-2

This test was conducted in order to examine the sensitivity when measurement by RT-LAMP method was conducted using a primer set requiring a short time for observation of amplification selected from the primer sets examined in Test example 3-1, and using a primer set combined with loop primers.

1) Method for Preparing Human CK20RNA Sample

Samples were prepared so that the copy numbers were 0, 190, 960, 4800, 24000, 120000, 600000 respectively by conducting a similar operation as Test example 3-1.

2) Primer Set

Examination was made for the primer sets of following combinations.

Set 1: FIP (KFA-5b; SEQ ID NO: 463), RIP (KRA-5; SEQ ID NO: 468)
F3 primer (KF3-5; SEQ ID NO: 444), R3 primer (KR3-5; SEQ ID NO: 455)
Loop primers (K-LPF2; SEQ ID NO: 457), LK-LPR1; SEQ ID NO: 459)

Set 2: FIP (KFA-5b; SEQ ID NO: 463), RIP (KRA-5; SEQ ID NO: 468)
F3 primer (KF3-5; SEQ ID NO: 444), R3 primer (KR3-5; SEQ ID NO: 455)
Loop primers (K-LPF2; SEQ ID NO: 457), LK-LPR2; SEQ ID NO: 459)

3) Composition of Reaction Solution

A similar composition with that of Test example 1-1 was used.

4) RT-LAMP Method and 5) Observation of Amplification were Conducted in a Similar Manner as Test Example 3-1.

6) Results

Figure 32:
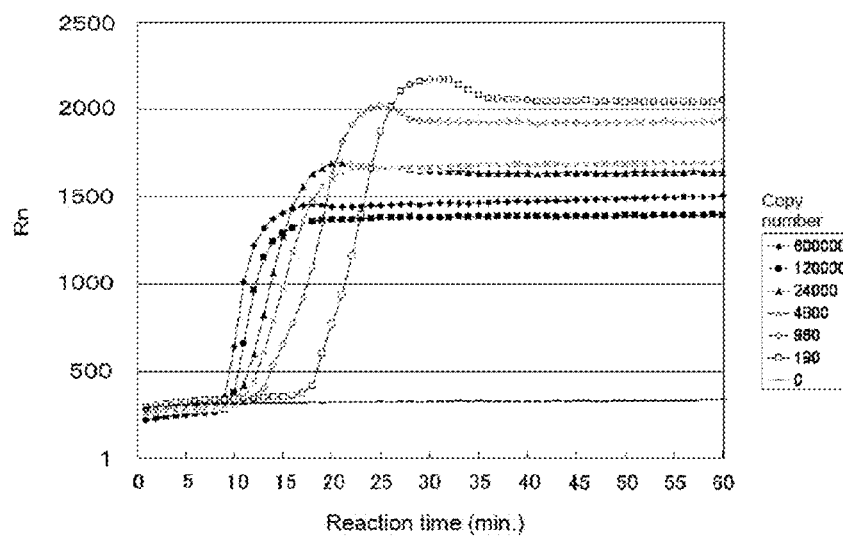
FIG. 32 is a view showing results of LAMP conducted by using Primer set 1 of human CK20 (Test example 3-2)

The examination result as to Primer set 1 is shown in FIG. 32. The result shows that the larger the amount of template of human CK20RNA, the shorter the time required until amplification can be observed. However, even in the case where the amount of template was 190 copies, DNA amplification was observed in 30 minutes, and even in the case where the amount of template was 600000 copies, DNA amplification was observed at about 10 minutes. A similar result was obtained for the case of Primer set 2.

Test Example 3-3

Amplification Specificity to Human CK20RNA

Amplification specificity to human CK20 when measurement was conducted using the primer sets selected in Test example 3-2 was examined. It is known that cytokeratins (CK) have isoforms such as human CK18, 19 and the like besides human CK20. These isoforms comprises a base sequence having about 60% homology with human CK20. This test was conducted for determining whether human CK20 could be tested distinguishably from human CK18 or 19 when measurement was conducted by using primer sets according to the present invention.

1) Method for Preparing RNA Sample

An RNA sample of human CK20 having a copy number of 600000 was prepared in a similar manner as described in Test example 3-1. Also as to RNAs of human CK18 and human CK19, samples were prepared in a similar manner.

2) Primer Set

Primer sets 1 and 2 selected in Test example 3-2 were used.

3) Composition of Reaction Solution, 4) RT-LAMP Method, and 5) Observation of Amplification were Conducted in a Similar Manner as Test Example 3-2.

6) Results

Figure 33:
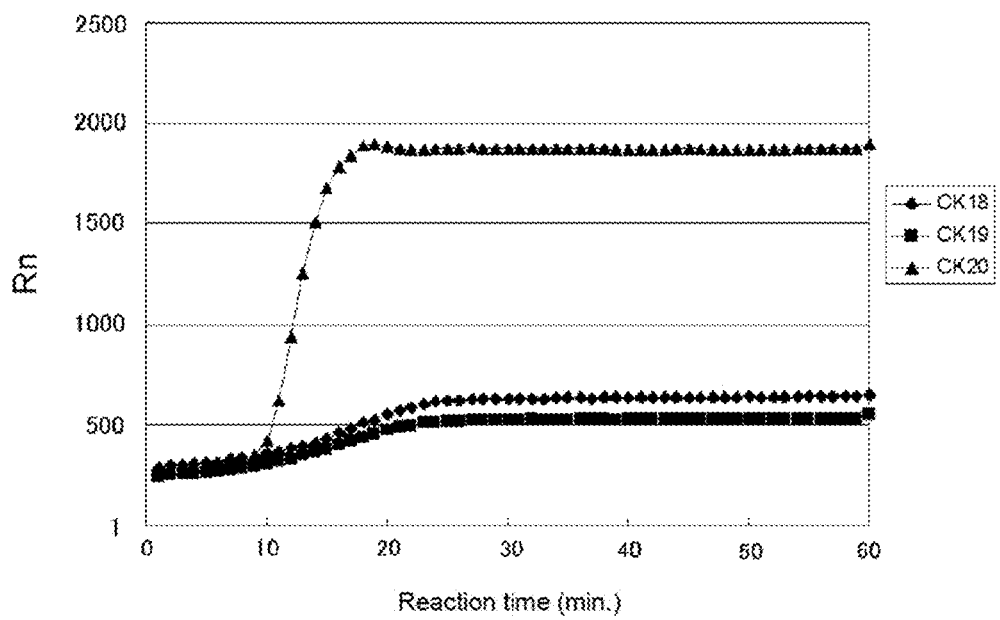
FIG. 33 shows amplification specificity when LAMP is conducted using Primer set 1 of human CK20 (Test example 3-3)

An examination result as to Primer set 1 is shown in FIG. 33. The result shows that human CK20RNA, but absolutely not human CK18RNA and human CK19RNA are amplified when Primer set 1 is used, revealing specificity to human CK20RNA. A similar result was obtained for the case of Primer set 2.

Test Example 3-4

Measurement Sensitivity

This test was conducted in order to examine the sensitivity of measurement for human CK20RNA when the measurement was conducted using each primer set.

1) Method for Preparing Human CK20RNA Sample

Samples were prepared so that the copy numbers were 0, 190, 960, 4800, 24000, 120000, 600000 respectively by conducting a similar operation as Test example 3-1.

2) Primer Set

Examination was made for the primer set of following combination.

Set 3: FIP (AFA; SEQ ID NO: 467), RIP (ARAf; SEQ ID NO: 474), F3 primer (AF3; SEQ ID NO: 443), R3 primer (AR3; SEQ ID NO: 454)
Loop primers (LPF2; SEQ ID NO: 393), (LPR6; SEQ ID NO: 458)

3) Composition of Reaction Solution, 4) RT-LAMP Method and 5) Observation of Amplification were Conducted in a Similar Manner as Test Example 3-2.

6) Results

Figure 34:
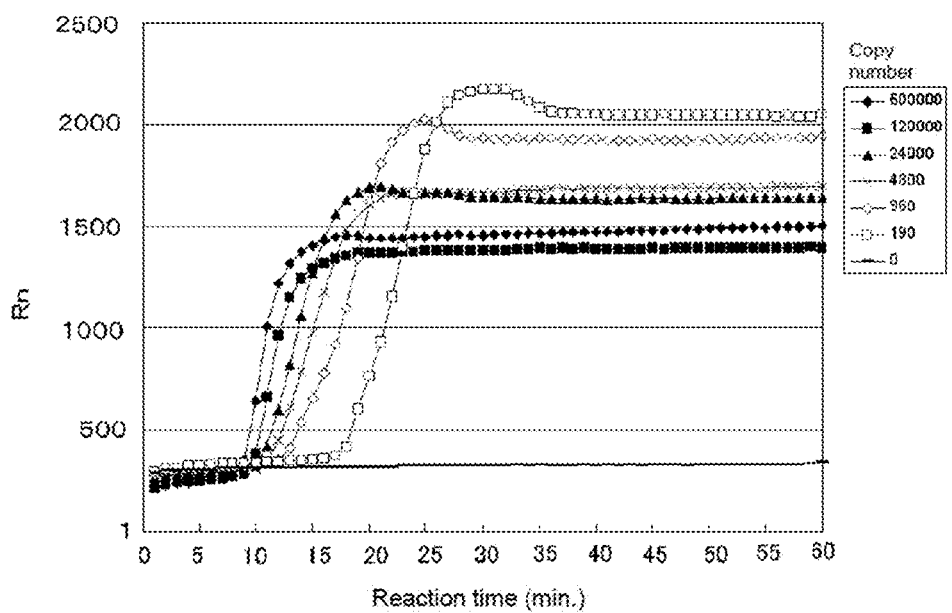
FIG. 34 is a view showing results of LAMP conducted by using Primer set 3 of human CK20 (Test example 3-4)

The examination results are shown in FIG. 34. The results show that the larger the amount of template of human CK20RNA, the shorter the time required until amplification can be observed. However, even in the case where the amount of template was 190 copies, DNA amplification was observed in 30 minutes, and even in the case where the amount of template was 600000 copies, DNA amplification was observed at about 10 minutes.

Test Example 3-5

This test was conducted in order to examine amplification specificity to human CK20RNA when measurement was conducted using the primer set selected in Test example 3-4.

1) Method for Preparing RNA Sample

An RNA sample of human CK20 was prepared so that the copy number was 600000. RNA samples of human CK18 and human CK19 were also prepared in a similar manner.

2) Primer Set

The primer set (Set 3) selected in Test example 3-4 was selected.

3) Composition of Reaction Solution, 4) RT-LAMP Method and 5) Observation of Amplification were Conducted in a Similar Manner as Test Example 3-2.

6) Results

Figure 35:
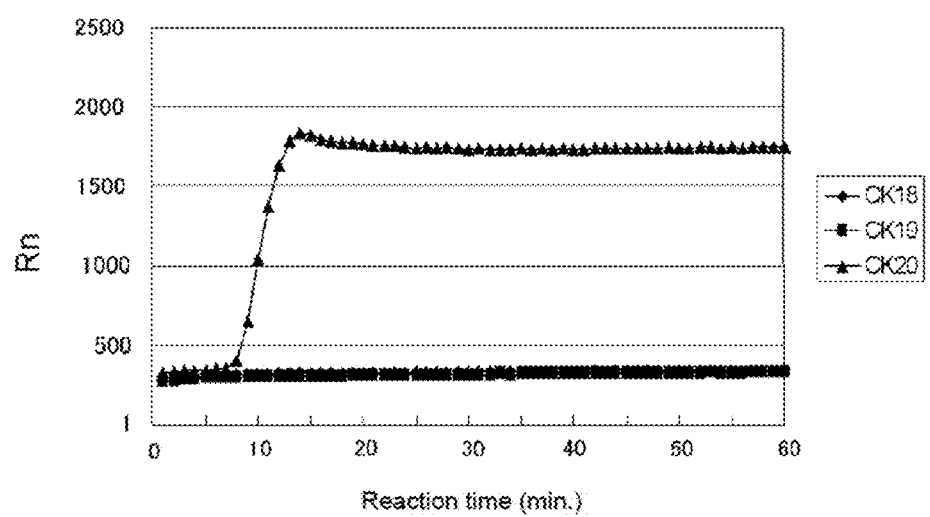
FIG. 35 shows amplification specificity when LAMP is conducted using Primer set 3 of human CK20 (Test example 3-5)

The results are shown in FIG. 35. These results show that human CK20RNA, but absolutely not human CK18RNA and human CK19RNA are amplified by the selected primer set.

INDUSTRIAL APPLICABILITY

As described above, it was found that when the LAMP method is conducted using a primer or a primer set of the present invention, human CK18RNA, CK19RNA and CK20RNA can be amplified with efficiency and specificity. According to this finding, primers of the present invention enable detection of human CK18RNA, CK19RNA and CK20RNA in short time, and reduction of time required for diagnosis of cancer metastasis to lymph nodes using nucleic acid amplifying means.

The invention claimed is:

1. A primer set for loop-mediated isothermal polymerase chain reaction to detect Cytokeratin 19, comprising first, second, third, and fourth primers, wherein the first primer onsists of the nucleotide sequence set forth in SEQ ID NO. 419, the second primer consists of the nucleotide sequence set forth in SEQ ID NO. 421, the third primer consists of the nucleotide sequence set forth in SEQ ID NO. 358, and the fourth primer consists of the nucleotide sequence complementary to SEQ ID NO. 379.

2. The primer set of claim 1, further comprising fifth and sixth primers, wherein the fifth primer consists of the nucleotide sequence set forth in SEQ ID NO. 392, and the sixth primer consists the nucleotide sequence set forth in SEQ ID NO. 406.

3. A reagent for loop-mediated isothermal polymerase chain reaction to detect Cytokeratin 19, comprising a buffer and the primer set of claim 1.

4. A reagent for loop-mediated isothermal polymerase chain reaction to detect Cytokeratin 19, comprising a buffer and the primer set of claim 2.

5. A method for diagnosing cancer metastasis to a lymph node by detecting cytokeratin 19 mRNA in a lymph node sample, comprising the steps of:
   providing RNA extracted from a patient's lymph node;
   synthesizing cDNA in the presence of a reverse transcriptase activity,
   amplifying cytokeratin 19 cDNA in the presence of the primer set of claim 1 by loop-mediated isothermal polymerase chain reaction,
   wherein detection of cytokeratin 19 cDNA amplification indicates cancer metastasis to said lymph node.

6. The method according to claim 5, wherein a patient's biopsied lymph node is tested for cytokeratin 19 expression before completion of surgery on the patient.

* * * * *

SEQUENCE LISTING

<160> NUMBER OF SEQ ID NOS: 475

<210> SEQ ID NO 1
<211> LENGTH: 1412
<212> TYPE: DNA
<213> ORGANISM: Homo sapiens

<400> SEQUENCE: 1

```
cggggtcgtc cgcaaagcct gagtcctgtc ctttctctct ccccggacag catgagcttc      60
accactcgct ccaccttctc caccaactac cggtccctgg gctctgtcca ggcgcccagc     120
tacggcgccc ggccggtcag cagcgcggcc agcgtctatg caggcgctgg gggctctggt     180
tcccggatct ccgtgtcccg ctccaccagc ttcaggggcg gcatgggggtc cggggggcctg     240 gccaccggga tagccggggg tctggcagga atgggaggca tccagaacga aaggagacc      300 atgcaaagcc tgaacgaccg cctggcctct tacctggaca gagtgaggag cctggagacc      360
gagaaccgga ggctggagag caaaatccgg gagcacttgg agaagaaggg accccaggtc      420
agagactgga gccattactt caagatcatc gaggacctga gggctcagat cttcgcaaat      480
actgtggaca atgcccgcat cgttctgcag attgacaatg cccgtcttgc tgctgatgac      540
tttagagtca agtatgagac agagctggcc atgcgccagt ctgtggagaa cgacatccat      600
gggctccgca aggtcattga tgacaccaat atcacacgac tgcagctgga gacagagatc      660
gaggctctca aggaggagct gctcttcatg aagaagaacc acgaagagga agtaaaaggc      720
ctacaagccc agattgccag ctctgggttg accgtggagg tagatgcccc caatctcag      780 gacctcgcca agatcatggc agacatccgg gcccaatatg acgagctggc tcggaagaac      840
cgagaggagc tagacaagta ctggtctcag cagattgagg agagcaccac agtggtcacc      900
acacagtctg ctgaggttgg agctgctgag acgacgctca cagagctgag acgtacagtc      960
cagtccttgg agatcgacct ggactccatg agaaatctga aggccagctt ggagaacagc     1020
ctgagggagg tggaggcccg ctacgcccta cagatggagc agctcaacgg atcctgctg     1080 cacttgagt cagagctggc acagacccgg gcagagggac agcgccaggc ccaggagtat     1140
gaggccctgc tgaacatcaa ggtcaagctg gaggctgaga tcgccaccta ccgccgcctg     1200
ctggaagatg gcgaggactt taatcttggt gatgccttgg acagcagcaa ctccatgcaa     1260
accatccaaa agaccaccac ccgccggata gtggatggca aagtggtgtc tgagaccaat     1320
gacaccaaag ttctgaggca ttaagccagc agaagcaggg taccctttgg ggagcaggag     1380
gccaataaaa agttcagagt tcattggatg tc                                   1412
```

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 2

```
tgaagtaatg gctccagtct ctg                                              23
```

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide primer for CK18 gene

```
<400> SEQUENCE: 3
agtaatggct ccagtctctg ac                                              22

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 4
ttgaagtaat ggctccagtc tct                                             23

<210> SEQ ID NO 5
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 5
acctggggtc ccttctt                                                    17

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 6
gggtcccttc ttctccaag                                                  19

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 7
ggtcccttct tctccaagtg                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 8
gtcccttctt ctccaagtgc                                                 20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 9
tcccttcttc tccaagtgct                                                 20

<210> SEQ ID NO 10
<211> LENGTH: 20
<212> TYPE: DNA
```

```
<213> ORGANISM: Artificial Sequence
<220> FEATURE:
<223> OTHER INFORMATION: Synthetic oligonucleotide primer for CK18 gene

<400> SEQUENCE: 10
cccttcttct ccaagtgctc                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 11
ccttcttctc caagtgctcc                                                   20

<210> SEQ ID NO 12
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 12
acagactggc gcatggc                                                      17

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 13
tcaatgacct tgcggagcc                                                    19

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 14
atcaatgacc ttgcggagcc                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 15
catcaatgac cttgcggagc                                                   20

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 16
tcatcaatga ccttgcggag c                                                 21
```

```
<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 17
agcctcgatc tctgtctcc                                                  19

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 18
gagctggcaa tctgggct                                                   18

<210> SEQ ID NO 19
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 19
agctggcaat ctgggctt                                                   18

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 20
gctggcaatc tgggcttg                                                   18

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 21
ctggcaatct gggcttgtag g                                               21

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 22
tggcaatctg ggcttgtagg                                                 20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide primer for CK18 gene
```

```
<400> SEQUENCE: 23
ggcaatctgg gcttgtaggc                                                  20

<210> SEQ ID NO 24
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 24
cacggtcaac ccagagc                                                     17

<210> SEQ ID NO 25
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 25
gatcttggcg aggtcctga                                                   19

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 26
cggatgtctg ccatgatctt g                                                21

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 27
ccagctcgtc atattgggcc                                                  20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 28
cagcagactg tgtggtgacc                                                  20

<210> SEQ ID NO 29
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 29
gtgagcgtcg tctcagca                                                    18

<210> SEQ ID NO 30
<211> LENGTH: 22
<212> TYPE: DNA
```

<213> ORGANISM: Artificial Sequence
<220> FEATURE:
<223> OTHER INFORMATION: Synthetic oligonucleotide primer for CK18 gene

<400> SEQUENCE: 30
gctggccttc agatttctca tg                                          22

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 31
ccaggctcct cactctgtcc a                                           21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 32
tccagtctct gacctggggt c                                           21

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 33
ctccacagac tggcgcatgg                                             20

<210> SEQ ID NO 34
<211> LENGTH: 22
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 34
gggcatctac ctccacggtc aa                                          22

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 35
gaccactgtg gtgctctcct c                                           21

<210> SEQ ID NO 36
<211> LENGTH: 22
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 36
cagctccaac ctcagcagac tg                                          22

<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 37
ggtttgcatg gagttgctgc tg                                              22

<210> SEQ ID NO 38
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 38
gagagcaaaa tccggga                                                    17

<210> SEQ ID NO 39
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 39
agagcaaaat ccgggag                                                    17

<210> SEQ ID NO 40
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 40
gagcaaaatc cgggagc                                                    17

<210> SEQ ID NO 41
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 41
aatccgggag cacttgg                                                    17

<210> SEQ ID NO 42
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 42
gaggctggag agcaaaa                                                    17

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

```
<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 43
cgtcttgctg ctgatgac                                                 18

<210> SEQ ID NO 44
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 44
gtcttgctgc tgatgactt                                                19

<210> SEQ ID NO 45
<211> LENGTH: 23
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 45
tagagtcaag tatgagacag agc                                           23

<210> SEQ ID NO 46
<211> LENGTH: 22
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 46
agagtcaagt atgagacaga gc                                            22

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 47
agtcaagtat gagacagagc t                                             21

<210> SEQ ID NO 48
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 48
gaacgacatc catgggc                                                  17

<210> SEQ ID NO 49
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 49
cgaggctctc aaggagg                                                  17

<210> SEQ ID NO 50
<211> LENGTH: 17
<212> TYPE: DNA
```

```
<213> ORGANISM: Artificial Sequence
<220> FEATURE:
<223> OTHER INFORMATION: Synthetic oligonucleotide primer for CK18 gene

<400> SEQUENCE: 50
gaggctctca aggagga                                                 17

<210> SEQ ID NO 51
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 51
aggctctcaa ggaggag                                                 17

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 52
catgaagaag aaccacgaag                                              20

<210> SEQ ID NO 53
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 53
gcctacaagc ccagattg                                                18

<210> SEQ ID NO 54
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 54
gttgaccgtg gaggtag                                                 17

<210> SEQ ID NO 55
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 55
ccccaaatct caggacc                                                 17

<210> SEQ ID NO 56
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 56
accgagagga gctagac                                                 17
```

```
<210> SEQ ID NO 57
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 57
aggagagcac cacagtg                                                  17

<210> SEQ ID NO 58
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 58
gagctgagac gtacagtc                                                 18

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 59
gagaccatgc aaagcctgaa                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 60
gaggctggag agcaaaatcc                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 61
cgtcttgctg ctgatgactt                                               20

<210> SEQ ID NO 62
<211> LENGTH: 22
<212> TYPE: DNA
<213> ORGANISM: Artificial Sequence
<220> FEATURE:
<223> OTHER INFORMATION: Synthetic oligonucleotide primer for CK18

<400> SEQUENCE: 62
ggaagtaaaa ggcctacaag cc                                            22

<210> SEQ ID NO 63
<211> LENGTH: 21
<212> TYPE: DNA
<213> ORGANISM: Artificial Sequence
<220> FEATURE:
<223> OTHER INFORMATION: Synthetic oligonucleotide primer for CK18 gene
```

```
<400> SEQUENCE: 63
gaaccgagag gagctagaca a                                              21

<210> SEQ ID NO 64
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 64
gtctcagcag attgaggaga g                                              21

<210> SEQ ID NO 65
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 65
tggaagatgg cgaggactttt                                               20

<210> SEQ ID NO 66
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 66
ctggcctctt acctgga                                                   17

<210> SEQ ID NO 67
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 67
aggagaccat gcaaagc                                                   17

<210> SEQ ID NO 68
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 68
tcttcgcaaa tactgtggac                                                20

<210> SEQ ID NO 69
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 69
cagatcttcg caaatactgt g                                              21

<210> SEQ ID NO 70
<211> LENGTH: 19
<212> TYPE: DNA
```

```
<213> ORGANISM: Artificial Sequence
<220> FEATURE:
<223> OTHER INFORMATION: Synthetic oligonucleotide primer for CK18 gene

<400> SEQUENCE: 70
tcgcaaatac tgtggacaa                                                    19

<210> SEQ ID NO 71
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 71
caaatactgt ggacaatgcc                                                   20

<210> SEQ ID NO 72
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 72
cgtcttgctg ctgatgac                                                     18

<210> SEQ ID NO 73
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 73
agtcaagtat gagacagagc t                                                 21

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 74
caccaatatc acacgactgc                                                   20

<210> SEQ ID NO 75
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 75
catgaagaag aaccacgaag                                                   20

<210> SEQ ID NO 76
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 76
agaaccacga agaggaag                                                     18
```

```
<210> SEQ ID NO 77
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 77
gttgaccgtg gaggtag                                                  17

<210> SEQ ID NO 78
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 78
cccaatatga cgagctgg                                                 18

<210> SEQ ID NO 79
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 79
aggagctaga caagtactgg                                               20

<210> SEQ ID NO 80
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 80
caagtactgg tctcagcag                                                19

<210> SEQ ID NO 81
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 81
tctgctgagg ttggagc                                                  17

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 82
gaggcatcca gaacgagaag                                               20

<210> SEQ ID NO 83
<211> LENGTH: 18
<212> TYPE: DNA
<213> ORGANISM: Artificial Sequence
<220> FEATURE:
<223> OTHER INFORMATION: Synthetic oligonucleotide primer for CK18 gene
```

```
<400> SEQUENCE: 83
agcctggaga ccgagaac                                                18

<210> SEQ ID NO 84
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 84
aatgcccgca tcgttctg                                                18

<210> SEQ ID NO 85
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 85
ggaggagctg ctcttcatg                                               19

<210> SEQ ID NO 86
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 86
ccgggcccaa tatgacga                                                18

<210> SEQ ID NO 87
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 87
ccgagaggag ctagacaagt                                              20

<210> SEQ ID NO 88
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 88
tgagatcgcc acctaccg                                                18

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 89
gatcatcgag gacctgaggg                                              20

<210> SEQ ID NO 90
<211> LENGTH: 23
<212> TYPE: DNA
```

```
<213> ORGANISM: Artificial Sequence
<220> FEATURE:
<223> OTHER INFORMATION: Synthetic oligonucleotide primer for CK18 gene

<400> SEQUENCE: 90
cagagactgg agccattact tca                                          23

<210> SEQ ID NO 91
<211> LENGTH: 24
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 91
gactggagcc attacttcaa gatc                                         24

<210> SEQ ID NO 92
<211> LENGTH: 24
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 92
actggagcca ttacttcaag atca                                         24

<210> SEQ ID NO 93
<211> LENGTH: 25
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 93
ctggagccat tacttcaaga tcatc                                        25

<210> SEQ ID NO 94
<211> LENGTH: 25
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 94
tggagccatt acttcaagat catcg                                        25

<210> SEQ ID NO 95
<211> LENGTH: 24
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 95
ggagccatta cttcaagatc atcg                                         24

<210> SEQ ID NO 96
<211> LENGTH: 25
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 96
gagccattac ttcaagatca tcgag                                        25
```

<210> SEQ ID NO 97
<211> LENGTH: 25
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 97
agccattact tcaagatcat cgagg                                    25

<210> SEQ ID NO 98
<211> LENGTH: 24
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 98
gccattactt caagatcatc gagg                                     24

<210> SEQ ID NO 99
<211> LENGTH: 25
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 99
ccattacttc aagatcatcg aggac                                    25

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 100
cattacttca agatcatcga ggacc                                    25

<210> SEQ ID NO 101
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 101
agaacgacat ccatgggct                                           19

<210> SEQ ID NO 102
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 102
gaacgacatc catgggctc                                           19

<210> SEQ ID NO 103
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

```
<400> SEQUENCE: 103
aacgacatcc atgggctcc                                                  19

<210> SEQ ID NO 104
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 104
acgacatcca tgggctcc                                                   18

<210> SEQ ID NO 105
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 105
catgggctcc gcaaggt                                                    17

<210> SEQ ID NO 106
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 106
tcacacgact gcagctgg                                                   18

<210> SEQ ID NO 107
<211> LENGTH: 22
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 107
caccaatatc acacgactgc ag                                              22

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 108
tatcacacga ctgcagctgg                                                 20

<210> SEQ ID NO 109
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 109
atcacacgac tgcagctgg                                                  19

<210> SEQ ID NO 110
<211> LENGTH: 24
<212> TYPE: DNA
```

```
<213> ORGANISM: Artificial Sequence
<220> FEATURE:
<223> OTHER INFORMATION: Synthetic oligonucleotide primer for CK18 gene

<400> SEQUENCE: 110
ttcatgaaga agaaccacga agag                                          24

<210> SEQ ID NO 111
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 111
agctctgggt tgaccgtg                                                 18

<210> SEQ ID NO 112
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 112
gctctgggtt gaccgtg                                                  17

<210> SEQ ID NO 113
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 113 ctctggttg accgtgg                                                   17
```

Note: SEQ ID 113 reads `ctctgggttg accgtgg` 17

```
<210> SEQ ID NO 114
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 114
tctgggttga ccgtgga                                                  17

<210> SEQ ID NO 115
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 115
ctgggttgac cgtggag                                                  17

<210> SEQ ID NO 116
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 116
tgggttgacc gtggagg                                                  17
```

```
<210> SEQ ID NO 117
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 117
ggttgaccgt ggaggtaga                                            19

<210> SEQ ID NO 118
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 118
gttgaccgtg gaggtagatg c                                         21

<210> SEQ ID NO 119
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 119
ttgaccgtgg aggtagatgc                                           20

<210> SEQ ID NO 120
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 120
tgaccgtgga ggtagatgc                                            19

<210> SEQ ID NO 121
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 121
gaccgtggag gtagatgcc                                            19

<210> SEQ ID NO 122
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 122
accgtggagg tagatgcc                                             18

<210> SEQ ID NO 123
<211> LENGTH: 18
<212> TYPE: DNA
<213> ORGANISM: Artificial Sequence
<220> FEATURE:
<223> OTHER INFORMATION: Synthetic oligonucleotide primer for CK18 gene
```

-continued

```
<400> SEQUENCE: 123
gcccccaaat ctcaggac                                                   18

<210> SEQ ID NO 124
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 124
cccaatatga cgagctggct                                                 20

<210> SEQ ID NO 125
<211> LENGTH: 23
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 125
caagtactgg tctcagcaga ttg                                             23

<210> SEQ ID NO 126
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 126
tgctgagacg acgctcac                                                   18

<210> SEQ ID NO 127
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 127
tgagacgtac agtccagtcc                                                 20

<210> SEQ ID NO 128
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 128
acagcctgag ggaggtg                                                    17

<210> SEQ ID NO 129
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 129
cgagaaccgg aggctggaga                                                 20

<210> SEQ ID NO 130
<211> LENGTH: 22
<212> TYPE: DNA
```

```
<213> ORGANISM: Artificial Sequence
<220> FEATURE:
<223> OTHER INFORMATION: Synthetic oligonucleotide primer for CK18 gene

<400> SEQUENCE: 130
agatcatcga ggacctgagg gc                                              22

<210> SEQ ID NO 131
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 131
gacatccatg ggctccgcaa                                                 20

<210> SEQ ID NO 132
<211> LENGTH: 22
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 132
caggacctcg ccaagatcat gg                                              22

<210> SEQ ID NO 133
<211> LENGTH: 22
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 133
cacacagtct gctgaggttg ga                                              22

<210> SEQ ID NO 134
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 134
gagacgacgc tcacagagct g                                               21

<210> SEQ ID NO 135
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 135
ccacccgccg gatagtggat                                                 20

<210> SEQ ID NO 136
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 136
gtcatcagca gcaagacg                                                   18
```

<210> SEQ ID NO 137
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 137
agtcatcagc agcaagacg                                           19

<210> SEQ ID NO 138
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 138
gcattgtcca cagtatttgc                                          20

<210> SEQ ID NO 139
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 139
cattgtccac agtatttgcg                                          20

<210> SEQ ID NO 140
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 140
attgtccaca gtatttgcga                                          20

<210> SEQ ID NO 141
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 141
ttgtccacag tatttgcga                                           19

<210> SEQ ID NO 142
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 142
tgtccacagt atttgcgaa                                           19

<210> SEQ ID NO 143
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

```
<400> SEQUENCE: 143
gtccacagta tttgcgaaga                                            20

<210> SEQ ID NO 144
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 144
tccacagtat ttgcgaagat c                                          21

<210> SEQ ID NO 145
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 145
ccacagtatt tgcgaagatc t                                          21

<210> SEQ ID NO 146
<211> LENGTH: 21
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 146
cacagtattt gcgaagatct g                                          21

<210> SEQ ID NO 147
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 147
ctcctccttg agagcct                                               17

<210> SEQ ID NO 148
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 148
tcctccttga gagcctc                                               17

<210> SEQ ID NO 149
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 149
cctccttgag agcctcg                                               17

<210> SEQ ID NO 150
<211> LENGTH: 17
<212> TYPE: DNA
```

```
<213> ORGANISM: Artificial Sequence
<220> FEATURE:
<223> OTHER INFORMATION: Synthetic oligonucleotide primer for CK18 gene

<400> SEQUENCE: 150
ctccttgaga gcctcga                                                 17

<210> SEQ ID NO 151
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 151
ccttgagagc ctcgatc                                                 17

<210> SEQ ID NO 152
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 152
cttgagagcc tcgatctc                                                18

<210> SEQ ID NO 153
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 153
gagcctcgat ctctgtc                                                 17

<210> SEQ ID NO 154
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 154
agcctcgatc tctgtctc                                                18

<210> SEQ ID NO 155
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 155
gcctcgatct ctgtctc                                                 17

<210> SEQ ID NO 156
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 156
acttcctctt cgtggttc                                                18
```

```
<210> SEQ ID NO 157
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 157 ggcctttac ttcctcttcg                                                20

<210> SEQ ID NO 158
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 158
tacttcctct tcgtggttc                                                19

<210> SEQ ID NO 159
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 159
tacctccacg gtcaacc                                                  17

<210> SEQ ID NO 160
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 160
cggatgtctg ccatgatc                                                 18

<210> SEQ ID NO 161
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 161
ggatgtctgc catgatctt                                                19

<210> SEQ ID NO 162
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 162
ccagctcgtc atattggg                                                 18

<210> SEQ ID NO 163
<211> LENGTH: 20
<212> TYPE: DNA
<213> ORGANISM: Artificial Sequence
<220> FEATURE:
<223> OTHER INFORMATION: Synthetic oligonucleotide primer for CK18 gene
```

<400> SEQUENCE: 163
caatctgctg agaccagtac                                          20

<210> SEQ ID NO 164
<211> LENGTH: 19
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 164
tctgctgaga ccagtactt                                           19

<210> SEQ ID NO 165
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 165
ctccaacctc agcagac                                             17

<210> SEQ ID NO 166
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 166
agtccaggtc gatctcc                                             17

<210> SEQ ID NO 167
<211> LENGTH: 20
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 167
tggccttcag atttctcatg                                          20

<210> SEQ ID NO 168
<211> LENGTH: 18
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 168
caagctggcc ttcagatt                                            18

<210> SEQ ID NO 169
<211> LENGTH: 17
<212> TYPE: DNA
<213> ORGANISM: Artificial Sequence
<220> FEATURE:
<223> OTHER INFORMATION: Synthetic oligonucleotide primer for CK18 gene

<400> SEQUENCE: 169
aaggtgcagc aggatcc                                             17

<210> SEQ ID NO 170
<211> LENGTH: 21
<212> TYPE: DNA

```
<213> ORGANISM: Artificial Sequence
<220> FEATURE:
<223> OTHER INFORMATION: Synthetic oligonucleotide primer for CK18

<400> SEQUENCE: 170
taatggctcc agtctctgac c                                            21

<210> SEQ ID NO 171
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 171
tcaatctgca gaacgatgcg                                              20

<210> SEQ ID NO 172
<211> LENGTH: 21
<212> TYPE: DNA
<213> ORGANISM: Artificial Sequence
<220> FEATURE:
<223> OTHER INFORMATION: Synthetic oligonucleotide primer for CK18

<400> SEQUENCE: 172
gagagcctcg atctctgtct c                                            21

<210> SEQ ID NO 173
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 173
gagagcctcg atctctgtct                                              20

<210> SEQ ID NO 174
<211> LENGTH: 21
<212> TYPE: DNA
<213> ORGANISM: Artificial Sequence
<220> FEATURE:
<223> OTHER INFORMATION: Synthetic oligonucleotide primer for CK18

<400> SEQUENCE: 174
ttgtctagct cctctcggtt c                                            21

<210> SEQ ID NO 175
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 175
ttgtctagct cctctcggtt                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 176
caggtcgatc tccaaggact                                              20
```

<210> SEQ ID NO 177
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 177
gctggccttc agatttctca                      20

<210> SEQ ID NO 178
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 178
gctggcttaa tgcctcagaa                      20

<210> SEQ ID NO 179
<211> LENGTH: 21
<212> TYPE: DNA
<213> ORGANISM: Artificial Sequence
<220> FEATURE:
<223> OTHER INFORMATION: Synthetic oligonucleotide primer for CK18

<400> SEQUENCE: 179
agctctgtct catacttgac t                    21

<210> SEQ ID NO 180
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 180
agtcatcagc agcaagacg                       19

<210> SEQ ID NO 181
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 181
gtcatcagca gcaagacg                        18

<210> SEQ ID NO 182
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 182
ggccttttac ttcctcttcg                      20

<210> SEQ ID NO 183
<211> LENGTH: 18
<212> TYPE: DNA
<213> ORGANISM: Artificial Sequence
<220> FEATURE:
<223> OTHER INFORMATION: Synthetic oligonucleotide primer for CK18

-continued

<400> SEQUENCE: 183
acttcctctt cgtggttc					18

<210> SEQ ID NO 184
<211> LENGTH: 17
<212> TYPE: DNA
<213> ORGANISM: Artificial Sequence
<220> FEATURE:
<223> OTHER INFORMATION: Synthetic oligonucleotide primer for CK18

<400> SEQUENCE: 184
ctggcaatct gggcttg					17

<210> SEQ ID NO 185
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 185
gaggtcctga gatttggg					18

<210> SEQ ID NO 186
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 186
tctagctcct ctcggttc					18

<210> SEQ ID NO 187
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 187
caatctgctg agaccagtac					20

<210> SEQ ID NO 188
<211> LENGTH: 17
<212> TYPE: DNA
<213> ORGANISM: Artificial Sequence
<220> FEATURE:
<223> OTHER INFORMATION: Synthetic oligonucleotide primer for CK18

<400> SEQUENCE: 188
ctccaacctc agcagac					17

<210> SEQ ID NO 189
<211> LENGTH: 17
<212> TYPE: DNA
<213> ORGANISM: Artificial Sequence
<220> FEATURE:
<223> OTHER INFORMATION: Synthetic oligonucleotide primer for CK18

<400> SEQUENCE: 189
cagactgtgt ggtgacc					17

<210> SEQ ID NO 190
<211> LENGTH: 17
<212> TYPE: DNA

```
<213> ORGANISM: Artificial Sequence
<220> FEATURE:
<223> OTHER INFORMATION: Synthetic oligonucleotide primer for CK18

<400> SEQUENCE: 190
actgtggtgc tctcctc                                                     17

<210> SEQ ID NO 191
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 191
gactgtacgt ctcagctc                                                    18

<210> SEQ ID NO 192
<211> LENGTH: 17
<212> TYPE: DNA
<213> ORGANISM: Artificial Sequence
<220> FEATURE:
<223> OTHER INFORMATION: Synthetic oligonucleotide primer for CK18

<400> SEQUENCE: 192
ggctgttctc caagctg                                                     17

<210> SEQ ID NO 193
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 193
catctgtagg gcgtagcg                                                    18

<210> SEQ ID NO 194
<211> LENGTH: 17
<212> TYPE: DNA
<213> ORGANISM: Artificial Sequence
<220> FEATURE:
<223> OTHER INFORMATION: Synthetic oligonucleotide primer for CK18

<400> SEQUENCE: 194
catactcctg ggcctgg                                                     17

<210> SEQ ID NO 195
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 195
gcgaagatct gagccctca                                                   19

<210> SEQ ID NO 196
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 196
catcagcagc aagacggg                                                    18
```

```
<210> SEQ ID NO 197
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 197
tgaagagcag ctcctccctt                                               19

<210> SEQ ID NO 198
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 198
gctctcctca atctgctgag                                               20

<210> SEQ ID NO 199
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 199
gctggccttc agatttctca                                               20

<210> SEQ ID NO 200
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 200
cctccctcag gctgttctc                                                19

<210> SEQ ID NO 201
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 201
ccaaagggta ccctgcttc                                                19

<210> SEQ ID NO 202
<211> LENGTH: 17
<212> TYPE: DNA
<213> ORGANISM: Artificial Sequence
<220> FEATURE:
<223> OTHER INFORMATION: Synthetic oligonucleotide primer for CK18

<400> SEQUENCE: 202
acctggggtc ccttctt                                                  17

<210> SEQ ID NO 203
<211> LENGTH: 19
<212> TYPE: DNA
<213> ORGANISM: Artificial Sequence
<220> FEATURE:
<223> OTHER INFORMATION: Synthetic oligonucleotide primer for CK18
```

<400> SEQUENCE: 203
gggtcccttc ttctccaag                                        19

<210> SEQ ID NO 204
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 204
ggtcccttct tctccaagtg                                       20

<210> SEQ ID NO 205
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 205
caagtgctcc cggattttgc                                       20

<210> SEQ ID NO 206
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 206
aagtgctccc ggattttgc                                        19

<210> SEQ ID NO 207
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 207
agtgctcccg gattttgct                                        19

<210> SEQ ID NO 208
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 208
gtgctcccgg attttgctc                                        19

<210> SEQ ID NO 209
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 209
tgctcccgga ttttgctct                                        19

<210> SEQ ID NO 210
<211> LENGTH: 19
<212> TYPE: DNA

```
-continued
<213> ORGANISM: Artificial Sequence
<220> FEATURE:
<223> OTHER INFORMATION: Synthetic oligonucleotide primer for CK18

<400> SEQUENCE: 210
gctcccggat tttgctctc                                                       19

<210> SEQ ID NO 211
<211> LENGTH: 24
<212> TYPE: DNA
<213> ORGANISM: Artificial Sequence
<220> FEATURE:
<223> OTHER INFORMATION: Synthetic oligonucleotide primer for CK18

<400> SEQUENCE: 211
cagctctgtc tcatacttga ctct                                                 24

<210> SEQ ID NO 212
<211> LENGTH: 17
<212> TYPE: DNA
<213> ORGANISM: Artificial Sequence
<220> FEATURE:
<223> OTHER INFORMATION: Synthetic oligonucleotide primer for CK18

<400> SEQUENCE: 212
acagactggc gcatggc                                                         17

<210> SEQ ID NO 213
<211> LENGTH: 22
<212> TYPE: DNA
<213> ORGANISM: Artificial Sequence
<220> FEATURE:
<223> OTHER INFORMATION: Synthetic oligonucleotide primer for CK18

<400> SEQUENCE: 213
cctcttcgtg gttcttcttc at                                                   22

<210> SEQ ID NO 214
<211> LENGTH: 19
<212> TYPE: DNA
<213> ORGANISM: Artificial Sequence
<220> FEATURE:
<223> OTHER INFORMATION: Synthetic oligonucleotide primer for CK18

<400> SEQUENCE: 214
cctcagcaga ctgtgtggt                                                       19

<210> SEQ ID NO 215
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 215
cagcagactg tgtggtgacc                                                      20

<210> SEQ ID NO 216
<211> LENGTH: 24
<212> TYPE: DNA
<213> ORGANISM: Artificial Sequence
<220> FEATURE:
<223> OTHER INFORMATION: Synthetic oligonucleotide primer for CK18

<400> SEQUENCE: 216
cagctctgtc tcatacttga ctct                                                 24
```

<210> SEQ ID NO 217
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 217
gagctggcaa tctgggct                                          18

<210> SEQ ID NO 218
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 218
tgtccaaggc atcaccaaga                                        20

<210> SEQ ID NO 219
<211> LENGTH: 21
<212> TYPE: DNA
<213> ORGANISM: Artificial Sequence
<220> FEATURE:
<223> OTHER INFORMATION: Synthetic oligonucleotide primer for CK18

<400> SEQUENCE: 219
gtccaaggca tcaccaagat t                                      21

<210> SEQ ID NO 220
<211> LENGTH: 22
<212> TYPE: DNA
<213> ORGANISM: Artificial Sequence
<220> FEATURE:
<223> OTHER INFORMATION: Synthetic oligonucleotide primer for CK18

<400> SEQUENCE: 220
cgcaaatact gtggacaatg cc                                     22

<210> SEQ ID NO 221
<211> LENGTH: 24
<212> TYPE: DNA
<213> ORGANISM: Artificial Sequence
<220> FEATURE:
<223> OTHER INFORMATION: Synthetic oligonucleotide primer for CK18

<400> SEQUENCE: 221
cagatcttcg caaatactgt ggac                                   24

<210> SEQ ID NO 222
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 222
gatcatcgag gacctgaggg                                        20

<210> SEQ ID NO 223
<211> LENGTH: 21
<212> TYPE: DNA
<213> ORGANISM: Artificial Sequence
<220> FEATURE:
<223> OTHER INFORMATION: Synthetic oligonucleotide primer for CK18

```
<400> SEQUENCE: 223
ccaatatcac acgactgcag c                                              21

<210> SEQ ID NO 224
<211> LENGTH: 24
<212> TYPE: DNA
<213> ORGANISM: Artificial Sequence
<220> FEATURE:
<223> OTHER INFORMATION: Synthetic oligonucleotide primer for CK18

<400> SEQUENCE: 224
ttgatgacac caatatcaca cgac                                           24

<210> SEQ ID NO 225
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 225
tcacacgact gcagctgg                                                  18

<210> SEQ ID NO 226
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 226
tcgaggctct caaggagg                                                  18

<210> SEQ ID NO 227
<211> LENGTH: 18
<212> TYPE: DNA
<213> ORGANISM: Artificial Sequence
<220> FEATURE:
<223> OTHER INFORMATION: Synthetic oligonucleotide primer for CK18

<400> SEQUENCE: 227
cccccaaatc tcaggacc                                                  18

<210> SEQ ID NO 228
<211> LENGTH: 17
<212> TYPE: DNA
<213> ORGANISM: Artificial Sequence
<220> FEATURE:
<223> OTHER INFORMATION: Synthetic oligonucleotide primer for CK18

<400> SEQUENCE: 228
gagatcgacc tggactc                                                   17

<210> SEQ ID NO 229
<211> LENGTH: 22
<212> TYPE: DNA
<213> ORGANISM: Artificial Sequence
<220> FEATURE:
<223> OTHER INFORMATION: Synthetic oligonucleotide primer for CK18

<400> SEQUENCE: 229
gacaccaata tcacacgact gc                                             22

<210> SEQ ID NO 230
<211> LENGTH: 23
<212> TYPE: DNA
```

```
<213> ORGANISM: Artificial Sequence
<220> FEATURE:
<223> OTHER INFORMATION: Synthetic oligonucleotide primer for CK18

<400> SEQUENCE: 230
tgacaccaat atcacacgac tgc                                              23

<210> SEQ ID NO 231
<211> LENGTH: 22
<212> TYPE: DNA
<213> ORGANISM: Artificial Sequence
<220> FEATURE:
<223> OTHER INFORMATION: Synthetic oligonucleotide primer for CK18

<400> SEQUENCE: 231
acaccaatat cacacgactg ca                                               22

<210> SEQ ID NO 232
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 232
ggcccaatat gacgagctgg                                                  20

<210> SEQ ID NO 233
<211> LENGTH: 20
<212> TYPE: DNA
<213> ORGANISM: Artificial Sequence
<220> FEATURE:
<223> OTHER INFORMATION: Synthetic oligonucleotide primer for CK18

<400> SEQUENCE: 233
tggcaaagtg gtgtctgaga                                                  20

<210> SEQ ID NO 234
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 234
tgaagtaatg gctccagtct ctggagagca aaatccggga                            40

<210> SEQ ID NO 235
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 235
tgaagtaatg gctccagtct ctgagagcaa aatccgggag                            40

<210> SEQ ID NO 236
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 236
tgaagtaatg gctccagtct ctggagcaaa atccgggagc                            40
```

<210> SEQ ID NO 237
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 237
tgaagtaatg gctccagtct ctgaatccgg gagcacttgg        40

<210> SEQ ID NO 238
<211> LENGTH: 39
<212> TYPE: DNA
<213> ORGANISM: Artificial Sequence
<220> FEATURE:
<223> OTHER INFORMATION: Synthetic oligonucleotide primer for CK18

<400> SEQUENCE: 238
agtaatggct ccagtctctg acgagagcaa aatccggga        39

<210> SEQ ID NO 239
<211> LENGTH: 39
<212> TYPE: DNA
<213> ORGANISM: Artificial Sequence
<220> FEATURE:
<223> OTHER INFORMATION: Synthetic oligonucleotide primer for CK18

<400> SEQUENCE: 239
agtaatggct ccagtctctg acagagcaaa atccgggag        39

<210> SEQ ID NO 240
<211> LENGTH: 39
<212> TYPE: DNA
<213> ORGANISM: Artificial Sequence
<220> FEATURE:
<223> OTHER INFORMATION: Synthetic oligonucleotide primer for CK18

<400> SEQUENCE: 240
agtaatggct ccagtctctg acgagcaaaa tccgggagc        39

<210> SEQ ID NO 241
<211> LENGTH: 39
<212> TYPE: DNA
<213> ORGANISM: Artificial Sequence
<220> FEATURE:
<223> OTHER INFORMATION: Synthetic oligonucleotide primer for CK18

<400> SEQUENCE: 241
agtaatggct ccagtctctg acaatccggg agcacttgg        39

<210> SEQ ID NO 242
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 242
ttgaagtaat ggctccagtc tctgagagca aaatccggga        40

<210> SEQ ID NO 243
<211> LENGTH: 40
<212> TYPE: DNA
<213> ORGANISM: Artificial Sequence
<220> FEATURE:
<223> OTHER INFORMATION: Synthetic oligonucleotide primer for CK18

```
<400> SEQUENCE: 243
ttgaagtaat ggctccagtc tctagagcaa aatccgggag                            40

<210> SEQ ID NO 244
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 244
ttgaagtaat ggctccagtc tctgagcaaa atccgggagc                            40

<210> SEQ ID NO 245
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 245
ttgaagtaat ggctccagtc tctaatccgg gagcacttgg                            40

<210> SEQ ID NO 246
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 246
gggtcccttc ttctccaagg aggctggaga gcaaaa                                36

<210> SEQ ID NO 247
<211> LENGTH: 34
<212> TYPE: DNA
<213> ORGANISM: Artificial Sequence
<220> FEATURE:
<223> OTHER INFORMATION: Synthetic oligonucleotide primer for CK18

<400> SEQUENCE: 247
acctggggtc ccttcttgag gctggagagc aaaa                                  34

<210> SEQ ID NO 248
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 248
ggtcccttct tctccaagtg gaggctggag agcaaaa                               37

<210> SEQ ID NO 249
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 249
tcccttcttc tccaagtgct gaggctggag agcaaaa                               37

<210> SEQ ID NO 250
<211> LENGTH: 37
<212> TYPE: DNA
```

```
<213> ORGANISM: Artificial Sequence
<220> FEATURE:
<223> OTHER INFORMATION: Synthetic oligonucleotide primer for CK18

<400> SEQUENCE: 250
ccttcttctc caagtgctcc gaggctggag agcaaaa                              37

<210> SEQ ID NO 251
<211> LENGTH: 35
<212> TYPE: DNA
<213> ORGANISM: Artificial Sequence
<220> FEATURE:
<223> OTHER INFORMATION: Synthetic oligonucleotide primer for CK18

<400> SEQUENCE: 251
acagactggc gcatggccgt cttgctgctg atgac                               35

<210> SEQ ID NO 252
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 252
acagactggc gcatggcgtc ttgctgctga tgactt                              36

<210> SEQ ID NO 253
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 253
tcaatgacct tgcggagcct agagtcaagt atgagacaga gc                       42

<210> SEQ ID NO 254
<211> LENGTH: 41
<212> TYPE: DNA
<213> ORGANISM: Artificial Sequence
<220> FEATURE:
<223> OTHER INFORMATION: Synthetic oligonucleotide primer for CK18

<400> SEQUENCE: 254
tcaatgacct tgcggagcca gagtcaagta tgagacagag c                        41

<210> SEQ ID NO 255
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 255
tcaatgacct tgcggagcca gtcaagtatg agacagagct                          40

<210> SEQ ID NO 256
<211> LENGTH: 43
<212> TYPE: DNA
<213> ORGANISM: Artificial Sequence
<220> FEATURE:
<223> OTHER INFORMATION: Synthetic oligonucleotide primer for CK18

<400> SEQUENCE: 256
atcaatgacc ttgcggagcc tagagtcaag tatgagacag agc                      43
```

```
<210> SEQ ID NO 257
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 257
atcaatgacc ttgcggagcc agagtcaagt atgagacaga gc                    42

<210> SEQ ID NO 258
<211> LENGTH: 41
<212> TYPE: DNA
<213> ORGANISM: Artificial Sequence
<220> FEATURE:
<223> OTHER INFORMATION: Synthetic oligonucleotide primer for CK18

<400> SEQUENCE: 258
atcaatgacc ttgcggagcc agtcaagtat gagacagagc t                     41

<210> SEQ ID NO 259
<211> LENGTH: 43
<212> TYPE: DNA
<213> ORGANISM: Artificial Sequence
<220> FEATURE:
<223> OTHER INFORMATION: Synthetic oligonucleotide primer for CK18

<400> SEQUENCE: 259
catcaatgac cttgcggagc tagagtcaag tatgagacag agc                   43

<210> SEQ ID NO 260
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 260
catcaatgac cttgcggagc agagtcaagt atgagacaga gc                    42

<210> SEQ ID NO 261
<211> LENGTH: 41
<212> TYPE: DNA
<213> ORGANISM: Artificial Sequence
<220> FEATURE:
<223> OTHER INFORMATION: Synthetic oligonucleotide primer for CK18

<400> SEQUENCE: 261
catcaatgac cttgcggagc agtcaagtat gagacagagc t                     41

<210> SEQ ID NO 262
<211> LENGTH: 44
<212> TYPE: DNA
<213> ORGANISM: Artificial Sequence
<220> FEATURE:
<223> OTHER INFORMATION: Synthetic oligonucleotide primer for CK18

<400> SEQUENCE: 262
tcatcaatga ccttgcggag ctagagtcaa gtatgagaca gagc                  44

<210> SEQ ID NO 263
<211> LENGTH: 43
<212> TYPE: DNA
<213> ORGANISM: Artificial Sequence
<220> FEATURE:
<223> OTHER INFORMATION: Synthetic oligonucleotide primer for CK18
```

<400> SEQUENCE: 263
tcatcaatga ccttgcggag cagagtcaag tatgagacag agc    43

<210> SEQ ID NO 264
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 264
tcatcaatga ccttgcggag cagtcaagta tgagacagag ct    42

<210> SEQ ID NO 265
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 265
agcctcgatc tctgtctccg aacgacatcc atgggc    36

<210> SEQ ID NO 266
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 266
ggcaatctgg gcttgtaggc cgaggctctc aaggagg    37

<210> SEQ ID NO 267
<211> LENGTH: 35
<212> TYPE: DNA
<213> ORGANISM: Artificial Sequence
<220> FEATURE:
<223> OTHER INFORMATION: Synthetic oligonucleotide primer for CK18

<400> SEQUENCE: 267
gagctggcaa tctgggctcg aggctctcaa ggagg    35

<210> SEQ ID NO 268
<211> LENGTH: 35
<212> TYPE: DNA
<213> ORGANISM: Artificial Sequence
<220> FEATURE:
<223> OTHER INFORMATION: Synthetic oligonucleotide primer for CK18

<400> SEQUENCE: 268
gagctggcaa tctgggctag gctctcaagg aggag    35

<210> SEQ ID NO 269
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 269
tggcaatctg ggcttgtagg cgaggctctc aaggagg    37

<210> SEQ ID NO 270
<211> LENGTH: 37
<212> TYPE: DNA

```
<213> ORGANISM: Artificial Sequence
<220> FEATURE:
<223> OTHER INFORMATION: Synthetic oligonucleotide primer for CK18

<400> SEQUENCE: 270
tggcaatctg ggcttgtagg aggctctcaa ggaggag                              37

<210> SEQ ID NO 271
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 271
ggcaatctgg gcttgtaggc gaggctctca aggagga                              37

<210> SEQ ID NO 272
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 272
ggcaatctgg gcttgtaggc aggctctcaa ggaggag                              37

<210> SEQ ID NO 273
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 273
cacggtcaac ccagagccat gaagaagaac cacgaag                              37

<210> SEQ ID NO 274
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 274
gatcttggcg aggtcctgag cctacaagcc cagattg                              37

<210> SEQ ID NO 275
<211> LENGTH: 38
<212> TYPE: DNA
<213> ORGANISM: Artificial Sequence
<220> FEATURE:
<223> OTHER INFORMATION: Synthetic oligonucleotide primer for CK18

<400> SEQUENCE: 275
cggatgtctg ccatgatctt ggttgaccgt ggaggtag                             38

<210> SEQ ID NO 276
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 276
ccagctcgtc atattgggcc ccccaaatct caggacc                              37
```

<210> SEQ ID NO 277
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 277
cagcagactg tgtggtgacc accgagagga gctagac                    37

<210> SEQ ID NO 278
<211> LENGTH: 35
<212> TYPE: DNA
<213> ORGANISM: Artificial Sequence
<220> FEATURE:
<223> OTHER INFORMATION: Synthetic oligonucleotide primer for CK18

<400> SEQUENCE: 278
gtgagcgtcg tctcagcaag gagagcacca cagtg                      35

<210> SEQ ID NO 279
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 279
gctggccttc agatttctca tggagctgag acgtacagtc                 40

<210> SEQ ID NO 280
<211> LENGTH: 41
<212> TYPE: DNA
<213> ORGANISM: Artificial Sequence
<220> FEATURE:
<223> OTHER INFORMATION: Synthetic oligonucleotide primer for CK18

<400> SEQUENCE: 280
ccaggctcct cactctgtcc agagaccatg caaagcctga a               41

<210> SEQ ID NO 281
<211> LENGTH: 38
<212> TYPE: DNA
<213> ORGANISM: Artificial Sequence
<220> FEATURE:
<223> OTHER INFORMATION: Synthetic oligonucleotide primer for CK18

<400> SEQUENCE: 281
tccagtctct gacctggggt cgaggctgga gagcaaaa                   38

<210> SEQ ID NO 282
<211> LENGTH: 38
<212> TYPE: DNA
<213> ORGANISM: Artificial Sequence
<220> FEATURE:
<223> OTHER INFORMATION: Synthetic oligonucleotide primer for CK18

<400> SEQUENCE: 282
ctccacagac tggcgcatgg cgtcttgctg ctgatgac                   38

<210> SEQ ID NO 283
<211> LENGTH: 44
<212> TYPE: DNA
<213> ORGANISM: Artificial Sequence
<220> FEATURE:
<223> OTHER INFORMATION: Synthetic oligonucleotide primer for CK18

<400> SEQUENCE: 283
gggcatctac ctccacggtc aaggaagtaa aaggcctaca agcc                44

<210> SEQ ID NO 284
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 284
gaccactgtg gtgctctcct cgaaccgaga ggagctagac aa                  42

<210> SEQ ID NO 285
<211> LENGTH: 43
<212> TYPE: DNA
<213> ORGANISM: Artificial Sequence
<220> FEATURE:
<223> OTHER INFORMATION: Synthetic oligonucleotide primer for CK18

<400> SEQUENCE: 285
cagctccaac ctcagcagac tggtctcagc agattgagga gag                 43

<210> SEQ ID NO 286
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 286
ggtttgcatg gagttgctgc tgtggaagat ggcgaggact tt                  42

<210> SEQ ID NO 287
<211> LENGTH: 38
<212> TYPE: DNA
<213> ORGANISM: Artificial Sequence
<220> FEATURE:
<223> OTHER INFORMATION: Synthetic oligonucleotide primer for CK18

<400> SEQUENCE: 287
gatcatcgag gacctgaggg gtcatcagca gcaagacg                       38

<210> SEQ ID NO 288
<211> LENGTH: 39
<212> TYPE: DNA
<213> ORGANISM: Artificial Sequence
<220> FEATURE:
<223> OTHER INFORMATION: Synthetic oligonucleotide primer for CK18

<400> SEQUENCE: 288
gatcatcgag gacctgaggg agtcatcagc agcaagacg                      39

<210> SEQ ID NO 289
<211> LENGTH: 44
<212> TYPE: DNA
<213> ORGANISM: Artificial Sequence
<220> FEATURE:
<223> OTHER INFORMATION: Synthetic oligonucleotide primer for CK18

<400> SEQUENCE: 289
cagagactgg agccattact tcacacagta tttgcgaaga tctg                44

<210> SEQ ID NO 290
<211> LENGTH: 44
<212> TYPE: DNA

```
<213> ORGANISM: Artificial Sequence
<220> FEATURE:
<223> OTHER INFORMATION: Synthetic oligonucleotide primer for CK18

<400> SEQUENCE: 290
cagagactgg agccattact tcatccacag tatttgcgaa gatc                   44

<210> SEQ ID NO 291
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 291
cagagactgg agccattact tcatgtccac agtatttgcg aa                     42

<210> SEQ ID NO 292
<211> LENGTH: 43
<212> TYPE: DNA
<213> ORGANISM: Artificial Sequence
<220> FEATURE:
<223> OTHER INFORMATION: Synthetic oligonucleotide primer for CK18

<400> SEQUENCE: 292
cagagactgg agccattact tcaattgtcc acagtatttg cga                    43

<210> SEQ ID NO 293
<211> LENGTH: 43
<212> TYPE: DNA
<213> ORGANISM: Artificial Sequence
<220> FEATURE:
<223> OTHER INFORMATION: Synthetic oligonucleotide primer for CK18

<400> SEQUENCE: 293
cagagactgg agccattact tcagcattgt ccacagtatt tgc                    43

<210> SEQ ID NO 294
<211> LENGTH: 45
<212> TYPE: DNA
<213> ORGANISM: Artificial Sequence
<220> FEATURE:
<223> OTHER INFORMATION: Synthetic oligonucleotide primer for CK18

<400> SEQUENCE: 294
gactggagcc attacttcaa gatccacagt atttgcgaag atctg                  45

<210> SEQ ID NO 295
<211> LENGTH: 43
<212> TYPE: DNA
<213> ORGANISM: Artificial Sequence
<220> FEATURE:
<223> OTHER INFORMATION: Synthetic oligonucleotide primer for CK18

<400> SEQUENCE: 295
gactggagcc attacttcaa gatctgtcca cagtatttgc gaa                    43

<210> SEQ ID NO 296
<211> LENGTH: 44
<212> TYPE: DNA
<213> ORGANISM: Artificial Sequence
<220> FEATURE:
<223> OTHER INFORMATION: Synthetic oligonucleotide primer for CK18

<400> SEQUENCE: 296
gactggagcc attacttcaa gatcattgtc cacagtattt gcga                   44
```

<210> SEQ ID NO 297
<211> LENGTH: 34
<212> TYPE: DNA
<213> ORGANISM: Artificial Sequence
<220> FEATURE:
<223> OTHER INFORMATION: Synthetic oligonucleotide primer for CK18

<400> SEQUENCE: 297
catgggctcc gcaaggtcct ccttgagagc ctcg     34

<210> SEQ ID NO 298
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 298
agaacgacat ccatgggctg agcctcgatc tctgtc     36

<210> SEQ ID NO 299
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 299
gaacgacatc catgggctcc ctccttgaga gcctcg     36

<210> SEQ ID NO 300
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 300
gaacgacatc catgggctcg agcctcgatc tctgtc     36

<210> SEQ ID NO 301
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 301
gaacgacatc catgggctcg cctcgatctc tgtctc     36

<210> SEQ ID NO 302
<211> LENGTH: 35
<212> TYPE: DNA
<213> ORGANISM: Artificial Sequence
<220> FEATURE:
<223> OTHER INFORMATION: Synthetic oligonucleotide primer for CK18

<400> SEQUENCE: 302
acgacatcca tgggctcccc tccttgagag cctcg     35

<210> SEQ ID NO 303
<211> LENGTH: 35
<212> TYPE: DNA
<213> ORGANISM: Artificial Sequence
<220> FEATURE:
<223> OTHER INFORMATION: Synthetic oligonucleotide primer for CK18

```
<400> SEQUENCE: 303
acgacatcca tgggctccga gcctcgatct ctgtc                    35

<210> SEQ ID NO 304
<211> LENGTH: 35
<212> TYPE: DNA
<213> ORGANISM: Artificial Sequence
<220> FEATURE:
<223> OTHER INFORMATION: Synthetic oligonucleotide primer for CK18

<400> SEQUENCE: 304
acgacatcca tgggctccgc ctcgatctct gtctc                    35

<210> SEQ ID NO 305
<211> LENGTH: 34
<212> TYPE: DNA
<213> ORGANISM: Artificial Sequence
<220> FEATURE:
<223> OTHER INFORMATION: Synthetic oligonucleotide primer for CK18

<400> SEQUENCE: 305
catgggctcc gcaaggtcct tgagagcctc gatc                     34

<210> SEQ ID NO 306
<211> LENGTH: 34
<212> TYPE: DNA
<213> ORGANISM: Artificial Sequence
<220> FEATURE:
<223> OTHER INFORMATION: Synthetic oligonucleotide primer for CK18

<400> SEQUENCE: 306
catgggctcc gcaaggtgag cctcgatctc tgtc                     34

<210> SEQ ID NO 307
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 307
tcacacgact gcagctggac ttcctcttcg tggttc                   36

<210> SEQ ID NO 308
<211> LENGTH: 38
<212> TYPE: DNA
<213> ORGANISM: Artificial Sequence
<220> FEATURE:
<223> OTHER INFORMATION: Synthetic oligonucleotide primer for CK18

<400> SEQUENCE: 308
tcacacgact gcagctgggg ccttttactt cctcttcg                 38

<210> SEQ ID NO 309
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 309
tcacacgact gcagctggta cttcctcttc gtggttc                  37

<210> SEQ ID NO 310
<211> LENGTH: 40
<212> TYPE: DNA
```

<213> ORGANISM: Artificial Sequence
<220> FEATURE:
<223> OTHER INFORMATION: Synthetic oligonucleotide primer for CK18

<400> SEQUENCE: 310
caccaatatc acacgactgc agacttcctc ttcgtggttc         40

<210> SEQ ID NO 311
<211> LENGTH: 41
<212> TYPE: DNA
<213> ORGANISM: Artificial Sequence
<220> FEATURE:
<223> OTHER INFORMATION: Synthetic oligonucleotide primer for CK18

<400> SEQUENCE: 311
caccaatatc acacgactgc agtacttcct cttcgtggtt c        41

<210> SEQ ID NO 312
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 312
caccaatatc acacgactgc agggcctttt acttcctctt cg       42

<210> SEQ ID NO 313
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 313
atcacacgac tgcagctgga cttcctcttc gtggttc             37

<210> SEQ ID NO 314
<211> LENGTH: 38
<212> TYPE: DNA
<213> ORGANISM: Artificial Sequence
<220> FEATURE:
<223> OTHER INFORMATION: Synthetic oligonucleotide primer for CK18

<400> SEQUENCE: 314
atcacacgac tgcagctggt acttcctctt cgtggttc            38

<210> SEQ ID NO 315
<211> LENGTH: 39
<212> TYPE: DNA
<213> ORGANISM: Artificial Sequence
<220> FEATURE:
<223> OTHER INFORMATION: Synthetic oligonucleotide primer for CK18

<400> SEQUENCE: 315
atcacacgac tgcagctggg gcctttcact tcctcttcg           39

<210> SEQ ID NO 316
<211> LENGTH: 38
<212> TYPE: DNA
<213> ORGANISM: Artificial Sequence
<220> FEATURE:
<223> OTHER INFORMATION: Synthetic oligonucleotide primer for CK18

<400> SEQUENCE: 316
tatcacacga ctgcagctgg acttcctctt cgtggttc            38

```
<210> SEQ ID NO 317
<211> LENGTH: 39
<212> TYPE: DNA
<213> ORGANISM: Artificial Sequence
<220> FEATURE:
<223> OTHER INFORMATION: Synthetic oligonucleotide primer for CK18

<400> SEQUENCE: 317
tatcacacga ctgcagctgg tacttcctct tcgtggttc                              39

<210> SEQ ID NO 318
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 318
tatcacacga ctgcagctgg ggccttttac ttcctcttcg                             40

<210> SEQ ID NO 319
<211> LENGTH: 41
<212> TYPE: DNA
<213> ORGANISM: Artificial Sequence
<220> FEATURE:
<223> OTHER INFORMATION: Synthetic oligonucleotide primer for CK18

<400> SEQUENCE: 319
ttcatgaaga agaaccacga agagtacctc cacggtcaac c                           41

<210> SEQ ID NO 320
<211> LENGTH: 35
<212> TYPE: DNA
<213> ORGANISM: Artificial Sequence
<220> FEATURE:
<223> OTHER INFORMATION: Synthetic oligonucleotide primer for CK18

<400> SEQUENCE: 320
ctgggttgac cgtggagcgg atgtctgcca tgatc                                  35

<210> SEQ ID NO 321
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 321
ctgggttgac cgtggaggga tgtctgccat gatctt                                 36

<210> SEQ ID NO 322
<211> LENGTH: 39
<212> TYPE: DNA
<213> ORGANISM: Artificial Sequence
<220> FEATURE:
<223> OTHER INFORMATION: Synthetic oligonucleotide primer for CK18

<400> SEQUENCE: 322
gttgaccgtg gaggtagatg ccggatgtct gccatgatc                              39

<210> SEQ ID NO 323
<211> LENGTH: 37
<212> TYPE: DNA
<213> ORGANISM: Artificial Sequence
<220> FEATURE:
<223> OTHER INFORMATION: Synthetic oligonucleotide primer for CK18
```

<400> SEQUENCE: 323
tgaccgtgga ggtagatgcc ggatgtctgc catgatc 37

```
<210> SEQ ID NO 324
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 324
accgtggagg tagatgcccg gatgtctgcc atgatc 36

<210> SEQ ID NO 325
<211> LENGTH: 38
<212> TYPE: DNA
<213> ORGANISM: Artificial Sequence
<220> FEATURE:
<223> OTHER INFORMATION: Synthetic oligonucleotide primer for CK18

<400> SEQUENCE: 325
tgaccgtgga ggtagatgcg gatgtctgcc atgatctt 38

<210> SEQ ID NO 326
<211> LENGTH: 37
<212> TYPE: DNA
<213> ORGANISM: Artificial Sequence
<220> FEATURE:
<223> OTHER INFORMATION: Synthetic oligonucleotide primer for CK18

<400> SEQUENCE: 326
accgtggagg tagatgccgg atgtctgcca tgatctt 37

<210> SEQ ID NO 327
<211> LENGTH: 36
<212> TYPE: DNA
<213> ORGANISM: Artificial Sequence
<220> FEATURE:
<223> OTHER INFORMATION: Synthetic oligonucleotide primer for CK18

<400> SEQUENCE: 327
gcccccaaat ctcaggaccc agctcgtcat attggg 36

<210> SEQ ID NO 328
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 328
cccaatatga cgagctggct caatctgctg agaccagtac 40

<210> SEQ ID NO 329
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 329
caagtactgg tctcagcaga ttgctccaac ctcagcagac 40

<210> SEQ ID NO 330
<211> LENGTH: 35
<212> TYPE: DNA
```

```
<213> ORGANISM: Artificial Sequence
<220> FEATURE:
<223> OTHER INFORMATION: Synthetic oligonucleotide primer for CK18

<400> SEQUENCE: 330
tgctgagacg acgctcacag tccaggtcga tctcc                                    35

<210> SEQ ID NO 331
<211> LENGTH: 38
<212> TYPE: DNA
<213> ORGANISM: Artificial Sequence
<220> FEATURE:
<223> OTHER INFORMATION: Synthetic oligonucleotide primer for CK18

<400> SEQUENCE: 331
tgagacgtac agtccagtcc caagctggcc ttcagatt                                 38

<210> SEQ ID NO 332
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 332
tgagacgtac agtccagtcc tggccttcag atttctcatg                               40

<210> SEQ ID NO 333
<211> LENGTH: 34
<212> TYPE: DNA
<213> ORGANISM: Artificial Sequence
<220> FEATURE:
<223> OTHER INFORMATION: Synthetic oligonucleotide primer for CK18

<400> SEQUENCE: 333
acagcctgag ggaggtgaag gtgcagcagg atcc                                     34

<210> SEQ ID NO 334
<211> LENGTH: 41
<212> TYPE: DNA
<213> ORGANISM: Artificial Sequence
<220> FEATURE:
<223> OTHER INFORMATION: Synthetic oligonucleotide primer for CK18

<400> SEQUENCE: 334
cgagaaccgg aggctggaga taatggctcc agtctctgac c                             41

<210> SEQ ID NO 335
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 335
agatcatcga ggacctgagg gctcaatctg cagaacgatg cg                            42

<210> SEQ ID NO 336
<211> LENGTH: 41
<212> TYPE: DNA
<213> ORGANISM: Artificial Sequence
<220> FEATURE:
<223> OTHER INFORMATION: Synthetic oligonucleotide primer for CK18

<400> SEQUENCE: 336
gacatccatg ggctccgcaa gagagcctcg atctctgtct c                             41
```

```
<210> SEQ ID NO 337
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 337
gacatccatg ggctccgcaa gagagcctcg atctctgtct                              40

<210> SEQ ID NO 338
<211> LENGTH: 43
<212> TYPE: DNA
<213> ORGANISM: Artificial Sequence
<220> FEATURE:
<223> OTHER INFORMATION: Synthetic oligonucleotide primer for CK18

<400> SEQUENCE: 338
caggacctcg ccaagatcat gggaaccgag aggagctaga caa                         43

<210> SEQ ID NO 339
<211> LENGTH: 42
<212> TYPE: DNA
<213> ORGANISM: Artificial Sequence
<220> FEATURE:
<223> OTHER INFORMATION: Synthetic oligonucleotide primer for CK18

<400> SEQUENCE: 339
cacacagtct gctgaggttg gacaggtcga tctccaagga ct                          42

<210> SEQ ID NO 340
<211> LENGTH: 41
<212> TYPE: DNA
<213> ORGANISM: Artificial Sequence
<220> FEATURE:
<223> OTHER INFORMATION: Synthetic oligonucleotide primer for CK18

<400> SEQUENCE: 340
gagacgacgc tcacagagct ggctggcctt cagatttctc a                            41

<210> SEQ ID NO 341
<211> LENGTH: 40
<212> TYPE: DNA
<213> ORGANISM: Artificial Sequence
<220> FEATURE:
<223> OTHER INFORMATION: Synthetic oligonucleotide primer for CK18

<400> SEQUENCE: 341
ccacccgccg gatagtggat gctggcttaa tgcctcagaa                              40

<210> SEQ ID NO 342
<211> LENGTH: 1360
<212> TYPE: DNA
<213> ORGANISM: Homo sapiens

<400> SEQUENCE: 342
cgggggttgc tccgtccgtg ctccgcctcg ccatgacttc ctacagctat cgccagtcgt        60
cggccacgtc gtccttcgga ggcctgggcg gcggctccgt gcgttttggg ccgggggtcg       120
cttttcgcgc gcccagcatt cacggggggct ccggcggccg cggcgtatcc gtgtcctccg      180
cccgctttgt gtcctcgtcc tcctcggggg gctacgcgcg cggctacggc ggcgtcctga      240
ccgcgtccga cgggctgctg gcgggcaacg agaagctaac catgcagaac ctcaacgacc       300
gcctggcctc ctacctggac aaggtgcgcg ccctggagga ggccaacggc gagctagagg       360
```

-continued

```
tgaagatccg cgactggtac cagaagcagg ggcctgggcc ctcccgcgac tacagccact    420
actacacgac catccaggac ctgcgggaca agattcttgg tgccaccatt gagaactcca    480
ggattgtcct gcagatcgac aacgcccgtc tggctgcaga tgacttccga accaagtttg    540
agacggaaca ggctctgcgc atgagcgtgg aggccgacat caacggcctg cgcagggtgc    600
tggatgagct gacccctggcc aggaccgacc tggagatgca gatcgaaggc ctgaaggaag    660
agctggccta cctgaagaag aaccatgagg aggaaatcag tacgctgagg gccaagtgg    720 gaggccaggt cagtgtggag gtggattccg ctccgggcac cgatctcgcc aagatcctga    780
gtgacatgcg aagccaatat gaggtcatgg ccgagcagaa ccggaaggat gctgaagcct    840
ggttcaccag ccggactgaa gaattgaacc gggaggtcgc tggccacacg agcagctcc    900 agatgagcag gtccgaggtt actgacctgc ggcgcaccct tcagggtctt gagattgagc    960
tgcagtcaca gctgagcatg aaagctgcct tggaagacac actggcagaa acggaggcgc    1020
gctttggagc ccagctggcg catatccagg cgctgatcag cggtattgaa gcccagctgg    1080
cggatgtgcg agctgatagt gagcggcaga atcaggagta ccagcggctc atggacatca    1140
agtcgcggct ggagcaggag attgccacct accgcagcct gctcgaggga caggaagatc    1200
actacaacaa tttgtctgcc tccaaggtcc tctgaggcag caggctctgg ggcttctgct    1260
gtcctttgga gggtgtcttc tgggtagagg gatgggaagg aagggaccct taccccggc    1320 tcttctcctg acctgccaat aaaaatttat ggtccaaggg                          1360

<210> SEQ ID NO 343
<211> LENGTH: 22
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 343
tgtagtagtg gctgtagtcg cg                                              22

<210> SEQ ID NO 344
<211> LENGTH: 23
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 344
tcgtgtagta gtggctgtag tcg                                             23

<210> SEQ ID NO 345
<211> LENGTH: 22
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 345
ggagttctca atggtggcac ca                                              22

<210> SEQ ID NO 346
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 346
```

```
ttggcccctc agcgtac                                                  17

<210> SEQ ID NO 347
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 347
agcggaatcc acctccac                                                 18

<210> SEQ ID NO 348
<211> LENGTH: 20
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 348
aatccacctc cacactgacc                                               20

<210> SEQ ID NO 349
<211> LENGTH: 19
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 349
atccacctcc acactgacc                                                19

<210> SEQ ID NO 350
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 350
tccacctcca cactgacc                                                 18

<210> SEQ ID NO 351
<211> LENGTH: 19
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 351
agctagaggt gaagatccg                                                19

<210> SEQ ID NO 352
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 352
agatccgcga ctggtac                                                  17

<210> SEQ ID NO 353
<211> LENGTH: 17
<212> TYPE: DNA
<213> ORGANISM: Artificial Sequence
<220> FEATURE:
```

<223> OTHER INFORMATION: Synthetic oligonucleotide primer for CK19 gene

<400> SEQUENCE: 353
gtgaagatcc gcgactg                                               17

<210> SEQ ID NO 354
<211> LENGTH: 21
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 354
actactacac gaccatccag g                                          21

<210> SEQ ID NO 355
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 355
aagagctggc ctacctg                                               17

<210> SEQ ID NO 356
<211> LENGTH: 20
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 356
gaggaaatca gtacgctgag                                            20

<210> SEQ ID NO 357
<211> LENGTH: 19
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 357
gctaaccatg cagaacctc                                             19

<210> SEQ ID NO 358
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 358
tggtaccaga agcagggg                                              18

<210> SEQ ID NO 359
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 359
acctggagat gcagatcg                                              18

<210> SEQ ID NO 360

```
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 360
aagagctggc ctacctg                                                    17

<210> SEQ ID NO 361
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 361
agctggccta cctgaag                                                    17

<210> SEQ ID NO 362
<211> LENGTH: 20
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 362
gtgccaccat tgagaactcc                                                 20

<210> SEQ ID NO 363
<211> LENGTH: 21
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 363
tgtcctgcag atcgacaacg c                                               21

<210> SEQ ID NO 364
<211> LENGTH: 21
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 364
gtcctgcaga tcgacaacgc c                                               21

<210> SEQ ID NO 365
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 365
aggtcagtgt ggaggtgg                                                   18

<210> SEQ ID NO 366
<211> LENGTH: 20
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 366
```
tctcgccaag atcctgagtg                                                    20

<210> SEQ ID NO 367
<211> LENGTH: 20
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 367
tcgccaagat cctgagtgac                                                    20

<210> SEQ ID NO 368
<211> LENGTH: 22
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 368
agatcctgag tgacatgcga ag                                                 22

<210> SEQ ID NO 369
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 369
ggttcggaag tcatctgc                                                      18

<210> SEQ ID NO 370
<211> LENGTH: 20
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 370
cgtctcaaac ttggttcgga                                                    20

<210> SEQ ID NO 371
<211> LENGTH: 20
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 371
tccgtctcaa acttggttcg                                                    20

<210> SEQ ID NO 372
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 372
cgcatgtcac tcaggatc                                                      18

<210> SEQ ID NO 373
<211> LENGTH: 18
<212> TYPE: DNA
<213> ORGANISM: Artificial Sequence
<220> FEATURE:

<223> OTHER INFORMATION: Synthetic oligonucleotide primer for CK19 gene

<400> SEQUENCE: 373
caggcttcag catccttc                                                          18

<210> SEQ ID NO 374
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 374
ggtgaaccag gcttcag                                                           17

<210> SEQ ID NO 375
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 375
gtgaaccagg cttcagc                                                           17

<210> SEQ ID NO 376
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 376
gaaccaggct tcagcatc                                                          18

<210> SEQ ID NO 377
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 377
accaggcttc agcatcc                                                           17

<210> SEQ ID NO 378
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 378
agagcctgtt ccgtctc                                                           17

<210> SEQ ID NO 379
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 379
gtggaggccg acatcaac                                                          18

<210> SEQ ID NO 380

```
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 380
caggcttcag catccttc                                                 18

<210> SEQ ID NO 381
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 381
tcggacctgc tcatctg                                                  17

<210> SEQ ID NO 382
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 382
tcagtaacct cggacctg                                                 18

<210> SEQ ID NO 383
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 383
agtaacctcg gacctgc                                                  17

<210> SEQ ID NO 384
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 384
taacctcgga cctgctc                                                  17

<210> SEQ ID NO 385
<211> LENGTH: 15
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 385
aggcccctgc ttctg                                                    15

<210> SEQ ID NO 386
<211> LENGTH: 15
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 386
```

```
gccnctgctt ctggt                                              15
```

<210> SEQ ID NO 387
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 387

```
ccnctgcttc tggtacc                                            17
```

<210> SEQ ID NO 388
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 388

```
ccnctgcttc tggtacca                                           18
```

<210> SEQ ID NO 389
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 389

```
gccnctgctt ctggtacc                                           18
```

<210> SEQ ID NO 390
<211> LENGTH: 16
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 390

```
aggccnctgc ttctgg                                             16
```

<210> SEQ ID NO 391
<211> LENGTH: 16
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 391

```
ggccnctgct tctggt                                             16
```

<210> SEQ ID NO 392
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 392

```
agaatcttgt cccgcagg                                           18
```

<210> SEQ ID NO 393
<211> LENGTH: 17
<212> TYPE: DNA
<213> ORGANISM: Artificial Sequence
<220> FEATURE:

<223> OTHER INFORMATION: Synthetic oligonucleotide primer for CK19 gene

<400> SEQUENCE: 393
gaatcttgtc ccgcagg                                                17

<210> SEQ ID NO 394
<211> LENGTH: 20
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 394
tgatttcctc ctcatggttc                                             20

<210> SEQ ID NO 395
<211> LENGTH: 20
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 395
gatttcctcc tcatggttct                                             20

<210> SEQ ID NO 396
<211> LENGTH: 19
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 396
tcctcctcat ggttcttct                                              19

<210> SEQ ID NO 397
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 397
actgacctgg cctccca                                                17

<210> SEQ ID NO 398
<211> LENGTH: 15
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 398
cctcccactt ggccc                                                  15

<210> SEQ ID NO 399
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 399
agatcgacaa cgcccgtc                                               18

<210> SEQ ID NO 400

```
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 400
atcgacaacg cccgtctg                                                   18

<210> SEQ ID NO 401
<211> LENGTH: 15
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 401
atcgacaacg cccgt                                                      15

<210> SEQ ID NO 402
<211> LENGTH: 14
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 402
tcgacaacgc ccgt                                                       14

<210> SEQ ID NO 403
<211> LENGTH: 15
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 403
ccgtctggct gcaga                                                      15

<210> SEQ ID NO 404
<211> LENGTH: 17
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 404
cgtctggctg cagatga                                                    17

<210> SEQ ID NO 405
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 405
gtctggctgc agatgact                                                   18

<210> SEQ ID NO 406
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 406
```
tctggctgca gatgactt                                          18

<210> SEQ ID NO 407
<211> LENGTH: 16
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 407
tccgggcacc gatctc                                            16

<210> SEQ ID NO 408
<211> LENGTH: 16
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 408
ggcaccgatc tcgcca                                            16

<210> SEQ ID NO 409
<211> LENGTH: 15
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 409
gggcaccgat ctcgc                                             15

<210> SEQ ID NO 410
<211> LENGTH: 15
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 410
gcaccgatct cgcca                                             15

<210> SEQ ID NO 411
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 411
tcatggccga gcagaacc                                          18

<210> SEQ ID NO 412
<211> LENGTH: 16
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 412
catggccgag cagaac                                            16

<210> SEQ ID NO 413
<211> LENGTH: 41
<212> TYPE: DNA
<213> ORGANISM: Artificial Sequence
<220> FEATURE:

<223> OTHER INFORMATION: Synthetic oligonucleotide primer for CK19 gene

<400> SEQUENCE: 413
tgtagtagtg gctgtagtcg cgagctagag gtgaagatcc g          41

<210> SEQ ID NO 414
<211> LENGTH: 39
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 414
tgtagtagtg gctgtagtcg cgagatccgc gactggtac             39

<210> SEQ ID NO 415
<211> LENGTH: 42
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 415
tcgtgtagta gtggctgtag tcgagctaga ggtgaagatc cg         42

<210> SEQ ID NO 416
<211> LENGTH: 40
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 416
tcgtgtagta gtggctgtag tcggtgaaga tccgcgactg            40

<210> SEQ ID NO 417
<211> LENGTH: 40
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 417
tcgtgtagta gtggctgtag tcgagatccg cgactggtac            40

<210> SEQ ID NO 418
<211> LENGTH: 38
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 418
gtgccaccat tgagaactcc ggttcggaag tcatctgc               38

<210> SEQ ID NO 419
<211> LENGTH: 43
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 419
ggagttctca atggtggcac caactactac acgaccatcc agg        43

<210> SEQ ID NO 420

```
<211> LENGTH: 41
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 420
tgtcctgcag atcgacaacg ccgtctcaaa cttggttcgg a                           41

<210> SEQ ID NO 421
<211> LENGTH: 41
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 421
gtcctgcaga tcgacaacgc ctccgtctca aacttggttc g                           41

<210> SEQ ID NO 422
<211> LENGTH: 34
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 422
ttggcccctc agcgtacaag agctggccta cctg                                   34

<210> SEQ ID NO 423
<211> LENGTH: 36
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 423
aggtcagtgt ggaggtggcg catgtcactc aggatc                                 36

<210> SEQ ID NO 424
<211> LENGTH: 38
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 424
agcggaatcc acctccacga ggaaatcagt acgctgag                               38

<210> SEQ ID NO 425
<211> LENGTH: 40
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 425
aatccacctc cacactgacc gaggaaatca gtacgctgag                             40

<210> SEQ ID NO 426
<211> LENGTH: 39
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 426
```

```
atccacctcc acactgaccg aggaaatcag tacgctgag                           39
```

<210> SEQ ID NO 427
<211> LENGTH: 38
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 427

```
tccacctcca cactgaccga ggaaatcagt acgctgag                            38
```

<210> SEQ ID NO 428
<211> LENGTH: 38
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 428

```
tctcgccaag atcctgagtg caggcttcag catccttc                            38
```

<210> SEQ ID NO 429
<211> LENGTH: 37
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 429

```
tctcgccaag atcctgagtg ggtgaaccag gcttcag                             37
```

<210> SEQ ID NO 430
<211> LENGTH: 37
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 430

```
tctcgccaag atcctgagtg gtgaaccagg cttcagc                             37
```

<210> SEQ ID NO 431
<211> LENGTH: 38
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 431

```
tctcgccaag atcctgagtg gaaccaggct tcagcatc                            38
```

<210> SEQ ID NO 432
<211> LENGTH: 37
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 432

```
tctcgccaag atcctgagtg accaggcttc agcatcc                             37
```

<210> SEQ ID NO 433
<211> LENGTH: 38
<212> TYPE: DNA
<213> ORGANISM: Artificial Sequence
<220> FEATURE:

<223> OTHER INFORMATION: Synthetic oligonucleotide primer for CK19 gene

<400> SEQUENCE: 433
tcgccaagat cctgagtgac caggcttcag catccttc                          38

<210> SEQ ID NO 434
<211> LENGTH: 40
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 434
agatcctgag tgacatgcga agcaggcttc agcatccttc                        40

<210> SEQ ID NO 435
<211> LENGTH: 1275
<212> TYPE: DNA
<213> ORGANISM: Homo sapiens

<400> SEQUENCE: 435
atggatttca gtcgcagaag cttccacaga agcctgagct cctccttgca ggcccctgta    60
gtcagtacag tgggcatgca gcgcctcggg acgacaccca gcgtttatgg gggtgctgga   120
ggccggggca tccgcatctc caactccaga cacacggtga actatgggag cgatctcaca   180
ggcggcgggg acctgtttgt tggcaatgag aaaatggcca tgcagaacct aaatgaccgt   240
ctagcgagct acctagaaaa ggtgcggacc ctggagcagt ccaactccaa acttgaagtg   300
caaatcaagc agtggtacga aaccaacgcc ccgagggctg gtcgcgacta cagtgcatat   360
tacagacaaa ttgaagagct gcgaagtcag attaaggatg ctcaactgca aaatgctcgg   420
tgtgtcctgc aaattgataa tgctaaactg gctgctgagg acttcagact gaagtatgag   480
actgagagag gaatacgtct aacagtggaa gctgatctcc aaggcctgaa taggtctttt   540
gatgacctaa ccctacataa aacagatttg gagattcaaa ttgaagaact gaataaagac   600
ctagctctcc tcaaaaagga gcatcaggag gaagtcgatg gcctacacaa gcatctgggc   660
aacactgtca atgtggaggt tgatgctgct ccaggcctga accttggcgt catcatgaat   720
gaaatgaggc agaagtatga agtcatggcc cagaagaacc ttcaagaggc caagagacag   780
tttgagagac agactgcagt tctgcagcaa caggtcacag tgaatactga agaattaaaa   840
ggaactgagg ttcaactaac ggagctgaga cgcacctccc agagccttga gatagaactc   900
cagtcccatc tcagcatgaa agagtctttg gagcacactc tagaggagac caaggcccgt   960
tacagcagcc agttagccaa cctccagtcg ctgttgagct ctctggaggc ccaactgatg  1020
cagattcgga gtaacatgga acgccagaac aacgaatacc atatccttct tgacataaag  1080
actcgacttg aacaggaaat tgctacttac cgccgccttc tggaaggaga agacgtaaaa  1140
actacagaat atcagttaag caccctggaa gagagagata taaagaaaac caggaagatt  1200
aagacagtcg tgcaagaagt agtggatggc aaggtcgtgt catctgaagt caaagaggtg  1260
gaagaaaata tctaa                                                  1275

<210> SEQ ID NO 436
<211> LENGTH: 21
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 436
ttcatgctga gatgggactg g                                              21

<210> SEQ ID NO 437
<211> LENGTH: 21
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 437
gctgagatgg gactggagtt c                                              21

<210> SEQ ID NO 438
<211> LENGTH: 21
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 438
caatttgcag gacacaccga g                                              21

<210> SEQ ID NO 439
<211> LENGTH: 19
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 439
gaggttcaac taacggagc                                                 19

<210> SEQ ID NO 440
<211> LENGTH: 20
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 440
gttcaactaa cggagctgag                                                20

<210> SEQ ID NO 441
<211> LENGTH: 18
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 441
actaacggag ctgagacg                                                  18

<210> SEQ ID NO 442
<211> LENGTH: 19
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 442
attgaagagc tgcgaagtc                                                 19

<210> SEQ ID NO 443
<211> LENGTH: 23
<212> TYPE: DNA
<213> ORGANISM: Artificial Sequence
<220> FEATURE:

<223> OTHER INFORMATION: Synthetic oligonucleotide primer for CK20 gene

<400> SEQUENCE: 443
cgactacagt gcatattaca gac                                             23

<210> SEQ ID NO 444
<211> LENGTH: 18
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 444
cagcaacagg tcacagtg                                                   18

<210> SEQ ID NO 445
<211> LENGTH: 19
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 445
ctagaggaga ccaaggccc                                                  19

<210> SEQ ID NO 446
<211> LENGTH: 20
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 446
tctagaggag accaaggccc                                                 20

<210> SEQ ID NO 447
<211> LENGTH: 20
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 447
agaccaaggc ccgttacagc                                                 20

<210> SEQ ID NO 448
<211> LENGTH: 21
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 448
ctgctgagga cttcagactg a                                               21

<210> SEQ ID NO 449
<211> LENGTH: 18
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 449
agagagctca acagcgac                                                   18

<210> SEQ ID NO 450

```
<211> LENGTH: 18
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 450
tccagagagc tcaacagc                                                       18

<210> SEQ ID NO 451
<211> LENGTH: 17
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 451
acagcgactg gaggttg                                                        17

<210> SEQ ID NO 452
<211> LENGTH: 17
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 452
agctcaacag cgactgg                                                        17

<210> SEQ ID NO 453
<211> LENGTH: 19
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 453
cttggagatc agcttccac                                                      19

<210> SEQ ID NO 454
<211> LENGTH: 22
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 454
gtagggttag gtcatcaaag ac                                                  22

<210> SEQ ID NO 455
<211> LENGTH: 18
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 455
gcgttccatg ttactccg                                                       18

<210> SEQ ID NO 456
<211> LENGTH: 21
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 456
```

```
gcagttgagc atccttaatc t                                              21

<210> SEQ ID NO 457
<211> LENGTH: 17
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 457
ctcaaggctc tgggagg                                                   17

<210> SEQ ID NO 458
<211> LENGTH: 20
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 458
gactgagaga ggaatacgtc                                                20

<210> SEQ ID NO 459
<211> LENGTH: 18
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 459
gccagttagc caacctcc                                                  18

<210> SEQ ID NO 460
<211> LENGTH: 16
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 460
cagttagcca acctcc                                                    16

<210> SEQ ID NO 461
<211> LENGTH: 40
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 461
ttcatgctga gatgggactg ggaggttcaa ctaacggagc                          40

<210> SEQ ID NO 462
<211> LENGTH: 41
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 462
ttcatgctga gatgggactg ggttcaacta acggagctga g                        41

<210> SEQ ID NO 463
<211> LENGTH: 39
<212> TYPE: DNA
<213> ORGANISM: Artificial Sequence
<220> FEATURE:
```

```
<223> OTHER INFORMATION: Synthetic oligonucleotide primer for CK20 gene

<400> SEQUENCE: 463
ttcatgctga gatgggactg gactaacgga gctgagacg                              39

<210> SEQ ID NO 464
<211> LENGTH: 40
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 464
gctgagatgg gactggagtt cgaggttcaa ctaacggagc                             40

<210> SEQ ID NO 465
<211> LENGTH: 41
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 465
gctgagatgg gactggagtt cgttcaacta acggagctga g                           41

<210> SEQ ID NO 466
<211> LENGTH: 39
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 466
gctgagatgg gactggagtt cactaacgga gctgagacg                              39

<210> SEQ ID NO 467
<211> LENGTH: 40
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 467
caatttgcag gacacaccga gattgaagag ctgcgaagtc                             40

<210> SEQ ID NO 468
<211> LENGTH: 37
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 468
ctagaggaga ccaaggccca gagagctcaa cagcgac                                37

<210> SEQ ID NO 469
<211> LENGTH: 38
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 469
tctagaggag accaaggccc tccagagagc tcaacagc                               38

<210> SEQ ID NO 470
```

```
<211> LENGTH: 37
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 470
tctagaggag accaaggccc acagcgactg gaggttg                              37

<210> SEQ ID NO 471
<211> LENGTH: 38
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 471
agaccaaggc ccgttacagc agagagctca acagcgac                             38

<210> SEQ ID NO 472
<211> LENGTH: 38
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 472
agaccaaggc ccgttacagc tccagagagc tcaacagc                             38

<210> SEQ ID NO 473
<211> LENGTH: 37
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 473
agaccaaggc ccgttacagc agctcaacag cgactgg                              37

<210> SEQ ID NO 474
<211> LENGTH: 40
<212> TYPE: DNA
<213> ORGANISM: Artificial Sequence
<220> FEATURE:
<223> OTHER INFORMATION: Synthetic oligonucleotide primer for CK20 gene

<400> SEQUENCE: 474
ctgctgagga cttcagactg acttggagat cagcttccac                           40

<210> SEQ ID NO 475
<211> LENGTH: 18
<212> TYPE: DNA
<213> ORGANISM: Artificial Sequence
<220> FEATURE:
<223> OTHER INFORMATION: Synthetic oligonucleotide primer for CK19 gene

<400> SEQUENCE: 475
gttgatgtcg gcctccac                                                   18
```